United States Patent [19]
Curran et al.

[11] Patent Number: 6,156,896
[45] Date of Patent: *Dec. 5, 2000

[54] FLUOROUS REACTION AND SEPARATION SYSTEMS

[75] Inventors: Dennis P. Curran; Sabine Hadida Ruah; Masahide Hoshino; Armido Studer; Peter Wipf; Patrick Jeger; Sun-Young Kim; Rafael Ferritto, all of Pittsburgh, Pa.

[73] Assignee: University of Pittsburgh, Pittsburgh, Pa.

[*] Notice: This patent is subject to a terminal disclaimer.

[21] Appl. No.: 09/080,274

[22] Filed: May 15, 1998

Related U.S. Application Data

[63] Continuation of application No. 08/690,491, Jul. 31, 1996, Pat. No. 5,859,247, which is a continuation-in-part of application No. 08/671,945, Jun. 28, 1996, Pat. No. 5,777,121.

[51] Int. Cl.$^7$ .............................. C07F 7/00; C07C 17/00

[52] U.S. Cl. ................................ 546/2; 549/206; 556/87; 556/88; 570/241; 585/899; 560/116; 560/123

[58] Field of Search ................................ 546/2; 549/206; 556/87, 88; 570/241; 585/899; 560/116, 123

[56] References Cited

U.S. PATENT DOCUMENTS

| | | | |
|---|---|---|---|
| 5,463,082 | 10/1995 | Horvath et al. | 549/46 |
| 5,777,121 | 7/1998 | Curran et al. | 546/2 |

OTHER PUBLICATIONS

Gronowitz et al, "The Effect of Some Additives on the Still PD0–Catalyzed Cross–Coupling Reaction," J. of Organometallic Chemistry, 460, 127–129 (1993).

Boutevin et al, "Study of the Alkylation of Chlorosilanes. Part 1, Synthesis of tetra (1H,1H,2H,2H–polyfluoroalkyl)silanes," J. of Fluorine Chemistry, 60, 211–223 (1993).

Gladysz, "Are Teflon 'Ponytails' the Coming Fashion for Catalysts?," Science, 266, 55–56 (1994).

Horvath et al, "Facile Catalyst Separation Without Water: Fluorous Biphase Hydroformulation of Olefins," Science, 266, 72–75 (1994).

Zhu, "A Novel Reaction Medium: Pefrluorocarbon Fluids," Synthesis, 953–954 (1993).

Houk et al, "Stereoselective Nitrile Oxide Cycloadditions to Chiral Allyl Ethers and Alcohols. The 'Inside Alkoxy' Effect,"J. Am. Chem. Soc, 106, 3880–3882 (1984).

Berendensen et al., (Heptadecafluorodecyl)dimethylsilyl Bonded Phase for Reversed–Phase Liquid Chromatography, Anal. Chem., 52, 1990–1993 (1980).

Stork et al., "A Catalytic Tin System for Trapping of Radicals from Cyclization Reaction. Regio–and Stereocontrolled Formation of Two Adjacent Chiral Centers," J. Am. Chem. Soc., 108, 303–304 (1986).

Stille, The Palladium–Catalyzed Cross–Coupling Reactions of Organotin Reagents with Organic Electrophiles, Agnew. Chem. Int. Ed. Engl., 25, 508–524 (1986).

Billiet et al, "Retention and Selectivity Characteristics of Non–Polar Perfluorinated Stationary Phase for Liquid Chromotography," J. of Chromotorgaphy, 218, 443–454 (1981).

Mitchell, Paladium–Catalysed Reactions of Organotin Compounds, Synthesis, 803–815 (1992).

Deshpande, "Formation of Carbon–Carbon Bond on Solid Support: Application of the Stille Reaction," Tetrahedron Letters, 31, 5613–5614 (1994).

Wipf et al., A Solid Phase Protocol of the Biginelli Dihydropyrimidine Synthesis Suitable for Combinatorial Chemistry, Tetrahedron Letters, 43, 7819–7822 (1995).

Ugi, From Isocyanides via Four–Component Condensations to Antibiotic Syntheses, Agnew. Chem. Int. Ed. Engl., 21, 810–819, (1982).

Sisido et al, "Formation of Organotin–Nitrogen Bonds III. N–Trialkyltin–5–Substituted Tetrazoles," J. Organometallic Chem., 33, 337–346 (1971).

Hudlicky, Chemistry of Organic Fluorine Compounds, PTR Prentice Hall, New York, ix–xiv, 1, 542–545 (1992).

Davies, Comprehensive Organometallic Chemistry A Review of the Litereature 1982–1994, Pergamon, v, 217–218, 224–231, 234–238, 243–245, 254, 270 (1995).

Pereyre et al, Tin in Organic Synthesis, Butterworths, London, Forward, Preface and Table of Contents (1987).

Padwa, 1,3–Dipolar Cycloaddition Chemistry, vol. 1, John Wiley & Sons, New York, v, vi, xi, 291–292 (1984).

Greene et al, Protective Groups in Organic Synthesis, John Wiley & Sons, New York, v, ix–xi, 10–15, 176–777, 224–5, 312–315 (1991).

Boutevin et al., "Study of the Alkylation of Chlorosilanes," J. of Fluorine Chemistry, 68, 71–77 (1994).

Curran, D.P., Proposal to National Science Foundation, "Mechanistic and Synthetic Studies of New Organic Transormations," 18–19. Funded Jul. 1, 1995.

*Primary Examiner*—Porfirio Nazario-Gonzalez
*Attorney, Agent, or Firm*—Bartony & Hare

[57] ABSTRACT

The present invention provides several methods of synthesis and separation in which organic/fluorous phase separation techniques are used to effect separations. The present invention also provides novel compositions of matter comprising fluorous Si, Sn and Ge compounds.

3 Claims, 16 Drawing Sheets a) volatile product b) the reaction solvent was THF c) the reaction solvent was DMF Products 15 from Grignard Reactions with CH₃MgBr or PhMgBr with yields and GC purities (in parenthesis)

R = $CH_3$, 83%; *i*-Bu, 87%; $PhCH_2$, 77%; *p*-$CH_3C_6H_4$, 61%; *p*-$OMeC_6H_4$, 72%; Ph, 59%; *p*-$NO_2C_6H_4$, <10%.

FLUOROUS REACTION AND SEPARATION SYSTEMS

RELATED REFERENCE

The present application is a continuation of Ser. No. 08/690,491 filed Jul. 31, 1996 U.S. Pat. No. 5,859,247 which is a continuation-in-part application of U.S. patent application Ser. No. 08/671,945, entitled Fluorous Reaction Systems and filed Jun. 28, 1996, now U.S. Pat. No. 5,777,121 the disclosure of which is incorporated herein by reference.

GOVERNMENT INTERESTS

This invention was made with government support under grant #RO1 GM33372 awarded by the National Institutes of Health and under grant #CHE-9501345 awarded by the National Science Foundation. The government has certain rights in this invention.

FIELD OF THE INVENTION

The present invention relates to novel compositions and to methods of carrying out chemical reactions.

BACKGROUND OF THE INVENTION

Organic compounds are purified on a daily basis in uncounted numbers of research and commercial laboratories and plants around the world. Purification costs account for a significant fraction of the expenses for organic compounds developed and sold by chemical, pharmaceutical, and other industries. Chromatographic methods of purification are immensely important, yet they are also expensive and time consuming. Simpler but sometimes less effective methods are based on techniques of phase separation. Four phases are commonly used in standard laboratory separation methods: a gas phase, a solid phase, and two liquid phases—organic and aqueous. Among the phase separation techniques, liquid-liquid extractions play a time-honored role in the purification of organic compounds. These extractions are almost always conducted with an organic solvent and water. Most frequently, they are used to separate (that is, purify) organic compounds from inorganic compounds. A less frequent but still important application of organic-water extractions is an acid-base extraction.

It is not widely recognized by synthetic organic chemists that there is a "third liquid phase", the fluorocarbon (or "fluorous") phase, whose members are not miscible in either water or many organic solvents. See, for example, Hudlicky, M. "Chemistry of organic Fluorine Compounds", Ellis Horwood: Chichester (1992). As used herein, the term "fluorous liquid phase" refers to a liquid phase comprising one or more solvents rich in carbon fluorine bonds. A fluorous liquid phase is substantially immiscible with an "organic phase" and forms a liquid-liquid biphasic mixture with an organic phase.

As used herein, the term "fluorous", when used in connection with an organic (carbon-containing) molecule, refers generally to an organic molecule having a domain or a portion thereof rich in carbon-fluorine bonds (for example, fluorocarbons, fluorohydrocarbons, fluorinated ethers and fluorinated amines). Such portion or domain may comprise part of a fluorous compound or the entire fluorous compound. In general, compounds comprising a relatively high weight percentage of fluorine partition preferentially into the fluorous liquid phase in a fluorous/organic liquid biphasic mixture. See U.S. Pat. No. 5,463,082. As used herein, the terms "fluorocarbons" and "perfluorocarbons" include organic compounds in which all hydrogen atoms bonded to carbon atoms have been replaced by fluorine atoms. The terms "fluorohydrocarbons" and "hydrofludrocarbons" include organic compounds in which at least one hydrogen atom bonded to a carbon atom has been replaced by a fluorine atom. Saturated perfluorocarbon fluids have important applications in surface chemistry, biology, and engineering. Most organic compounds are completely or substantially insoluble in fluorocarbon fluids, and many organic solvents are immiscible therein, although this miscibility depends somewhat on the fluorous-organic pairing. Solvents like carbon tetrachloride, ether, and THF have the highest solubilities in fluorocarbon fluids, and pairings of fluorocarbon fluids with these solvents are either miscible or can be made miscible by slight warming.

There are a wide assortment of fluorocarbon fluids commercially available under trade names like "Flutec™" and "Fluorinert™". These fluids are made industrially by chemical or electrochemical fluorination processes. Most of these are mixtures of fluorocarbons with similar boiling points (sometimes with small amounts of fluorinated ethers). These mixtures are roughly analogous to the "petroleum ether" solvents often used in organic chemistry. Fluorinated ethers and fluorinated amines are also commercially available.

Although rarely referred to as such, these fluorocarbon "fluids" are effectively solvents. The first application of fluorocarbon solvents in the area of traditional organic synthesis appeared in 1993 when D. W. Zhu described a series of transesterification reactions in the Fluorinert Fluid™ FC-77 (a fluorocarbon mixture containing mostly isomers of $C_8F_{18}$, bp 97° C.). Zhu, D. W., *Synthesis*, 953–54 (1993). As illustrated in the following example, low boiling alcohols were replaced by high boiling ones, and phase separation was used at two stages.

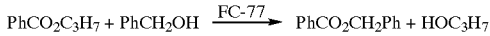

$$PhCO_2C_3H_7 + PhCH_2OH \xrightarrow{FC-77} PhCO_2CH_2Ph + HOC_3H_7$$

*alcohol separates in a "Dean-Stark" trap
*product separates from FC-77 on cooling First, an "inverse Dean-Stark" trap was used to separate the low-boiling alcohol from the reaction mixture and thereby drive the equilibrium. Second, the product ester separated from the FC-77 on cooling. Another common fluorocarbon fluid is FC-72™, a mixture of $C_6F_{14}$ isomers with a boiling point of 56° C. FC-72 and FC-77 are commercially available from 3M.

Shortly after the work of Zhu, Hórvath and Rabai described the synthesis of a "fluorous" phosphine ligand and used this to generate a rhodium catalyst for a standard hydroformylation reaction. Hórvath, I. T. and Rábai, J., *Science*, 266, 72–75 (1994). See also U.S. Pat. No. 5,463,082; and Gladysz, J. A., *Science*, 266, 55 (1994). The hydroformylation was conducted in a liquid biphasic mixture of perfluoromethylcyclohexane (fluorous solubilizing solvent) and toluene (organic solubilizing solvent) under a $CO/H_2$ atmosphere as illustrated below.

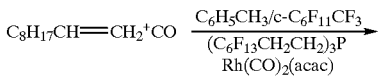

$$C_8H_{17}CH=CH_2 + CO \xrightarrow[Rh(CO)_2(acac)]{C_6H_5CH_3/c-C_6F_{11}CF_3 \atop (C_6F_{13}CH_2CH_2)_3P} C_8H_{17}CH(CHO)CH_3 + C_{10}H_{21}CHO$$

*two phase reaction
*catalyst in fluorous phase can be reused

The products were separated from the catalyst by separation of the two liquid reaction phases, and the recovered catalyst from the fluorinated phase was successfully reused in another hydroformylation.

The distinctive physiochemical properties of a fluorous liquid phase can be used advantageously to provide unexpected solvent effects including altered and improved product yields, reactivities and/or selectivities. Likewise, physiochemical differences between fluorous molecules and organic (that is, non-fluorous) molecules provide a valuable tool to effect separation.

It is, therefore, very desirable to develop additional fluorous reaction components, reaction systems, reaction schemes and separation schemes.

SUMMARY OF THE INVENTION

The term "reagent," as used herein in connection with combinatorial syntheses, refers to a chemical entity that is required for a reaction but contributes either an invariant piece or no piece to the products of a combinatorial synthesis. The term "reactant," as used herein in connection with combinatorial synthesis refers generally to a type of molecule that contributes a variable piece to the products of a combinatorial synthesis. The distinction between the terms "reactant" and "reagent" in "common" (non-combinatorial) organic syntheses is vague, but those skilled in the art often refer to a reaction component as a reagent if it contributes no piece, a rather small piece, or a piece without carbon atoms therein to the target product. As used herein, the term "reagent" includes a catalyst if used in a substoichiometric quantity.

As used herein, the term "substrate" refers generally to a reaction component that is a major starting material of a synthetic reaction, normally prepared in a prior step. The term "target product" refers generally to the target or desired molecule(s) of a transformation derived by reaction of the substrate with the other reaction component(s) in the medium. The terms "side product" or "byproduct" refer generally to a product derived from any component(s) of the reaction medium which is not the target product and is preferably separated therefrom.

The term "organic/fluorous phase separation technique" refers generally to any separation technique that is based upon the presence of the fluorous group(s) on a fluorous component or molecule to establish a separation between compounds bearing the fluorous group(s) and compounds not bearing the fluorous group(s). Such techniques include, but are not limited to, simple extractions between a fluorous liquid and an organic liquid. The fluorous phase can also consist the of fluorous component(s) to be separated themselves as, for example, a liquid or a solid phase. Also included are techniques like countercurrent distribution and "solid phase extraction." Solid phase extractions involve, for example, the use of highly fluorinated polymers or stationary phases in combination with organic or organic/aqueous mobile phases. Chromatography materials consisting of bonded stationary phases (for example, "S-OSi(Me)$_2$(CH$_2$)$_n$Rf", where "S" is a standard support like silica gel, "n" is 2 or 3, and Rf is a linear or branched perfluoroalkyl group) are known. Some of these stationary phases (that is, fluorous solid phases) are commercially available (for example, Fluofix™ Columns) from companies like Keystone Scientific (USA) and NEOS Co. (Japan). It is known that highly fluorinated compounds are strongly retained by these columns when they are eluted with organic or organic/aqueous mobile phases, while organic compounds pass through. See, for example, H. A. H. Billiet, et al, *J. Chromat.*, 218, 443 (1981) and G. E. Berendsen, et al., *Anal. Chem.*, 52, 1990 (1980). However, elution with a fluorous mobile phase will release all retained fluorous compounds. In favorable cases, even standard "normal" (silica, alumina, etc.) or "reverse phase" (C18) stationary phases can be used because the presence of the fluorous group dramatically alters the mobility of compounds bearing that group relative to compounds not bearing that group. All preferred organic/fluorous phase separation techniques enable relatively simple separations of fluorous and non-fluorous components.

The terms "fluorous substrate," "fluorous reactant," "fluorous reagent" etc. (or, generally, "fluorous reaction component") refer generally to a reaction component comprising a portion rich in carbon-fluorine bonds. Fluorous reaction components generally partition preferentially into (or onto) the fluorous phase. The term "fluorous reaction component" also includes, however, a reaction component that (1) comprises a portion rich in carbon-fluorine bonds, (2) does not partition preferentially into a fluorous phase, but (3) forms fluorous product(s) and/or byproduct(s) comprising such a portion rich in carbon-fluorine bonds during reaction. The fluorous products and/or byproducts partition preferentially into a fluorous phase. The terms "organic substrate," "organic reactant," "organic reagent" etc. (or, generally, "organic reaction component") refer generally to a reaction component that does not comprise a portion rich in carbon-fluorine bonds. organic reaction components and organic compounds generally partition preferentially into an organic (that is, non-fluorous) phase (for example, into an organic layer in an organic/fluorous liquid extraction).

The present inventors have discovered that liquid biphasic reaction systems comprising a fluorous phase and a non-fluorous phase previously investigated by others are not operable in a number of reaction systems. Indeed, in many cases the partition coefficients for the reaction components (that is, reagents, reactants and catalysts) may be such that the phase separation between the liquid phases of biphasic systems severely inhibits or prevents reaction. It has been discovered that the processes of reaction and phase separation (that is, for recovery of product) are preferably separated.

Therefore, in one embodiment of the present invention, all of the reaction components of the reactions of the present invention, including any reagents and reactants, are preferably substantially soluble in an "organic/fluorous solubilizing liquid phase" during the course of the reaction. As used herein, the term "organic/fluorous solubilizing liquid phase" refers to a liquid phase comprising a solvent system adapted or selected to substantially solubilize both an organic reaction component(s) and a fluorous reaction component(s). It is not necessary that the reaction components be completely soluble in the organic/fluorous solubilizing liquid phase at any or all times during the reaction. Each reaction component (organic or fluorous) has at least approximately a 0.1 millimolar solubility therein and, more preferably, at least approximately a 1 millimolar solubility therein. The target product and/or any byproducts need not be substantially soluble in the organic/fluorous solubilizing liquid phase. Indeed, the target product and/or any byproducts may, for example, form an immiscible liquid phase or an insoluble solid phase.

For reaction in an organic/fluorous solubilizing liquid phase, the organic/fluorous solubilizing liquid phase may comprise: (i) an organic solvent or a mixture of organic solvents (for example, carbon tetrachloride, THF and/or ether); (ii) a homogeneous mixture of an organic solvent (or solvents) with a fluorous solvent (or solvents) (for example, FC-72 mixed with carbon tetrachloride, ether or THF); or a hybrid organic/fluorous solvent (or solvents) used either alone or in combination with either or both an organic solvent (or solvents) and a fluorous solvent (or solvents). Solvent systems as described above are known in the art.

The organic/fluorous solubilizing liquid phase is a homogeneous liquid phase with respect to organic and fluorous liquid phases. As used herein, the term "homogeneous liquid phase" refers to a liquid phase in which no internal liquid-liquid physical boundaries (for example, a meniscus) are visible between an organic phase and a fluorous phase. See, for example, *CRC Handbook of Chemistry and Physics*, 61$^{st}$ Edition, C-691 (1980) (determining miscibility on the basis of either observation or absence of an interfacial meniscus). Thus, there are no internal fluorous-organic physical boundaries observed in the organic/fluorous solubilizing liquid phases of the present invention. Such organic/fluorous solubilizing liquid phases may form a liquid-liquid physical boundary with an aqueous phase in some reactions where water is present, however.

As used herein, the term "hybrid organic/fluorous solvent" refers to a solvent comprising both an organic (for example, a hydrocarbon) portion or domain and a fluorous (for example, a fluorocarbon or fluorohydrocarbon) portion or domain. In general, hybrid organic/fluorous solvents will not form a biphasic system or mixture when mixed with either organic solvents or with fluorous solvents. Some hybrid organic/fluorous solvents may form a biphasic mixture with an organic solvent or a fluorous solvent (for example, FC-72 and $CF_3CH_2OH$ form a biphasic mixture), but such hybrid organic fluorous solvents are still useful either alone or in combination with other solvents for creating an organic/fluorous solubilizing liquid phase. Examples of hybrid organic/fluorous solvents include, but are not limited to, benzotrifluoride (BTF; $C_6H_5CF_3$), trifluoroethanol, p-chlorobenzotrifluoride ($ClC_6H_4CF_3$ ), and 1,4-bis(trifluoromethyl)benzene ($CF_3C_6H_4CF_3$). Examples of homogeneous mixtures of hybrid organic/fluorous solvents with organic solvents and/or fluorous solvents for use in the present invention include BTF/$CH_2Cl_2$, $H_2O$/BTF/THF/acetone, BTF/FC-72 and BTF/FC-72/ether. Hybrid organic/fluorous solvents are somewhat analogous to hybrid organic/aqueous solvents such as alcohols (for example, $CH_3CH_2OH$) which have an organic portion and an aqueous (or water-like) portion and generally do not form a biphasic mixture when mixed with either organic solvents or water.

The present invention thus generally provides a method for carrying out a chemical reaction comprising the steps of forming an organic/fluorous solubilizing liquid phase comprising a solvent system. The solvent system is selected or adapted to substantially solubilize a fluorous reaction component or components (that is, a fluorous reagent, a fluorous catalyst and/or a fluorous reactant). The fluorous reaction component is functionalized to comprise at least one fluorous moiety having the formula —$(R)_d(Rf)_e$. $(Rf)_d$ is at least one fluorous group and e is a whole number. $(R)_d$ is an organic (for example, hydrocarbon) spacer group, which may be present or absent, and d is an integer equal to at least zero. The solvent system is also adapted to substantially solubilize an organic reaction component or components convertible to an organic product in a reaction scheme including one or more reactions.

After synthesis of the organic product in the organic/fluorous solubilizing liquid phase, an organic/fluorous phase separation technique is used to effect separation of an organic target product from any remaining fluorous reaction components and/or any fluorous byproducts formed in the reaction. In a preferred embodiment, a co-solvent or co-solvents is preferably added to the organic/fluorous solubilizing liquid phase to effect a phase separation into at least a fluorous liquid phase and an organic liquid phase. A solid phase, a gas phase and/or an aqueous phase may also be present. In some cases, it may be preferable to remove by evaporation part or all of the organic/fluorous solubilizing liquid phase before addition of the co-solvent or co-solvents.

The fluorous reaction component(s) thus preferably comprises a sufficient number of fluorous moieties to render any excess fluorous reaction components and fluorous byproducts derived from the fluorous reaction components readily separable in an organic/fluorous phase separation technique. In an organic/fluorous liquid extraction, for example, excess fluorous reaction component(s) and/or fluorous byproduct(s) are preferentially partitionable into the fluorous liquid phase after a single or a series of extractions. Likewise, the organic product is preferentially partitionable into the organic liquid phase after a single or a series of extractions.

The organic spacer group (R) d may contain H and C, or may contain groups containing O, N, S, P, As and Si in addition to H and C in the backbone and/or as substituents. In general, $(R)_d$ is rich in hydrogen atoms in comparison to $(Rf)_e$. Preferably, d is an integer equal to at least zero or any whole number. More preferably, d is a whole number less than 4. Most preferably d is 0, 1, 2 or 3. In many cases, an organic spacer group is preferable or required because of the strongly electron withdrawing nature of fluorous groups. Addition of a hydrocarbon group (for example, a —$CH_2CH_2$— group) as a spacer group between the fluorous group and a reaction component generally reduces the electron withdrawing effect of the fluorous group on the reaction component. In some cases, the electron withdrawing nature of the fluorous group may have no effect or a beneficial effect upon the reaction component. In such cases, the organic spacer group may be omitted (that is, d=0).

The fluorous reaction components often may contain a plurality of fluorous moieties (for example, Q-$[(R)_d(Rf)_e]_z$, wherein Q represents a standard reaction component and Z>1) having a significant proportion of fluorine atoms as compared to the molecular weight of the entire reaction component. The fluorous moieties may be attached to the same atom on the fluorous reaction component(s) or to different atoms thereon. Sufficient fluorous moieties are preferably used such that any fluorous reaction components and/or any fluorous byproducts remaining after reaction are separable from the organic target product via an organic/fluorous phase separation technique. However, the chemical activity of underlying reaction component Q is preferably changed little or not at all by addition thereto of fluorous portion $(Rf)_e$.

In cases in which the fluorous reaction component(s) are not completely reacted, preferably, at least approximately 20 wt % to approximately 90 wt %, and, more preferably, about 50 wt % to 90 wt % of the total weight of a fluorous reaction component comprises fluorine. In all such cases, sufficient fluorine content and appropriate structure should be present to render the fluorous reaction component separable in an organic/fluorous phase separation technique (for example, partitionable preferentially into the fluorous liquid phase after phase separation) to enable separation thereof from the organic target product.

In cases in which a fluorous reaction component is used in such quantities that it is completely reacted, only the resulting fluorous byproduct(s) must be separated from the organic target product. In such cases, preferably, at least approximately 20 wt % to approximately 90 wt %, and, more preferably, about 50 wt % to 90 wt % of the total weight of a fluorous byproduct(s) comprise fluorine. As clear to one of ordinary skill in the art, if the organic portion of the fluorous reaction component was relatively large in comparison to any organic portion of the corresponding fluorous byproduct (s), the fluorine wt % of the fluorous reaction component can be less than 20 wt %. As also clear to one of ordinary skill in the art, the preferential partitioning of the fluorous reaction component to the fluorous phase not important in these cases. In general, any fluorous compound to be separated from an organic compound in an organic/fluorous phase separation technique preferably comprises at least approximately 20 wt % fluorine, and, more preferably, at least 50 wt % fluorine, to facilitate separation.

Typically, known standard (non-fluorous) reactions can be carried out under the present invention with one or more fluorous functionalized reaction components within the range of reaction conditions used in the corresponding standard reactions. The present invention is equally applicable, however, to newly developed organic reactions.

The fluorous reaction components can be prepared by fluorination or fluoro-functionalization of a starting reaction component, by modification of another fluorous reaction component, or by total synthesis. For example, fluorous tin reaction components can be made conveniently in one or more steps. An illustrative method of synthesis of fluorous tin reaction components is the combination of known nucleophiles, for example Grignard reagents such as $RfCH_2CH_2MgBr$, with known tin electrophiles, for example $Cl_3SnX$. This combination leads either directly or through the agency of one or more additional transformations wherein one group X is replaced by another to preparation of a large new class of fluorous tin reaction components $[RfCH_2CH_2]_3SnX$. The interchange of groups X in organotin chemistry is well known to those skilled in the art and can be accomplished by a large class of reactions wherein a nucleophilic precursor of the product X group replaces a leaving group X (for example, a halogen or triflate) in the tin precursor (for example, stannylation of an alcohol), by reactions wherein a tin nucleophile (X=metal) adds to or displaces an electrophile precursor of the product X group (for example, a substitution reaction of a stannyl metal with an allyl halide), or by reactions in which the tin SnX bond adds to a multiple bond (for example, hydrostannylation of an alkene or a carbonyl group). Similarly, the use of other standard classes of nucleophiles and tin electrophiles allows entry into related groups of reagents with other fluorous substituents on tin. Analogous transformations can generally be applied to the synthesis of related silicon and germanium reaction components.

Transformations under the method of the present invention generally parallel the transformations of known "non-fluorous" reaction components with the advantages that the fluorous reaction components and any fluorous byproducts derived from the fluorous reaction components can be removed from the organic products by one or more organic/fluorous phase separation techniques (for example by organic/fluorous liquid-liquid extraction). The recovered fluorous reaction components can often either be reused directly or recycled by standard reactions to reusable forms. These are significant advantages compared to the standard reaction components.

The method of the present invention also offers significant advantages over the current fluorous multiphase reactions. See U.S. Pat. No. 5,463,082. While there are benefits to conducting some types of catalytic and other organic reactions in multiphase systems, the vast majority of organic reactions are preferentially conducted in liquid phases in which the key reaction components have substantial solubility. Separation into immiscible fluorous and organic liquid phases is not expected to be beneficial for many important reactions classes and may often be detrimental. In the method of the present invention, fluorous reaction components and organic reaction components react under conditions in which both are substantially soluble in the same organic/fluorous solubilizing liquid phase.

For example, organic reactions of tin, germanium, and silicon reagents $R_3MX$ (where M=Si, Ge, Sn and X=an atom or a group participating in a reaction with an organic compound) are routinely used by those skilled in the art to accomplish many different organic transformations. Most reactions of these reaction components are preferentially conducted in a homogeneous liquid phase. Reactions of the fluorous analogs of these reaction components, $[(Rf)_e(R)_d]_3MX$ are likewise preferentially conducted in a homogeneous liquid phase. For example, the reagents $[C_6F_{13}CH_2CH_2]_3SiX$ where X=H and Cl are known compounds that can be used by the methods described herein to conduct reactions such as hydrosilylation and reduction (X=H) or silylation (X=Cl) that are analogous to the reactions of standard (non-fluorous) reagents $R_3SiX$ where X=H or Cl and R=alkyl or cycloalkyl. Likewise, fluorous allyl- and vinyltin and allyl- and vinylsilane reaction components can be used for typical ionic allylations and vinylations, and fluorous allyl- and vinyltin reaction components can be used for typical radical allylations and vinylations as well. These are but a few examples selected from the rich, well known chemistry of tin, germanium and silicon.

Fluorous compounds remaining after reactions of the present invention may, for example, be separated from organic compounds by a simple liquid-liquid extraction, thereby providing a very substantive purification that for many reactions would previously have required chromatography or some other more demanding technique. The present invention provides significant advantages in both "common" and "combinatorial" organic synthesis.

In common organic synthesis, individual steps are conducted sequentially until the final target molecule or product is made. In combinatorial organic synthesis, the target is not a single molecule but instead a "library" of tens to millions of molecules. Multiple reactions are conducted either together or in parallel to provide multiple products as individual compounds or mixtures. The techniques of combinatorial chemistry are becoming very popular in the pharmaceutical industry as tools to discover and optimize new drugs. In combinatorial synthesis, the premium of simple methods of purification is even higher than in normal synthesis; one cannot chromatograph hundreds or thousands of samples. For this reason, combinatorial synthesis is now conducted almost exclusively on the solid (polymeric) phase, where purification can be effected simply by filtration. Unfortunately, the purification attractions of the solid phase turn into synthetic detractions. Conducting liquid phase reactions can be difficult because the polymer never truly dissolves in the reaction solvent.

Combinatorial syntheses are usually automated. There are several features that favor the automation of organic synthesis with substrates in the liquid phase rather than on the solid phase. Four of these are briefly considered below. First, there are more phases available. Counting water as three phases (neutral, acidic, basic) provides seven different phases. There is then much more flexibility to this approach because there are more phases and more possible separations. Second, in the liquid phase approach with a fluorous reaction component, the substrate is not "affixed" in any phase, so purification of products by "phase switching" is now an option. Phase switching is simply modifying the substrate so that it preferentially partitions out of one phase and into another. Such phase switches can be envisioned between several different phases and can be accomplished at any point in a synthesis. Third, there is no need for "attachment" and "detachment" of the substrate to the solid phase. All concerns about stabilities of polymers and linkers to reaction conditions are eliminated; the only concern is the substrates. Fourth, many reactions are preferably conducted in a homogenous liquid phase. This is in direct contrast to solid phase syntheses, where true homogeneity is never obtained.

The present invention, for example, also provides substantially universal methods for synthesizing and separating organic compounds. The methods are particularly useful in combinatorial synthesis techniques, but find use in substantially any reaction and/or separation requiring separation of one organic compound from another organic compound.

The present invention thus provides generally a method of separating a first organic compound from a mixture comprising at least a second organic compound. Under this method, the first organic compound is first selectively reacted with a fluorous reaction component to attach a fluorous moiety or fluorous "phase tag" to the first organic compound to result in a fluorous compound. The first organic compound may be mixed with the second organic compound before it is selectively reacted with the fluorous reaction component. Alternatively, the second organic compound can be formed or added after formation of the fluorous compound. The fluorous moiety has a molecular weight sufficiently high to render the fluorous compound separable from the second organic compound via an organic/fluorous phase separation technique. The fluorous compound is then separated from the second organic compound via the organic/fluorous phase separation technique. Preferably, the fluorous compound is partitionable into a fluorous liquid phase to enable separation in an organic/fluorous liquid-liquid extraction. The separated fluorous compound may be reacted, if desired, to regenerate the first organic compound.

The present invention also provides generally a method of synthesizing an organic target product and separating the organic target product from other organic compounds including excess organic reaction components and/or organic byproducts. Under this method, a first organic compound is reacted with a first fluorous reaction component to attach a fluorous moiety or fluorous phase tag to the first organic compound to result in a second fluorous reaction component. The fluorous moiety comprises sufficient fluorine to render a fluorous target product produced in a reaction scheme including a single reaction or series of reactions separable via an organic/fluorous phase separation technique from excess organic reaction component(s) and/or organic byproduct(s). Preferably, the fluorous target product partitions preferentially into a fluorous liquid phase to enable separation via organic/fluorous liquid-liquid extraction.

The fluorous reaction component is reacted with at least a second organic compound/reaction component to produce the fluorous target product. One reaction with a single "second" organic compound or numerous additional reactions with other organic compounds can occur before synthesis of the fluorous target compound is complete. The fluorous target product is then separated from organic compounds including any remaining second organic compound and/or any organic byproduct via the organic/fluorous phase separation technique. The separated fluorous target product is then reacted to cleave the fluorous moiety and provide the organic target product. The "fluorous phase tagging" reaction/separation methods are equally useful in reactions occurring in an organic/fluorous biphasic mixture and in reactions occurring in a organic/fluorous solubilizing liquid phase.

The present invention also provides chemical compounds of Si, Ge and Sn that are well suited for use as fluorous reaction components and/or fluorous phase tags. In that regard, the present invention provides generally a chemical compound of the formula

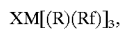

wherein M is Si, Ge or Sn. X is H, F, Cl, Br, I, $N_3$, $OR^1$, OH, OOH, $OOR^1$ $SR^1$, $SeR^1$, CN, NC, $NR^1R^2$, a cyclic group (for example, an aryl group), a substituted cyclic group (for example, a substituted aryl group), a heterocyclic group (for example, a heteroaryl group), or a substituted heterocyclic group (for example, a substituted heteroaryl group). Such cyclic groups are preferably of 5 to 25 carbon atoms.

X may also be a linear or branched alkyl group of 1 to 15 carbons. In the case that M is Sn or Ge, the linear or branched alkyl group is preferably of 3 to 15 carbons. Further, X may be a substituted linear or branched alkyl group, an alkenyl group, a substituted alkenyl group, an alkynyl group, a substituted alkynyl, an acyl group, or a substituted acyl group. These groups preferably are of 1 to 20 carbon atoms.

X may also be M'((R')(Rf'))$_3$, OM'((R')(Rf'))$_3$ or OOM' ((R')Rf')$_3$, wherein M' is Si, Ge, or Sn. $R^1$ and $R^2$ are each independently, the same or different, H, a linear or branched alkyl group, a substituted linear or branched alkyl group, a cyclic alkyl group, a substituted cyclic alkyl group, an alkylsulfonyloxy group, a perfluoroalkylsulfonyloxy group, an acyl group, a substituted acyl group, or a perfluoroacyloxy group. R and R' are each independently, the same or different, an alkylene group of 1 to 6 carbons or a substituted alkylene group of 1 to 6 carbon atoms. Rf and Rf' are each independently, the same or different, a linear perfluoroalkyl group of 3 to 20 carbons, a branched perfluoroalkyl group of 3 to 20 carbons, or a hydrofluoroalkyl group of 3 to 20 carbons, wherein the hydrofluoroalkyl group comprises up to one hydrogen atom for each two fluorine atoms thereof.

The terms "alkyl", "aryl" and other groups refer generally to both unsubstituted and substituted groups unless specified to the contrary. Alkyl can be saturated or unsaturated and branched or unbranched. Preferred substituents of substituted groups include but are not limited to groups containing C, H, Cl, F, Br, I, N, S, P, As or Si. The term "alkylene" refers to an acyclic carbon chain or a saturated acyclic carbon chain represented by the formula —$C_nH_{2n}$— (for example, —$CH_2CH_2$—), wherein hydrogen may be replaced by a monovalent substituent.

In a number of preferred embodiments wherein M is Sn, X is preferably H, F, Cl, Br, I, $N_3$, OH, $OSn(CH_2CH_2Rf)_3$, an allyl group, a phenyl group, a 4-methoxyphenyl group, a 2-pyridyl group or a 2-furyl group.

R is a preferably a linear alkylene group of 1 to 5 carbons. Rf is a preferably a linear perfluoroalkyl chain of 6 to 12 carbons. In general, the larger the molecule to be made fluorous (that is, the higher the molecular weight) the greater the fluorine content required.

In general, the present invention provides compounds that are fluorous analogs of standard Sn, Ge and Si compounds. Standard organometallic reaction components and reactions are reviewed in Davis, A., ed., *Comprehensive Organometallic Chemistry II*, Pergamon Press, Oxford, Vol. 2, 217–304 (1995).

DETAILED DESCRIPTION OF THE INVENTION

Figure 1:
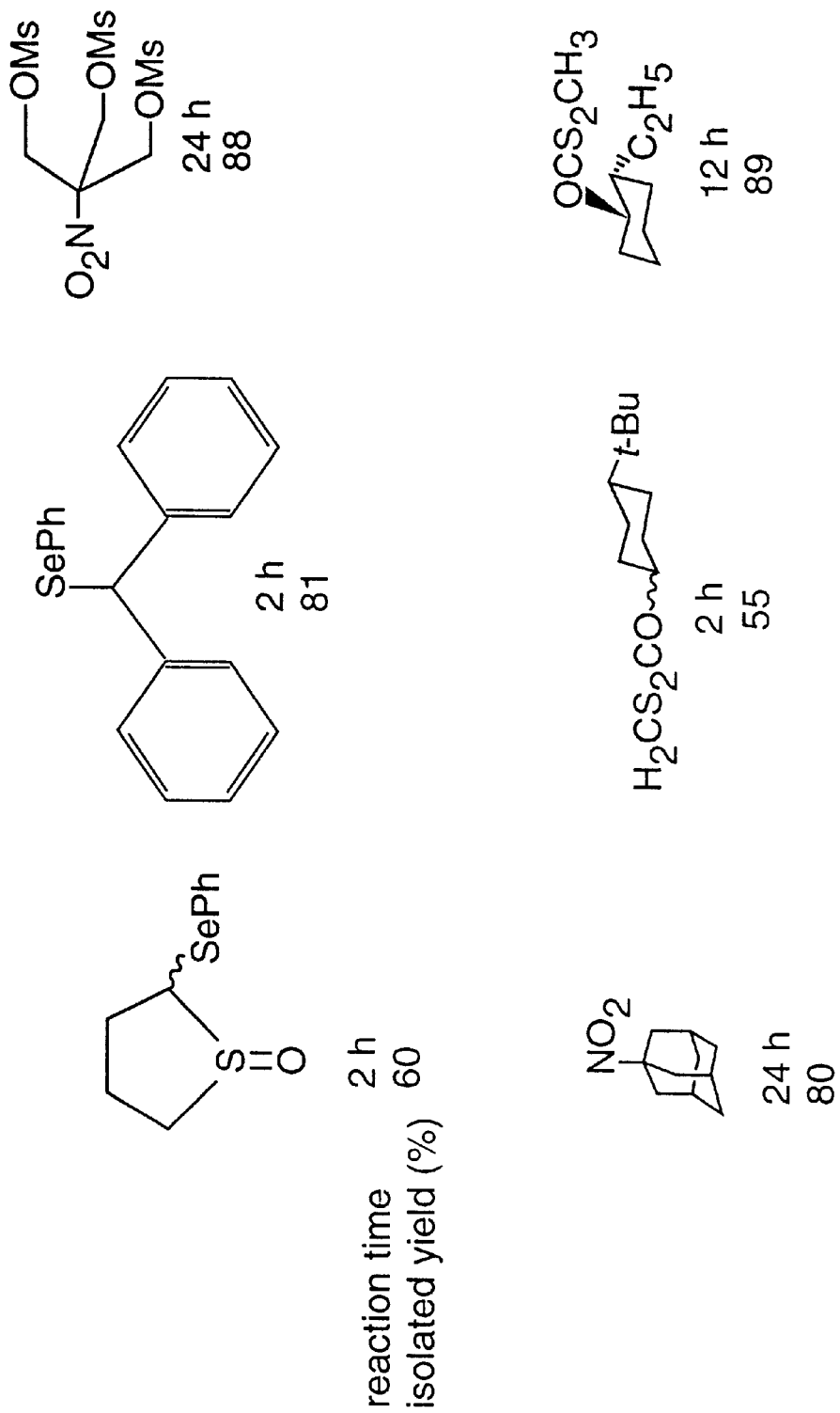
FIG. 1 illustrates organic substrates reduced with a novel fluorous reagent.

1. Synthesis In An Organic/Fluorous Solubilizing Liquid Phase

Synthesis in an organic/fluorous solubilizing liquid phase under the present invention will be discussed in connection with several examples of novel fluorous synthetic schemes using reaction components (that is, reactants, reagents, and catalysts) of the general formula:

$$XM((R) (Rf))_3$$

In this general formula Rf is a fluorous group and, preferably, a perfluorinated group having 3–20 carbons $(XM[(R)_d(Rf)_e])_z$; wherein d=e=1 and z=3). (R) is a hydrocarbon group and, preferably, a $—CH_2CH_2—$ group. M is selected from the group consisting of silicon, germanium and tin. X is an atom or a group that is involved in a reaction with an organic substrate. These reaction components are used in a number of different ways to synthesize and purify organic molecules, as outlined below.

Reactions of organic substrates with fluorous reagents to provide organic target products In this synthetic scheme, an organic substrate was reacted with a fluorous reagent of the general formula $XM((R)(Rf))_3$, which can be used in excess if desired. After reaction in an organic/fluorous solubilizing liquid phase, organic-fluorous extraction/separation upon addition of an appropriate co-solvent provides the target product in the organic liquid phase, and the excess fluorous reagent and the products derived therefrom in the fluorous liquid phase. The method not only facilitates purification of the target product relative to existing methods, but it also allows ready recovery of a fluorous side product in a state suitable for recycling to the original reagent for reuse. In some cases, the original reagent is recovered directly. Thus, both purification and disposal costs are reduced.

In one study, a fluorous reagent, tris (2-(perfluorohexyl) ethyl)tin hydride 3 $[(C_6F_{13}CH_2CH_2)_3SnH]$ was synthesized. The approved name of fluorous tin hydride reagent 3 is tris (3,3,4,4,5,5,6,6,7,7,8,8,8-tridecafluorooctyl)tin hydride. It has been discovered that this reagent behaves very similarly to "standard" (that is, nonfluorous) tin hydride reagents in radical reductions, yet it has significant practical (and possibly also ecological) advantages over the commonly used compounds, tributyltin hydride, tris(trimethylsilyl)silicon hydride, and related reagents. In the reactions studied, a hybrid organic/fluorous solvent comprising benzotrifluoride (BTF, $C_6H_5CF_3$, trifluoromethyltoluene) or benzotrifluoride mixed with tert-butanol, was used to provide a homogeneous reaction medium or phase (the organic/fluorous solubilizing liquid phase). Homogeneous liquid phase solvents comprising mixtures of organic and fluorous solvents are known and can also be used in the reactions of the present invention. Organic solvents in which the fluorous reagent is substantially soluble (for example, hexane, THF and/or ether) can also be used. Benzotrifluoride (BTF) was selected in part because of its favorable properties and low cost.

The equation below summarizes a preferred method for preparing novel fluorous tin hydride reagent 3. Preparation of the Grignard reagent from 2-perfluorohexyl-1-iodoethane and quenching with phenyltrichlorotin provided the novel intermediate product 1a. Brominolysis of the phenyl-tin bond and reduction of the resulting novel tin bromide 2 with lithium aluminum hydride in ether provided novel fluorous tin hydride reagent 3. This product was isolated in 82% overall yield as a clear liquid after purification by vacuum distillation.

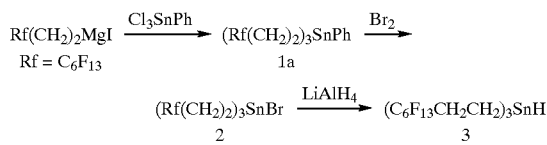

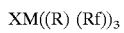

Attempts to reduce a typical organic substrate, 1-bromoadamantane, using fluorous tin hydride reagent 3 under fluorous conditions like those used by Zhu resulted in unacceptably slow reaction rates and unacceptably low yields. Similarly, attempts under fluorous biphasic conditions like those used by Horvath and Rabai or in normal organic solvents like benzene also resulted in unacceptably slow reaction rates and unacceptably low yields. It is believed that the partition coefficients for the reaction components are such that the phase separation prevents a radical chain from propagating with bromoadamantane. Simple extractions provide crude estimates of partition coefficients. Fluorous tin hydride reagent 3 (1.0 g) was partitioned between PFMC (10 mL) and an organic solvent (10 ml) by shaking for 5 min in a separatory funnel. Evaporation of the organic layer provided the following weights: benzene, 22 mg; MeOH, 30 mg; $CH_2Cl_2$, 47 mg; EtOAc, 104 mg; $CHCl_3$, 141 mg.

In contrast, treatment of perfluorodecyl iodide with 1.2 equiv of fluorous tin hydride reagent 3 and 10% AIBN in refluxing PFMC provided the corresponding reduced compound 4 in 72% yield as illustrated in the equation below. The success of this fully fluorous reaction (that is, fluorous solvent, fluorous reagent, fluorous substrate and fluorous product) suggested that a homogeneous medium was important thereto.

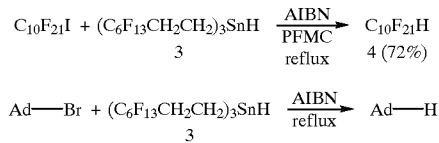

Adamantyl bromide was cleanly reduced over approximately 3 hours with 1.2 equiv of fluorous tin hydride reagent 3 in refluxing BTF (stoichiometric procedure). After evaporation of the BTF and liquid-liquid extraction (PFMC-$CH_2Cl_2$) to separate the tin products, adamantane was isolated in 90% yield (as determined by GC integration). Under the stoichiometric procedure, fluorous tin hydride reagent 3 reduces a number of other functional groups besides halides, as shown in FIG. 1. In these substrates, the nitro, phenylseleno, or xanthate groups are replaced by hydrogen.

A catalytic procedure was also developed by using 10% fluorous tin hydride reagent 3 and 1.3 equiv of $NaCNBH_3$ in a 1/1 mixture of BTF and tert-butanol at reflux. This procedure is analogous to the "standard" reaction developed by Stork for nonfluorous tin hydrides. Stork, G. and Sher, P. M., J. Am. Chem. Soc., 108, 303 (1986). After approximately 3 hours, the reduction of 1-bromoadamantane was complete. After evaporation, the products were isolated by partitioning between three liquid phases: water removes the inorganic salts, methylene chloride extracts the adamantane (isolated in 92% yield), and perfluoromethylcyclohexane extracts the tin products. Analyses by $^1H$ NMR and $^{19}F$ NMR (estimated detection limit 1–2%) failed to detect any fluorinated products in the residue from the methylene chloride phase, and likewise no adamantane was detected in the fluorous extract. The residue from the fluorous extract was reused five times to reduce bromoadamantane by this catalytic procedure with no decrease in yield. In separate experiments, successful reductions of 1-bromoadamantane were observed with as little as 1% of the fluorous tin hydride reagent 3. A control experiment showed that 1-bromoadamantane was not reduced by $NaCNBH_3$ alone under these conditions over approximately 24 hours.

Synthetic chemists have long lauded the ionic and radical reactivity profile of tributyltin hydride, but bemoaned its separation and toxicity problems. The results of the present studies indicate that fluorous tin hydride reagent 3 retains the laudable reactivity profile of tributyltin hydride. However, fluorous tin hydride reagent 3 can be separated from organic products by liquid-liquid extraction. The ability to use fluorous tin hydride reagent 3 in catalytic amounts and to repeatedly reuse the fluorous residue indicates that large scale applications of fluorous tin hydride reagent 3 or a suitable relative are practical because it is not necessary to synthesize or to dispose of large quantities of tin. A family of related tin reagents can provide similar practical benefits for other important organotin reactions. A review of non-fluorous (standard) tin reactions is provided in Pereyre, M.; Quintard, J. P. and Rahm, A., Tin in organic Synthesis, Butterworths: London; (1986).

Figure 2A:
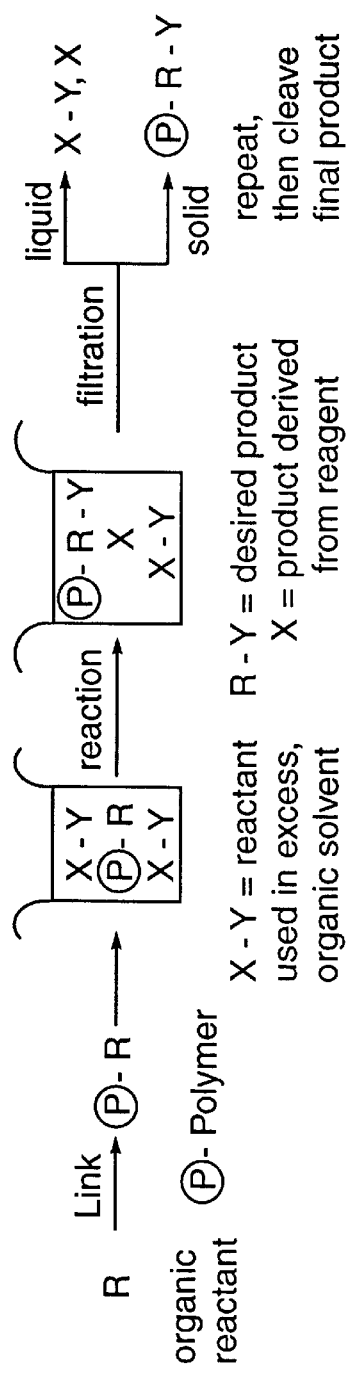
FIG. 2A illustrates a current combinatorial synthetic scheme.
Figure 2B:
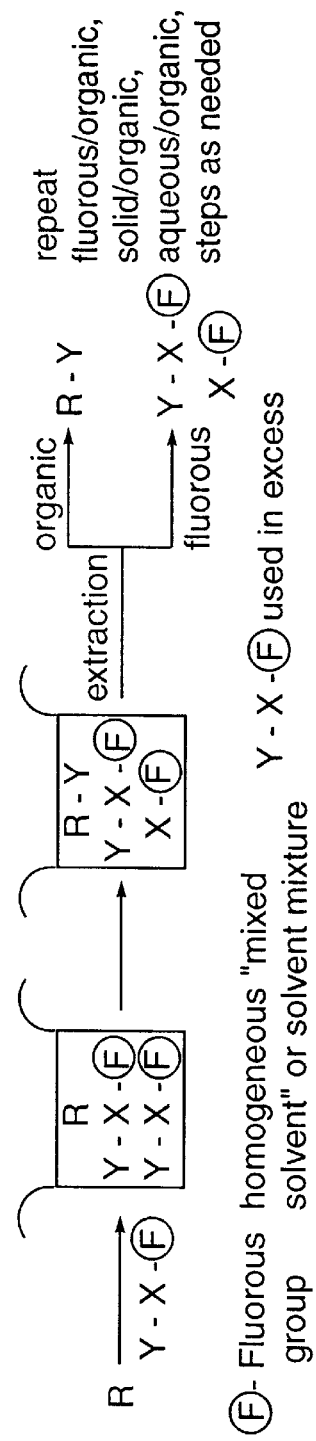
FIG. 2B illustrates an embodiment of a combinatorial synthetic scheme of the present invention.

Fluorous reagents such as fluorous tin hydride reagent 3 also have important applications in combinatorial synthesis. Most current combinatorial synthetic strategies place the substrate on a polymeric solid phase (P) (see FIG. 2A) so that it can be separated from other compounds in the reaction mixture by the phase separation technique of filtration. However, there are a number of synthetic advantages to combinatorial strategies that place the substrate in the organic liquid phase, especially for syntheses of relatively small libraries (for example, tens to hundreds of compounds) Fluorous reagents provide new options for these types of syntheses because fluorous reagents and the substrates (organic soluble) can be separated by the phase separation technique of extraction. See FIG. 2B.

Figure 3:
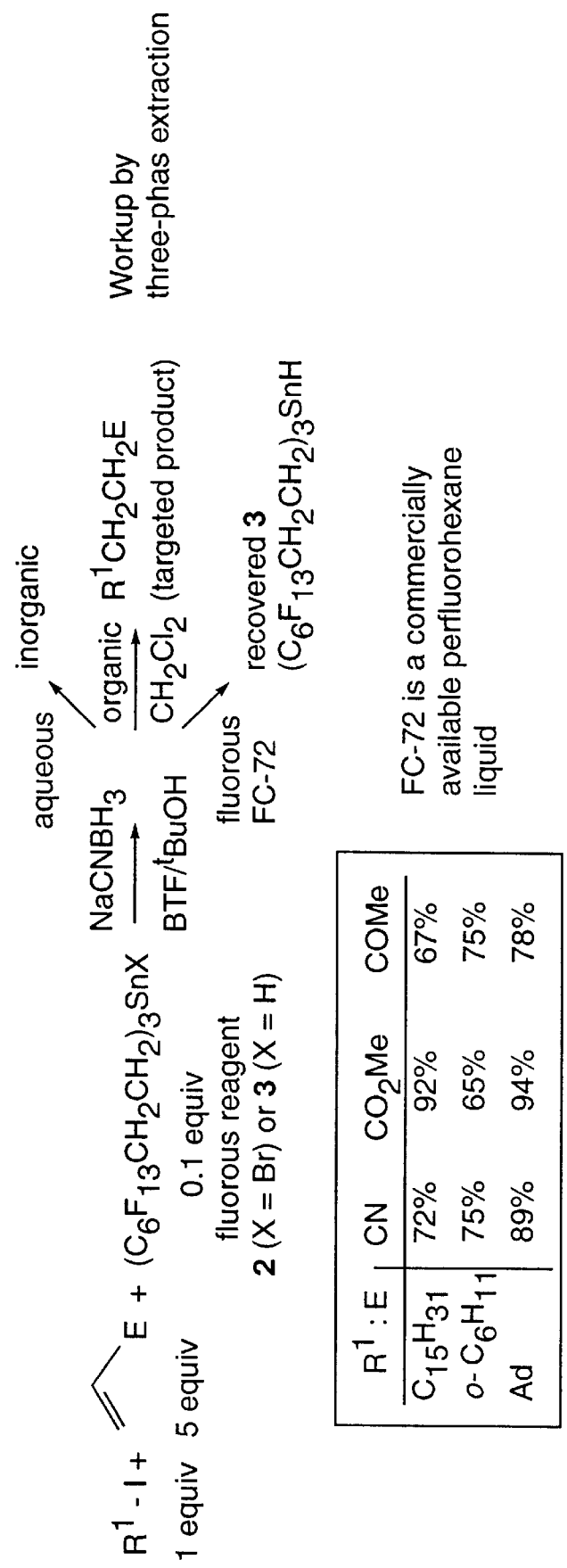
FIG. 3 illustrates the results of a combinatorial synthesis under the present invention.

To illustrate the possibilities, a "fluorous/organic" step was simulated in a homogeneous liquid phase combinatorial synthesis by conducting a series of radical additions in parallel. The results are illustrated in FIG. 3. Three halides were crossed with three alkenes, and reductions were conducted simultaneously in nine individual vials under the catalytic procedure. The nine products were "purified" by three-phase liquid-liquid extraction (conducted in the original reaction vial) and evaporation. Yields were then determined by recording NMR spectra in the presence of an internal standard. The crude products were quite pure (no significant starting materials or side products as assayed by capillary GC), and could hypothetically be used directly in the next step of a sequence. Automation of the extractions will make more parallel reactions possible.

Combinatorial synthesis with substrates in the organic liquid phase can already be conducted without chromatography if all the other reagents are volatile, water soluble, or on a solid phase. In the case of fluorous reagents, the possibilities for liquid phase combinatorial synthesis in a spatially separated mode are greatly expanded. Like filtration, the phase separation techniques of extraction and evaporation also allow ready separation of components, so excesses of reagents can be used. The pairing of organic substrates with fluorous reagents is expected to be especially important since a full range of traditional (including anhydrous) reactions can be conducted under homogenous liquid phase conditions, yet the products and reagents can still be separated by extraction. In short, the detractions to synthesis posed by phase separation can be divorced from its advantages in purification.

Reactions of organic substrates with fluorous reactants to provide organic target products The features of this synthetic scheme are similar to those described above, except that a fluorous reactant reacts with an organic reaction component. The method of the present invention is illustrated with a combinatorial Stille coupling in FIG. 4B. A standard Stille coupling is illustrated in FIG. 4A.

Figure 4A:
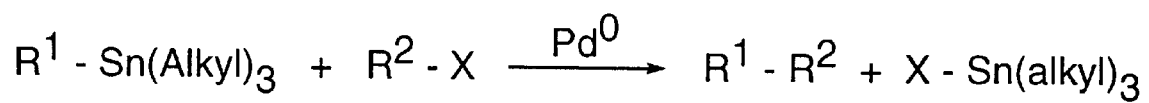
FIG. 4A illustrates a standard Stille coupling.

The standard Stille reaction as illustrated in FIG. 4A is an important member of a family of transition metal catalyzed cross coupling reactions that is regularly used in modern organic synthesis, and it has recently been extended to solid phase combinatorial synthesis. Stille, J. K., Angew. Chem. Int. Ed. Engl., 25, 508 (1986); Mitchell, T. N., Synthesis, 803 (1992); Deshpande, M. S., Tetrahedron Lett., 35, 5613 (1994). The characteristic feature of the standard Stille reaction is that one of the coupling partners is a trialkylorganotin compound (see FIG. 4A). The alkyl substituents are almost always methyl or butyl groups. The Stille reaction is popular because the tin reagents are relatively air and moisture stable, can be easily synthesized and purified, and tolerate a wide variety of both protected and unprotected functional groups. After the Stille reaction, the tin becomes a liability: trimethyltin byproducts are easy to remove but toxic, while tributyltin compounds are less toxic but difficult to remove.

The present inventors have discovered that compounds of the general structure $ArSn(CH_2CH_2C_6F_{13})_3$ participate in representative Stille couplings to make biaryls and diarylmethanes, and that all the advantages of the fluorous synthetic scheme of the present invention are exhibited. The present studies teach new options for the emerging field of liquid-phase combinatorial synthesis.

Fluorous phenyl tin reactant 1a served as one of the reactants for a Stille coupling. Brominolysis of 1a as described above provided the tin bromide 2, which served as the precursor for preparing the p-methoxyphenyl- (1b), 2-furyl-(1c) and 2-pyridyl-(1d) fluorous tin reactants by standard reactions with either aryllithium or aryl Grignard reagents.

Figure 4B:
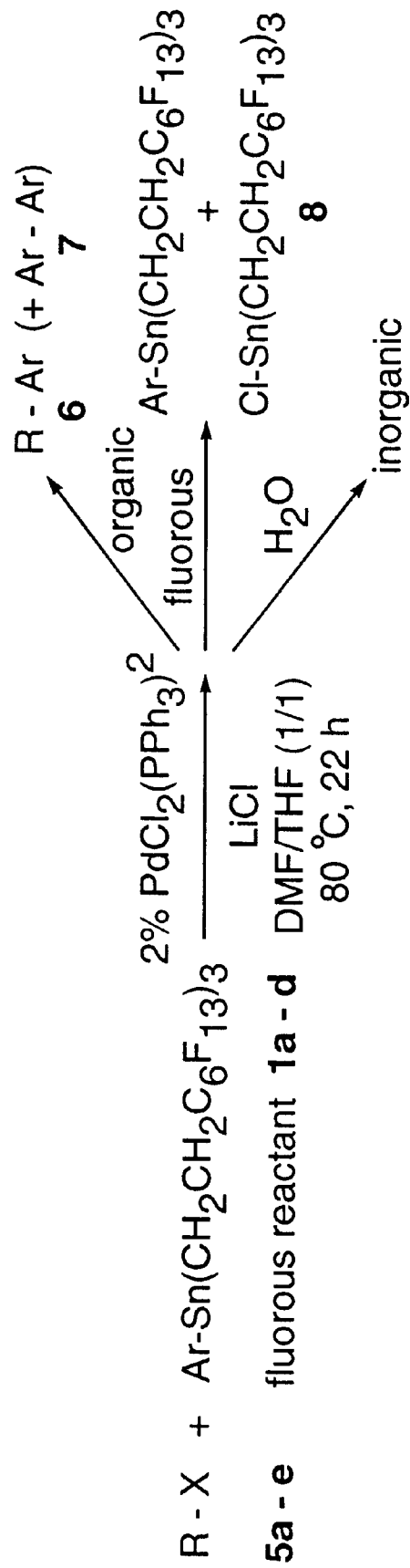
FIG. 4B illustrates a Stille coupling under the present invention.

Stille reactions were conducted under the standard set of conditions illustrated in FIG. 4B. These conditions were selected based on a number of trial experiments with fluorous aryl tin reactants 1a–d. Because Stille reactions are not generally conducted under biphasic conditions, a solvent system that substantially solubilized both the organic substrate and the fluorous tin reactant and that provided clean transformations within a reasonable time frame was used. DMF and THF were both useful, but reactions were rather slow (approximately 2 days). Solvents comprising equal parts of DMF/THF and solvents comprising equal parts of $DMF/C_6H_5CF_3$ both provided homogeneous liquid phase reactions (as determined by observation) and reasonable reaction rates (<22 hours) at 80° C. The DMF/THF mixture (1/1) was selected for the standard experiments.

A mixture of 1.2 equiv fluorous tin reactant (1a–d), 1 equiv halide or triflate (5a–e, 0.2 mmol), 2% $PdCl_2(PPh_3)_2$, and 3 equiv of LiCl in 1/1 DMF/THF (1 mL) was heated at 80° C. Reactions were conducted in individual vessels in groups of five (one tin reagent with all five partners). After approximately 22 hours, each mixture was evaporated to remove some of the solvent and then was partitioned in a three-phase extraction between water (top), dichloromethane (middle) and FC-72 (bottom). Evaporation of the FC-72 phase provided fluorous tin chloride 8 $(C_6F_{13}CH_2CH_2)_3SnCl$ (80–90%). Most of the residual 10–20% fluorous tin chloride 8 remained in the organic phase. If desired, the residual amount can be removed by washing with FC-72. Recovered fluorous tin chloride 8 was routinely recycled. Evaporation of the organic phase provided a crude organic product that was further purified by preparative TLC to provide major cross-coupled biaryl or diarylmethane 6 along with small amounts of symmetrical biaryl 7 (5–10%) derived from the tin reactant. The symmetrical biaryl is a common byproduct in standard Stille couplings.

Figure 4C:
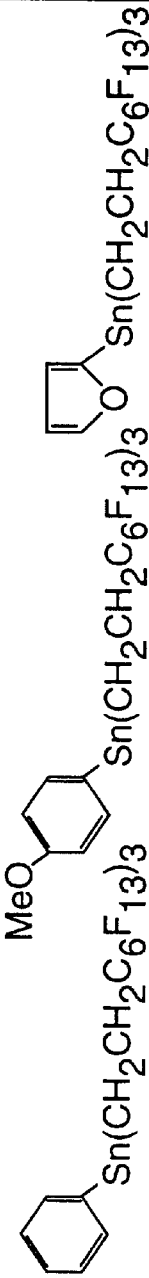
FIG. 4C illustrates several examples of Stille couplings under the present invention with yields.

Yields for the cross-coupled products are shown in FIG. 4C for fluorous tin reactants 1a–c. These reactants gave very clean crude products, and isolated yields of target product 6 were generally high (>80%), except for a few cases with the furyl tin reagents where the products are somewhat volatile. As in the case of the standard Stille coupling of 2-pyridyltributyltin reagent, the five crude products from the pyridyl tin reagent 1d were not very clean, so these reaction mixtures were not fully purified. See Gronowitz, S. et al., *J. of Organometallic Chem.*, 460, 127 (1993) Significant amounts of cross-coupled products (estimated 25 to 50%) were produced with p-nitrophenyl triflate and bromide and with iodobenzene; however, yields of pure products were not determined.

A preparative reaction was conducted with 0.40 g of p-bromonitrobenzene (2 mmol) and 2.97 g of phenyltin reactant 1a (2.4 mmol) in 10 mL of 1/1 DMF/THF at 80° C. for approximately 22 hours. Both reactants were consumed according to TLC analysis. After azeotropic evaporation with toluene at 75° C. (to remove some of the solvent), a three-phase extraction was conducted as described above. The methylene chloride phase was then washed three more times with water and FC-72 (together) to remove DMF and fluorous products. The crude organic product was purified by flash chromatography to provide 337 mg (85%) of 4-nitrobiphenyl and 17 mg (5%) of biphenyl. The crude fluorous tin chloride (99%) from the FC-72 phase was reacted with phenyl magnesium bromide to provide 2.85 g (96% overall) of the original tin reactant 1a after purification by passing through a short column of neutral alumina.

The success of the Stille reaction coupled with the prior radical and ionic reactions of the analogous tin hydride indicates that rendering other tin reactants fluorous can be a general strategy to make the vast repertoire of organotin chemistry more practical and more environmentally friendly.

2. Fluorous Phase Tagging In Synthesis And Separation

The techniques discussed below rely on the ability to render an organic molecule fluorous by addition of a "fluorous phase tag" or "fluorous tag". The fluorous-tagged organic molecule is separable from organic (non-fluorous) molecules via an organic/fluorous phase separation technique. For example, the fluorous-tagged molecule may partition preferentially into the fluorous liquid phase in a fluorous/organic liquid-liquid extraction. The techniques provide simple methods to separate organic molecules based on the presence or absence of a fluorous tag.

Figure 5:
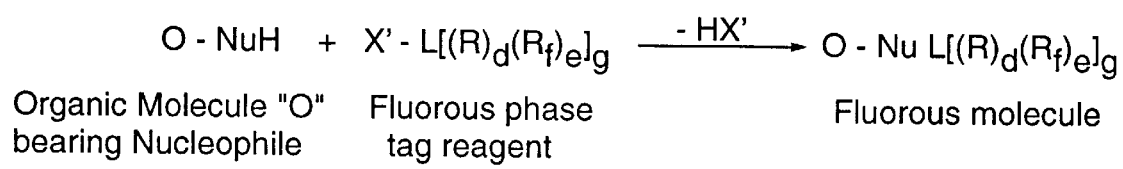
FIG. 5 illustrates a phase tagging scheme.

As illustrated in FIG. 5, an organic molecule O (or a library of organic molecules) bearing nucleophile Nu is attached to a fluorous phase tag $L[(R)_d(Rf)_e]_g$ through the intermediacy of a standard organic reaction with an organic molecule and a fluorous tagging reagent. FIG. 5 illustrates this attachment via a nucleophilic substitution reaction. This illustration is, however, only for the purposes of example. Many other types of standard reactions can be used. In some cases, the fluorous tag itself and the tagging process can serve as a fluorous analog to existing "standard" (that is, non-fluorous) protecting groups. Illustrative standard protecting groups may be found, for example, in Greene, T. W. and Wuts, P. G. M., *Protective in Groups in Organic Synthesis,* Wiley-Interscience: New York, (1991). The fluorous tagging method of the present invention is not limited to this design, however. For example, in another strategy, the fluorous tag can be a surrogate for another atom or group in the final product.

The fluorous phase tag, $L[(R)_d(Rf)_e]_g$, comprises a linker L that bridges a fluorous moiety (or moieties) $(R)_d(Rf)_e$ (wherein R, Rf, d and e are as described above; and g is an integer greater than or equal to one) to organic molecule O. In some cases, it may be desirable to have more than one tag per molecule, and these tags may be the same or different. R can be present or absent as described above. Linker L can likewise be present or absent, but its presence is often preferable because it provides a ready means of attachment and detachment of the fluorous tag. The linker L can be any standard atom or functional group, either organic or fluorous, that preferably can be attached and detached (if necessary) under standard reaction conditions.

Reactions of fluorous substrates with organic reactants to provide fluorous target products This synthetic scheme provides, for example, an alternative to the now common use of polymers in large molecule synthesis and combinatorial chemistry. The method of the present invention has the advantage over such solid phase techniques of allowing the routine use of standard liquid phase reagents and reaction conditions.

To begin a synthesis, an organic substrate is rendered fluorous by attachment to a fluorous group (for example, a silyl or a stannyl group) that acts as a fluorous phase tag. A reaction or sequence of reactions is then conducted in which the products are purified by, for example, phase separation techniques including liquid-liquid extraction (for organic or water soluble reagents, reactants, impurities), filtration (for polymeric or solid reagents, reactants, impurities) or evaporation (for volatile reagents, reactants, impurities). At the end of the synthesis, the target organic product is released from the fluorous tag, and then separated from all fluorous products by, for example, organic/fluorous liquid-liquid extraction or filtration, if the target product is a solid.

Figure 6:
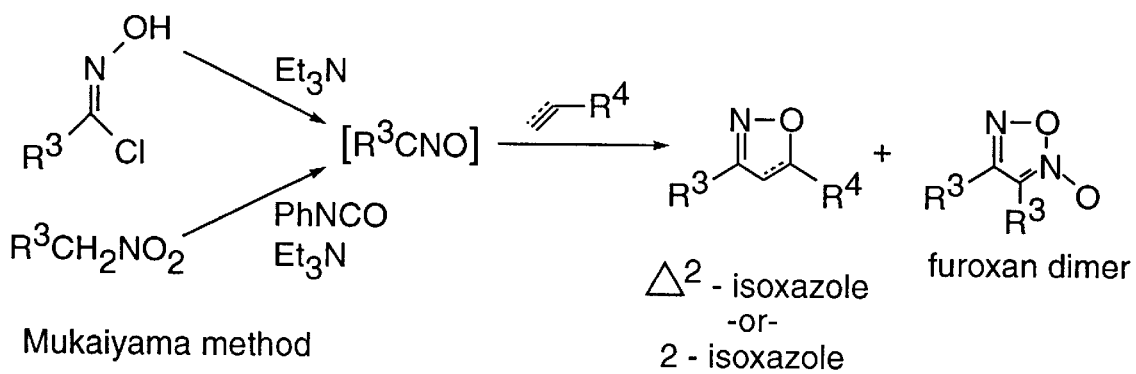
FIG. 6 illustrates in situ method of nitrile oxide generation and cycloaddition.

As a test reaction for fluorous liquid phase synthesis, nitrile oxide cycloadditions to fluorous-tagged derivatives of simple unsaturated alcohols were chosen. These reactions occur in high yields with terminal alkenes and alkynes and an interesting class of heterocycles is produced. Nitrile oxide cycloadditions provide a good test reaction because there are two common ways to produce nitrile oxides that use different reagents and thus provide differing purification challenges. These two methods—the Huisgen method and the Mukaiyama method—are summarized in FIG. 6. See Carmella, P. and Grünanger, P., 1,3-*Dipolar Cycloaddition Chemistry,* Wiley-Interscience, New York, Vol. 1, 291 (1984). If the nitrile oxide precursor is used in excess, both methods require that the product be separated from the nitrile oxide dimer (a furoxan). Purification of reaction mixtures from the more popular Mukaiyama method is especially challenging because the two reagents ($R^3CH_2NO_2$ and PhNCO), the furoxan dimer, and obligatory sym-diphenyl urea (PhNHCONHPh) byproduct are all organic compounds. Chromatographic procedures for separation are usually used.

Figure 7:
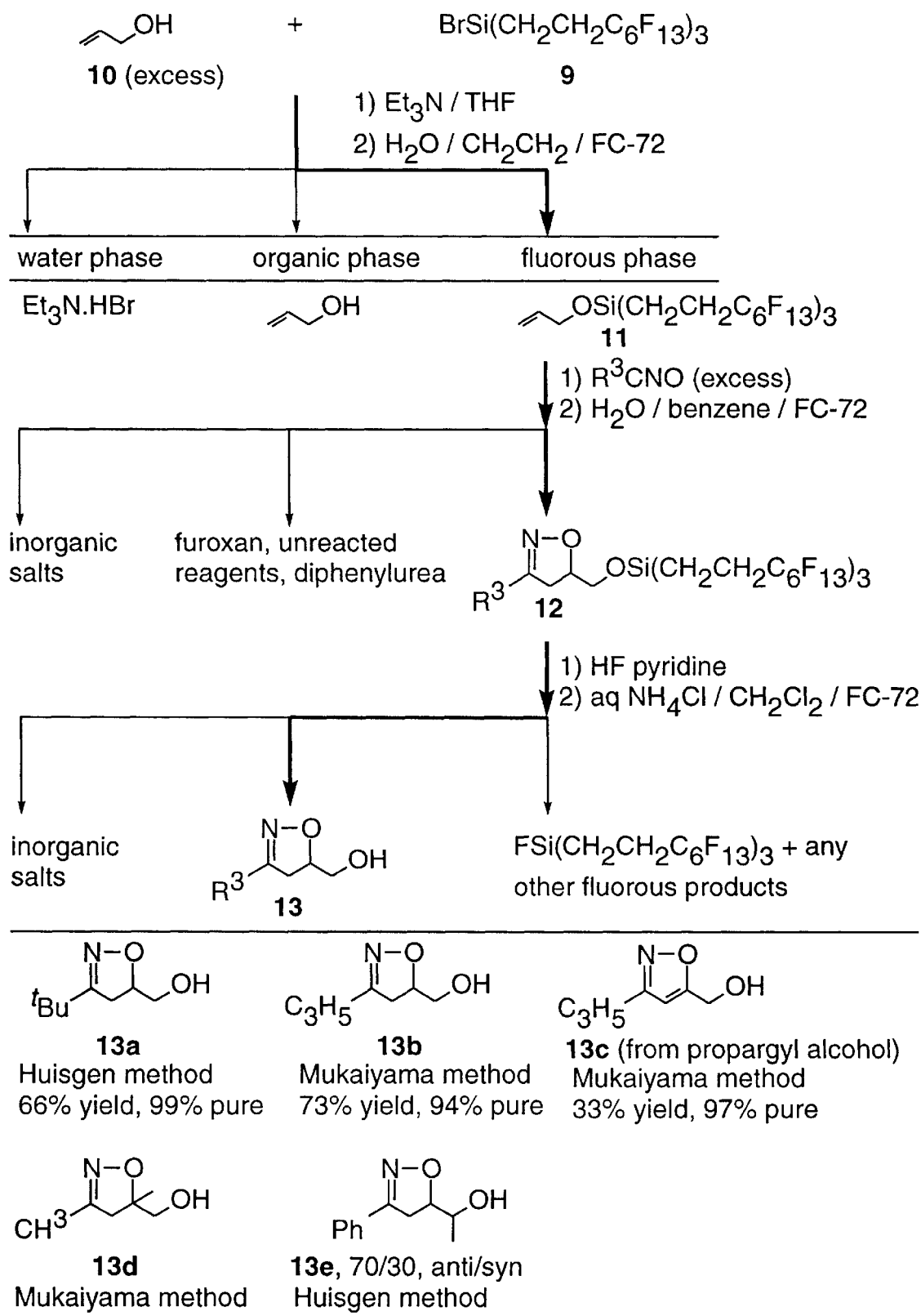
FIG. 7 illustrates nitrile oxide cycloaddition with fluorous-tagged allyl alcohols.

A protocol for the nitrile oxide cycloaddition reactions is shown in FIG. 7, using allyl alcohol as an example. Five examples of the overall process (without intermediate chromatography or characterization) as designed for combinatorial synthesis are described herein. Additional examples of the overall process with intermediate chromatography and characterization are included in the Experimental Examples set forth below. The phase tagging reagent 9 was designed as a fluorous analog of the popular trialkylsilyl class of protecting groups that is commonly used in organic synthesis, and it is readily available on a multi-gram scale. For phase tagging reagent 9, Br is a leaving group for the purpose of attachment to an organic molecule. Linker L is Si; R is $CH_2CH_2$; d is 1; Rf is $C_6F_{13}$; e is 1; and g is 3.

Silylation of allyl alcohol was performed by using excess alcohol 10 (2–4 equiv) in THF under standard conditions. Workup and purification included evaporation and a three-phase liquid extraction with water (top), $CH_2Cl_2$ (middle), and FC-72 (bottom). The organic phase containing the unreacted alcohol and the water phase containing the amine hydrobromide (and probably also some alcohol in the case of these substrates) were discarded, and the fluorous phase was concentrated to provide the desired fluorous-tagged silyl ether 11. At this stage, the strategy allows for ready separation of unreacted organic substrates 10 from tagged products 11 as demonstrated by the intentional use of excess alcohol. In the case of some or all low molecular weight alcohols, the excess alcohol was removed at the evaporation stage.

Nitrile oxide cycloadditions were then conducted under standard Mukaiyama ($R^3$=Pr and Me) or Huisgen ($R^3$=$^t$Bu or Ph) conditions. To mimic the need to drive reactions to completion and to deliberately generate impurities for separation, all the reagents were used in four- to tenfold excesses. The Huisgen reactions were conducted in $CH_2Cl_2$, a solvent in which the fluorous substrates 11 were not completely soluble (as determined by the naked eye) while the Mukaiyama reactions were conducted in benzotrifluoride (trifluoromethylbenzene, $C_6H_5CF_3$), a solvent in which the substrates 11 appear to fully dissolve. After the reactions, three-phase extractions were conducted as described above except this time the organic extraction solvent was benzene. The water (middle) and organic (top) phases were again discarded, and the evaporation of the fluorous phase (bottom) then provided the cycloadducts 12 substantially free from organic (and inorganic) impurities.

The fluorous tag was then removed by desilylation of the products 12 with HF.pyridine in $Et_2O$ at room temperature. After removal of the fluorous tag, the organic phase contained the desired product in a final three-phase extraction between aqueous ammonium chloride (top), $CH_2Cl_2$ (middle), and FC-72 (bottom). Evaporation of the $CH_2Cl_2$ phase then provided the final products 13, which were analyzed for yield and purity without any additional purification. The whole sequence proceeded without crystallization or chromatography, and overall isolated yields of 13a–e for the three step sequence are shown under each of the final products in FIG. 7. The isolated yields are reasonable (in the case of 13d, material loss due to evaporation contributes to a lower yield) and the GC purities are quite good, especially considering that the deliberate stoichiometry mistakes generated large amounts of byproducts. Interestingly, the anti/syn ratio obtained in 13e is virtually identical to the ratio obtained in nitrile oxide cycloadditions with normal (non-fluorous) trialkylsilyl ethers. See Houk, K. N., et al., *J. Am. Chem. Soc.,* 106, 3880–82 (1984).

This one-step synthesis (not including attachment and detachment of the phase tag) clearly illustrates the potential for single-step and multi-step fluorous-phase synthesis. The vast majority of the existing reagents and reactants that are used in organic synthesis as well as the byproducts that these reagents and reactants produce are organic or inorganic molecules. Tagging a substrate as fluorous differentiates (that is, renders relatively easily separable) the tagged substrate and all its subsequent products (until the tag is removed) from anything else that is added to the reaction.

This tagging strategy provides a number of important advantages over the technique of linking organic molecules to polymers. First, it is difficult to envision a more robust tag than a perfluorocarbon segment Rf. Perfluorocarbons are among the most stable compounds of carbon that are known (See Hudlicky, supra). Although the linker L and the group R (if present) will not necessarily be as stable as fluorous segment Rf, the linker requirements in liquid phase synthesis are not as stringent as in solid phase synthesis. Indeed, the fluorous tags of the present invention can often be viewed as analogous to traditional organic protecting groups. Under this view, the fluorous tags function as groups that both protect functionality and serve to alter the phase preference of the molecule. Thus, tags designed to double as protecting groups are a valuable asset in a sequence of synthetic steps. In contrast, the linkers and polymers used in solid phase synthesis are assets in purification, but are frequently liabilities in the actual synthetic steps.

As in solid phase synthesis, excess reagents and reactants can be used to drive the reaction to completion based on the substrate since the phase of the substrates is different from the phase of the reactants and reagents. Indeed, it is crucial that the substrate be completely consumed since the substrate has the same phase as the product and therefore cannot be separated from it by a phase separation technique. Herein lies the Achilles Heel of all "one-phase" techniques: the phases of the substrate, the desired product derived from the substrate, and any byproducts derived from the substrate are the same. Thus, these compounds cannot normally be separated by a simple phase separation technique. "One phase" techniques do not address the larger separation problem in reactions that do not occur in quantitative or near-quantitative yield based on substrate. Thus combinatorial synthesis is limited because general classes of reactions that occur in quantitative yield on a diverse collection of substrates are still the exception rather than the rule.

Phase Switching Separations Using Fluorous-Tagged Molecules

The present inventors have discovered that a solution to this problem is to conduct a selective "organic/fluorous phase switch". In this process, the phase of one product (or a subset of products) is temporarily changed so that it can be separated from other products of the same phase. After the separation, the phase of the altered product may be switched back, such that it is returned to its original phase.

So-called acid/base extractions are an example of a "phase switch". For example, organic amines can be separated from other organic compounds by extraction into acid (phase switches from organic to water) followed by neutralization, which returns the amines to the organic phase. Unfortunately, the switch that pKa provides is not sufficiently general. In that regard, many classes of organic compounds cannot be extracted into water at any pH where they are stable.

Figure 8:
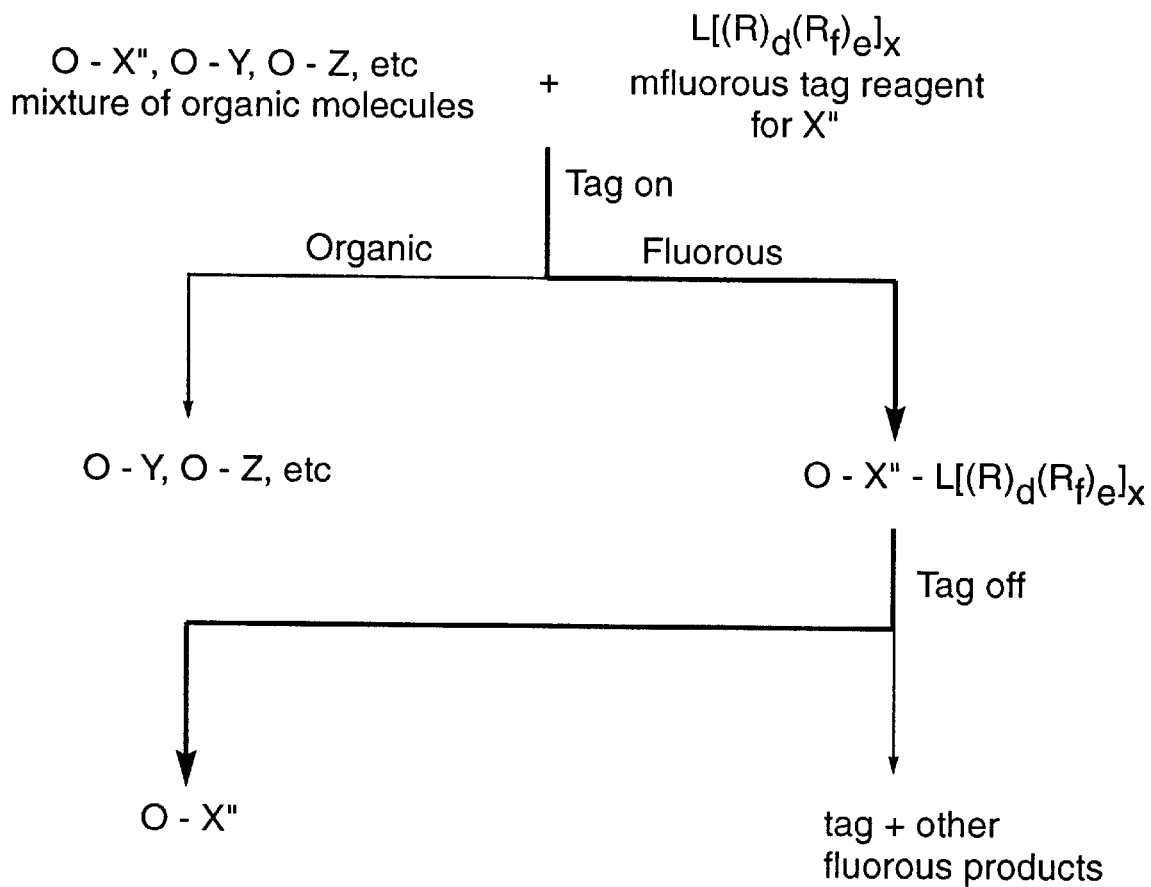
FIG. 8 illustrates schematically an example of fluorous phase switching.

It has been discovered that organic/fluorous phase switches are a substantially general and powerful method to purify organic reactions or mixtures of organic compounds. The trigger for the switch is the selective reaction of an organic molecule with a fluorous tag. Tagged products are then separated from non-tagged ones by an organic/fluorous phase separation technique such as extraction. The fluorous tag may then be removed to return the purified compound to its original phase if desired. The method is illustrated in FIG. 8. The fluorous tags for the fluorous phase switch have the same general features as described above. In this example, selectivity is based on a target functional group X". The wealth of chemoselective transformations known in organic synthesis forms the basis for designing fluorous phase switches, which are much more general and useful than traditional acid/base switches for simple purification of organic mixtures.

Figure 9:
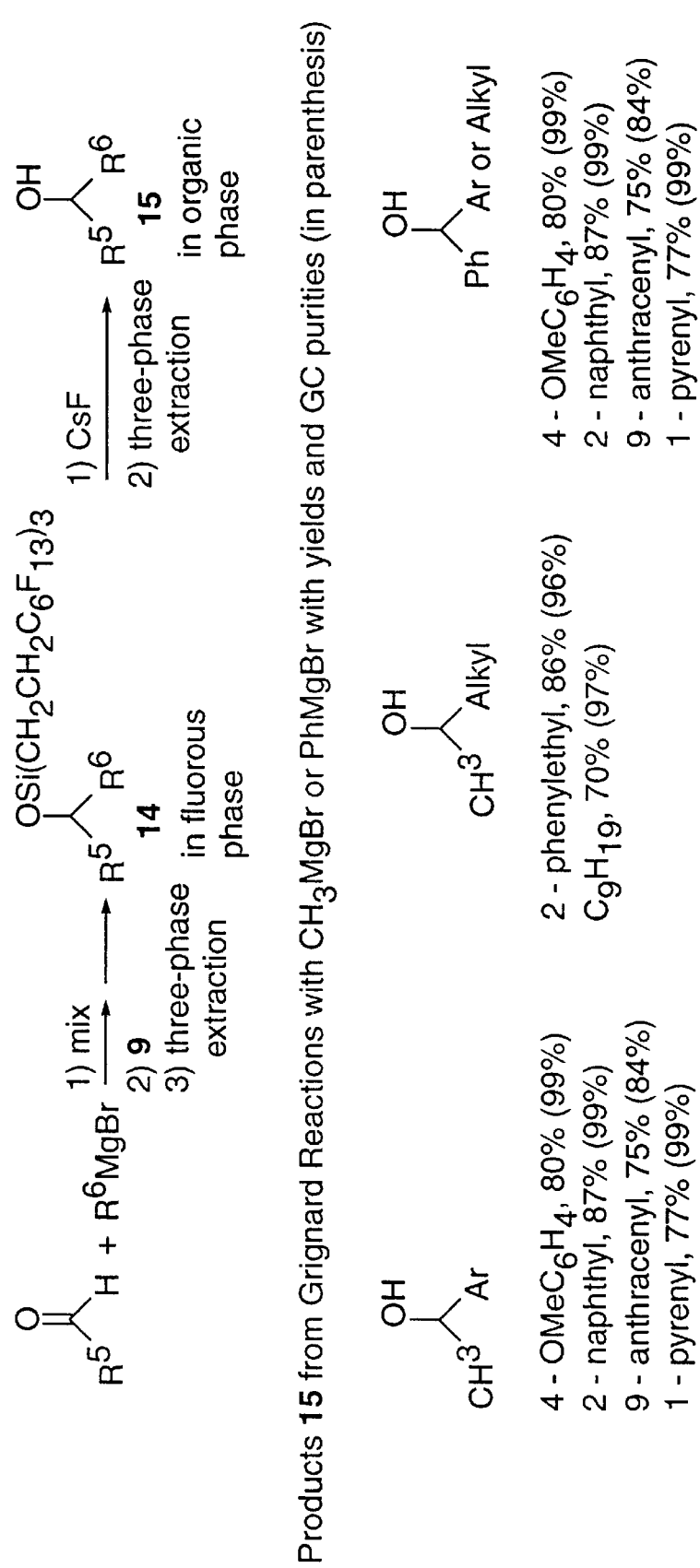
FIG. 9 illustrates purification of Grignard products by fluorous phase switching.

The technique is illustrated by the sequence shown in FIG. 9. A standard Grignard reaction of an aldehyde with 1.5 equiv of a Grignard reagent is followed by addition of excess fluorous tag 9. The fluorous ether products 14 are then separated by three-phase extraction. Treatment of these crude products with cesium fluoride (CsF) followed by a second three-phase extraction provides the alcohol products 15 in the yields and purities indicated in FIG. 9. These reactions demonstrate that the products can be tagged and extracted into the fluorous layer. The purification features of the technique are also apparent. For example, when the aldehyde is used in excess instead of the Grignard reagent, then the unreacted aldehyde is left in the organic phase after the first reaction. In the standard procedure where excess Grignard reagent is used, the residual reagent presumably reacts with an equivalent amount of the silylating agent to form a silane $RSi(CH_2CH_2C_6F_{13})_3$. This silane is extracted into the fluorous phase with the desired silyl ether in the first extraction. However, because it does not react with CsF, it is left in the fluorous phase during the second extraction when the alcohol switches back to the organic phase. In effect, the silyl ether 14 is "temporarily fluorous" but the silane is "permanently fluorous". There are thus two different triggers that can be manipulated: one into and one out of the fluorous phase.

Silylation is only one among many standard reactions that can be used for fluorous tagging. Others include but are not limited to acylations of organic alcohols, amines or other groups with fluorous acyl groups, sulfonyl groups or related groups (or the reverse), ketalization of organic aldehydes or ketones with fluorous diols (or the reverse), alkylation of organic oxygen-, nitrogen-, or carbon-based nucleophiles with fluorous halides, mesylates, or related alkylating agents (or the reverse), and many more.

Figure 10:
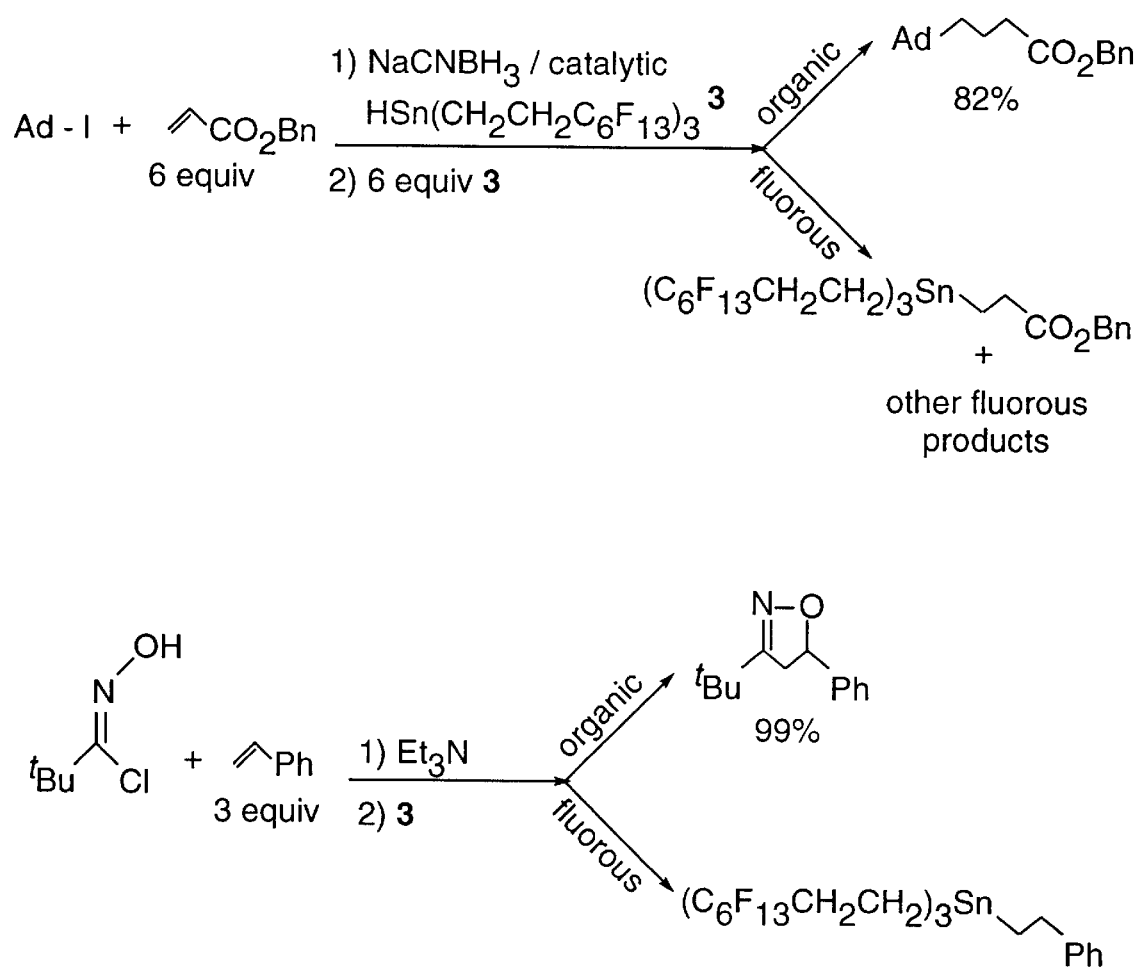
FIG. 10 illustrates fluorous tagging of residual reaction components or byproducts.

If the design is such that the desired products are organic and the impurities are fluorous, there is no need to pull the second trigger to complete the phase switch. This is shown by the simple radical addition and nitrile oxide cycloaddition reactions in FIG. 10. In both cases, excess alkene was used; this excess is essential for high yield in the radical addition but not in this particular nitrile oxide cycloaddition. After the reaction is complete, sufficient fluorous tin hydride 3 is added to hydrostannylate all unreacted alkene, and the reaction is partitioned into organic and fluorous phases as usual. In both cases, the organic phase contains the desired product free from unreacted alkene. It is evident that this type of fluorous tagging strategy can be extended to remove byproducts from the reaction components (as opposed to the unreacted reaction components themselves). The fluorous tags can be used in excess, since they are fluorous and will be separated from the organic product either in the first extraction or the second.

Figure 11:
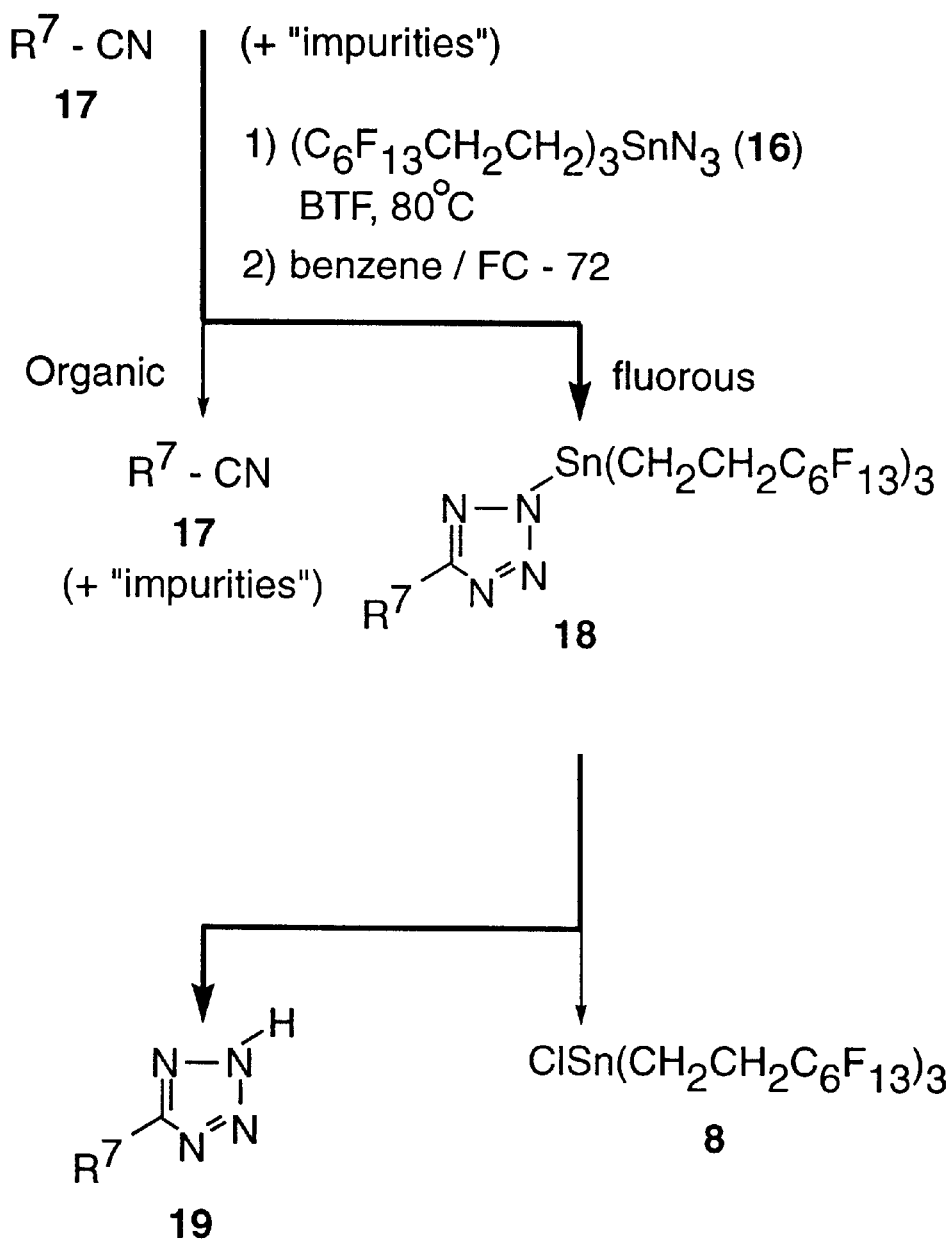
FIG. 11 illustrates the combination of a fluorous reagent and a fluorous phase tag.

The fluorous tags in these types of experiments are solely for the purposes of purification. However, for many types of reactions it is possible to "retool" existing reagents to directly integrate the tagging features. As an illustration of this, tin azide 16 shown in FIG. 11 was prepared. Tin azide 16 is the fluorous analog of tributyltin azide, which is a popular reagent for making tetrazoles from nitriles. See, Akido, K. et al., *J. Organometal. Chem.*, 33, 337 (1971). Reaction of an organic nitrile 17 used in twofold excess (to simulate incomplete conversion) with fluorous azide 16 in benzotrifluoride at 80° C. for 12 h provided the fluorous tetrazoles 18 after organic/fluorous extraction (benzene/FC-72) to remove unreacted nitrile and any other organic byproducts. Brief exposure of the fluorous tetrazoles 18 to ethereal HCl followed by fluorous/organic extraction (acetonitrile/FC-72) and evaporation of the organic (acetonitrile) phase provided the pure tetrazoles 19 in the indicated yields. These yields follow the expected trends for reactions with the reagent tributyltin azide. The above examples show the power of the fluorous phase switch to provide pure organic products even in reactions that do not occur in quantitative yield, and they also show the ability to remove fluorous reagents and byproducts from organic products. The ultimate fluorous product from the reaction, $(C_6F_{13}CH_2CH_2)_3SnCl$ 8, can be readily retrieved from the final fluorous phase and recycled in high yield.

A more common way to conduct these reactions would be to use excess tin azide to drive the reaction to completion based on the nitrile substrate. Indeed, the treatment of one equivalent of p-tolunitrile with three equivalents on tin azide 16 under the standard conditions provided pure tolyl tetrazole 19 ($R^7$=tol) in almost quantitative yield.

Finally, the phase switching method can also be used to rectify problems in prior steps of a sequence of synthetic steps. This was illustrated by a simple doping experiment. Since nitriles are commonly prepared from halides, 1 equiv of p-tolunitrile was doped with an additional equivalent of 4-bromotoluene and then the reaction and extraction sequence in FIG. 11 was carried out. The 4-bromotoluene does not react with the tin azide 16, and it partitions into the organigc layer in the first extraction. In the end, the desired tetrazole 19 ($R^7$=tol) was isolated in about the same yield and purity as in the experiment without the bromide.

Fluorous Multicomponent Reactions

Multicomponent reactions combine a substrate and two or more reactants to provide products in a single step. These reactions are especially important in combinatorial synthesis because structurally diverse libraries of products can be quickly made simply by mixing and matching the various reaction components. The fluorous techniques outlined herein are readily adaptable to multicomponent reactions and provide for simple purification of the products.

Figure 12:
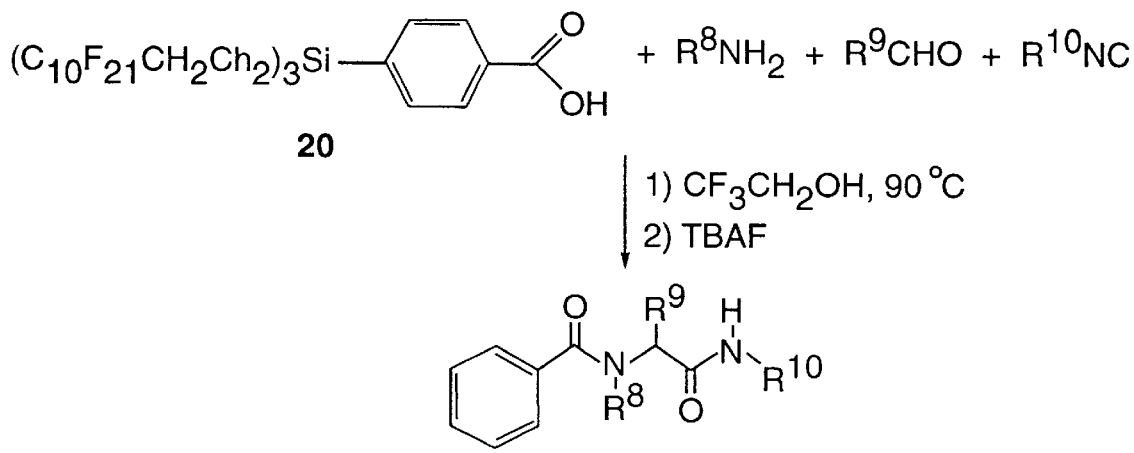
FIG. 12 illustrates several examples of fluorous Ugi reactions.

The "Ugi four component condensation" is an important multicomponent reaction because it brings together four diverse components to form amino acid amides. See, Ugi, I., *Angew. Chem.,* Int. Ed. Engl. 21, 810 (1982). Examples of a fluorous variant of the Ugi four component condensation are shown in FIG. 12. Fluorous acid 20 is prepared by a standard set of reactions as described in the section on "Experimental Examples". Reaction of fluorous acid 20 with large excesses (generally 17 equiv) of the other three components—an amine $R^8NH_2$, an aldehyde $R^9CHO$, and an isonitrile $R^{10}NC$ (the amine and the aldehyde are known to condense to form an imine, so for the purposes of illustration, preformed imines were also successfully used in a few examples)—followed by two-phase extraction (benzene/FC-72) and evaporation of the fluorous phase provided a fluorous Ugi product (not shown). The unreacted or partially reacted components and byproducts were left in the organic phase. Without further purification, the fluorous Ugi product was desilylated with tetrabutylammonium (TBAF). Extractive purification separates the fluorous tag and any other fluorous compounds from the organic Ugi product 21, which is isolated by evaporation of the final organic phase. Yields and purities of a series of products are listed FIG. 12. These yields and purities are impressive, especially considering that the product 21 derive from reaction of only 4 of the 52 total molar equivalents of reaction components in the mixture. Thus, the unreacted components and byproducts derived therefrom constitute by far the major part of the original crude reaction product.

Figure 13:
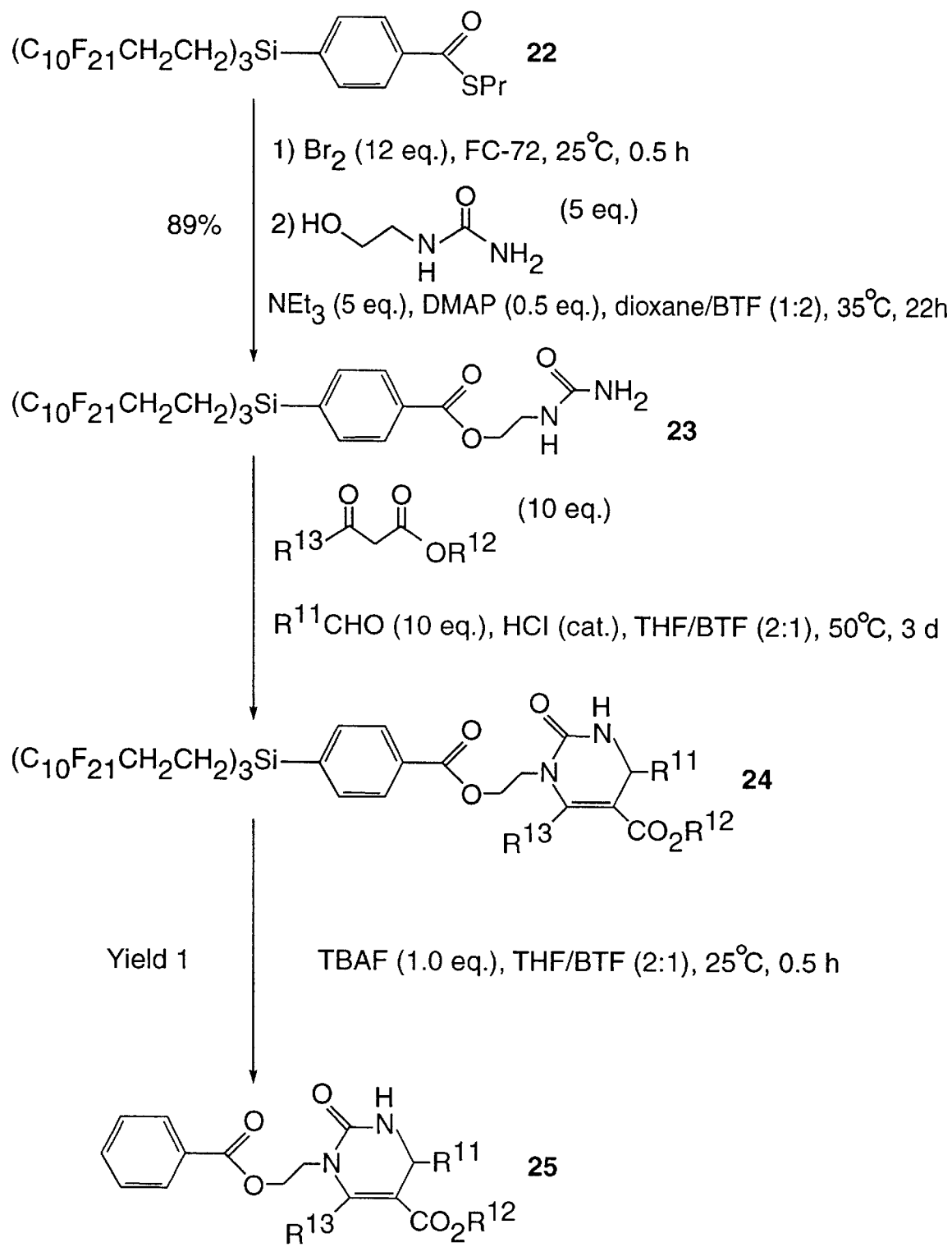
FIG. 13 illustrates an example of a fluorous analog of the Biginelli reaction.
Figure 14:
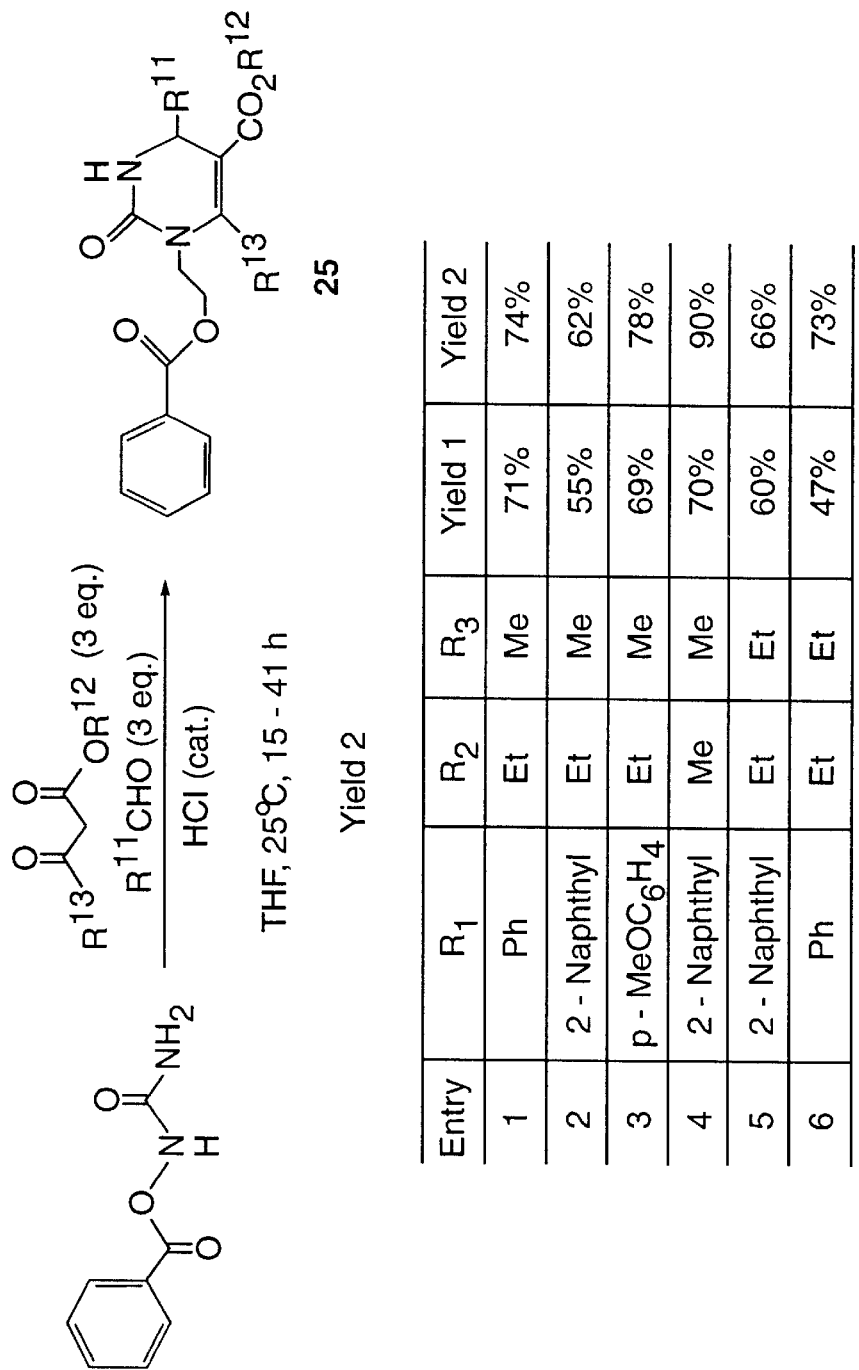
FIG. 14 illustrates a procedure and yields for the reaction of FIG. 13.

The Biginelli reaction is another important multicomponent reaction that has recently been transferred from its conventional solution form to the solid phase. See, Wipf, P.; Cunningham, A. *Tetrahedron Lett.,* 36, 7819 (1995). FIG. 13 illustrates a strategy for conducting Biginelli reactions by fluorous tagging. This method is compared with the conventional Biginelli reaction illustrated in FIG. 14. Excess keto-ester and aldehyde (3 equiv) are used to drive the conventional Biginelli reaction to completion, and the final products 25 must be purified by chromatography to remove excess reactants and byproducts.

As shown in FIG. 13, the fluorous Biginelli reaction requires no chromatography. Attachment of the urea to the acid bromide derived from 22 provides the requisite fluorous substrate 23, which is purified as usual by fluorous/organic extraction. The Biginelli reactions were again conducted with large excesses of keto ester and aldehyde reactants (10 equiv) both to drive the reactions to completion and to deliberately generate large amounts of organic reaction components to separate. The components were heated for 3 d at 50° C. in 2/1 THF/BTF containing HCl. The fluorous products 24 were then isolated by three-phase extraction. Desilylation with tetrabutylammonium fluoride (TBAF) followed by extractive purification provided the pure organic products 25, which were identical to the products prepared by the conventional procedure. Yields for the conventional procedure (yield 1) and the fluorous procedure (yield 2) are provided in FIG. 14. Product purities were good over a diverse range of absolute yields without any chromatographies.

These transformations illustrate the power of the fluorous approach for conducting and purifying multicomponent reactions. Beyond that, they also illustrate that medium-sized "drug-like" organic molecules can be synthesized by fluorous techniques. The final organic products of these multicomponent reactions typically have molecular weights in the range of 400–450. Yet the fluorous-tagged precursors of these products were successively extracted into the fluorous phase for purification. The acid 20 also provides an example where the fluorous tag has a role not as a protecting group, but instead as a surrogate for another atom or group; in this case, the tag is a surrogate for hydrogen in the final product.

The methods or strategies of fluorous phase tagging synthesis and separation set forth above are not mutually exclusive and can be readily integrated in multi-step sequences. For example, an organic compound can be rendered fluorous at an intermediate stage in a synthesis, and then one or more additional transformations can be conducted on the fluorous substrate prior to its return to the organic phase. The fluorous methods of the present invention can also be smoothly integrated with existing solid phase and liquid phase methods.

In the future, combinatorial synthesis of small molecule libraries by multi-step reaction sequences that do not occur in quantitative yield will place an increased demand on simple methods for purification of reaction mixtures. Issues of purification previously considered technical must be raised to the level of strategic planing on par with issues like regio- and stereocontrol, protecting groups, and the like. In this context, the fluorous methods presented herein provide new strategic options for purification in combinatorial and other synthesis.

EXPERIMENTAL EXAMPLES

1. Preparation of tris (3,3,4,4,5,5,6,6,7,7,8,8,8-Tridecafluorooctyl)phenyltin, (tris (2-Perfluoro-hexylethyl) phenyltin) (1a)

To the Grignard reagent prepared from 2-perfluorohexyl-1-iodoethane (100 g, 211 mmol) and magnesium (6.53 g, 269 mmol) in dry ether (150 mL) was added phenyltin-trichloride (15.9 g, 52.7 mmol) dissolved in dry benzene (100 mL). After refluxing for 4 h, the reaction was stirred for 16 hours at 25° C. The reaction mixture was hydrolyzed with $NH_4Cl$ solution, and the organic phase was washed with 5% $Na_2S_2O_3$ solution and deionized water, and then dried over anhydrous $MgSO_4$. The solvent was evaporated to dryness. After removal of the major byproduct bis (1,4-perfluorohexyl)butane by vacuum distillation (87–92° C., 0.2 mm Hg), the resulting residue was purified by column chromatography on neutral alumina with hexane to give pure compound 1a (56.1 g, 86%) as a colorless oil. $^1H$ NMR ($CDCl_3$) d 7.41 (s, 5 H), 2.31 (m, 6 H), 1.31 (t, J=8.3 Hz, $^2J$ ($^{119}$Sn-H) =53.4 Hz, 6 H); $^{119}$Sn NMR ($CDCl_3$)11.7 ppm; IR (thin film) 3100, 2950, 1238, 1190, 1144, 655 $cm^{-1}$; MS (m/z) 1161 ($M^+$–Ph), 891 ($M^+$–$CH_2CH_2C_6F_{13}$).

2. Preparation of Bromo tris (3,3,4,4,5,5,6,6,7,7,8,8,8-Tridecafluorooctyl) tin, (Bromo tris (2-perfluorohexyl) ethyltin) (2)

Bromine (5.83 g, 36.5 mmol) in ether (10 mL) was added dropwise to an ice-cold solution of 1a (43.0 g, 34.8 mmol) in dry ether (80 mL). The mixture was warmed to 25° C. over 2 h with stirring. Removal of the ether, bromobenzene, and excess of bromine by evaporation under reduced pressure resulted in an orange oil. Purification by vacuum distillation (150–152° C., 0.5 mm Hg) yielded compound 2 (42.4 g, 98%) as a colorless oil.

$^1$H NMR (CDCl$_3$) d 2.42 (m, 6 H), 1.56 (t, J=8.3 Hz, $^2$J ($^{119}$Sn-H) 53.4 Hz, 6 H); $^{119}$Sn NMR (hexane) 259.2 ppm (m); IR (thin film) 3600, 1250, 1227, 1145, 534 cm$^{-1}$; MS (m/z): 1161 (M$^+$–Br), 893 (M$^+$–CH$_2$CH$_2$C$_6$F$_{13}$).

3. Preparation of tris (3,3,4,4,5,5,6,6,7,7,8,8,8-Tridecafluorooctyl)tin Hydride, (tris (2-Perfluorohexyl) ethyltin Hydride) (3)

An ethereal solution of LiAlH$_4$ (0.8 mL, 0.8 mmol) (1M) was added dropwise to an ice-cold solution of tris (2-perfluorohexyl)ethyltin bromide (1.0 g, 0.8 mmol) in ether (20 mL) and the reaction mixture was stirred for 3 h at 0° C. The reaction mixture was quenched by slowly adding water (5 mL), followed by 20% sodium potassium tartrate solution (20 mL). After separation of the ethereal layer, the aqueous phase was extracted with ether (3×25 mL), and the combined extracts were dried over anhydrous MgSO$_4$. Removal of the ether by distillation yielded a slightly yellow liquid which was fractionated under reduced pressure. The fraction, boiling at 145–150° C., 3 mm Hg was collected yielding 910 mg (97%) of the hydride 3 as a colorless oil.

$^1$H NMR (CDCl$_3$) d 5.27 (s, 1 H), 2.35 (m, 6 H), 1.16 (t, J=8.1 Hz, $^2$J ($^{119}$Sn-H)=53.4 Hz, 6 H); $^{119}$Sn NMR (CDCl$_3$) 84.5 ($^1$J ($^{119}$Sn-H)=1835 Hz); IR (thin film) 1842, 1197 cm$^{-1}$. MS (m/z) 1161 (M$^+$–H), 813 (M$^+$–CH$_2$CH$_2$C$_6$F$_{13}$).

4. Representative Stoichiometric Experimental Procedure for Fluorous Tin Hydride Reductions To a stirred solution of 1-bromoadamantane (100 mg, 0.46 mmol) and tris (2-perfluorohexyl)ethyltin hydride (640 mg, 0.55 mmol) in benzotrifluoride (9.2 mL) was added a catalytic amount of AIBN. The reaction mixture was heated at reflux temperature for 3 h. The solvent was evaporated and the crude residue was partitioned between dichloromethane (20 mL) and perfluoromethylcyclohexane (10 mL). The two layers were separated and the dichloromethane phase was concentrated yielding adamantane as a pure compound (56 mg, 90%).

5. Representative Catalytic Experimental Procedure for Fluorous Tin Hydride Reductions A suspension of 1-bromoadamantane (347 mg, 1.60 mmol), bromo tris 2-(perfluorohexyl)ethyltin (200 mg, 0.16 mmol), sodium cyanoborohydride (138 mg, 2.1 mmol) and AIBN (in catalytic amount) in benzotrifluoride (1.6 mL) and tert-butanol (1.6 mL) was heated in a sealed tube at reflux during 3 h. The solvent was evaporated and the crude residue was partitioned between water (10 mL), dichloromethane (15 mL) and perfluoromethylcyclohexane (10 mL). The three layers were separated and the dichloromethane phase was dried over MgSO$_4$ yielding, after evaporation, adamantane as a pure compound (200 mg, 92%).

6. Representative Combinatorial Chemistry Experimental Procedure for Fluorous Tin Hydride Reductive Additions In a typical experiment, a suspension of alkyl iodide (0.1 mmol), olefin (0.5 mmol), bromo tris 2-(perfluorohexyl) ethyltin (12.4 mg, 0.01 mmol), sodium cyanoborohydride (9.6 mg, 0.13 mmol) and AIBN (in catalytic amount) in BTF (0.5 mL) and tert-butanol (0.5 mL) was heated at reflux in a sealed vial for 12 h.

To the cooled reaction mixture, PFMC (2 mL) and dichloromethane (1 mL) were added. After separation of the 2 phases, the dichloromethane phase was extracted another time with PFMC (1 mL) and then with water (1 mL). The organic phase was filtered through neutral alumina and evaporated to dryness. The yields of this reactions were determined by $^1$H NMR using CH$_2$Cl$_2$ and hexamethyldisiloxane as internal standards (See FIG. 3).

7. Representative Experimental Procedure for Fluorous Tin Hydride Reductive Cyclizations A suspension of hexenyl bromide (0.32 mmol), bromo tris (2-perfluorohexyl)ethyltin (40 mg, 0.032 mmol), sodium cyanoborohydride (28 mg, 0.42 mmol) and AIBN (in catalytic amount) in BTF (3.2 mL) and tert-butanol (3.2 mL) was heated at reflux in a sealed tube. The progress of the reaction was monitored by TLC. The solvent was evaporated and the crude residue was partitioned between water (8 mL), dichloromethane (15 mL) and FC-72 (12 mL). The three layers were separated and the dichloromethane phase (middle layer) was extracted twice with FC-72 (2×10 mL), dried over MgSO$_4$ yielding, after evaporation, the cyclopentane derivative. Starting from 6-bromo-1,1-diphenylhexene and 7-bromohept-2-enenitrile, diphenylmethylcyclopentane and cyclopentaneacetonitrile were isolated in 75 and 66% yield respectively.

8. Representative Procedure for Fluorous Tin Hydride Ionic Reductions of Aldehydes A solution of aldehyde (0.144 mmol), zinc chloride (393 mg, 2.88 mmol), tris (2-perfluorohexyl)ethyltin hydride (104 mg, 0.09 mmol) in ether (2.9 mL) was heated at reflux in a sealed tube. The progress of the reaction was monitored by TLC. The solvent was evaporated and to the crude residue was added water (2 mL), dichloromethane (5 mL) and PEMC (4 mL). The three resulting layers were separated and the dichloromethane layer (middle layer) was extracted twice with PFMC (2×5 mL), dried over MgSO$_4$, filtered through silica and evaporated under reduced pressure to yield the pure alcohol. In that way, benzyl alcohol, p-nitrobenzyl alcohol and 3-phenyl-1-propanol were obtained from benzaldehyde, p-nitrobenzaldehyde and 3-phenylpropanaldehyde in 78, 64 and 68% yield respectively.

9. Preparation of tris (3,3,4,4,5,5,6,6,7,7,8,8,8-Tridecafluorooctyl) (4'-methoxyphenyl)tin, (tris (2-Perfluorohexylethyl)(4'-methoxyphenyl)tin) (1b)

To the Grignard reagent prepared from 4-bromoanisole (681 mg, 3.64 mmol) and magnesium (102 mg, 4.20 mmol) in dry ether (20 mL) was added a solution of 2 (3.47 g, 2.80 mmol) in dry ether (10 mL). After refluxing for 1 h, the reaction was stirred for 16 h at 25° C. The reaction mixture was quenched with NH$_4$Cl solution and diluted with ether, and the organic phase was washed with deionized water then dried over anhydrous MgSO$_4$. The solvent was evaporated to dryness. Purification by vacuum distillation (166° C., 0.25 mm Hg) and then column chromatography on neutral alumina with hexane yielded pure compound 1b (5.20 g, 74%) as a colorless oil.

$^1$H NMR (CDCl$_3$) d 7.30 (d, J=8.3 Hz, 2 H), 6.98 (d, J=8.3 Hz, 2 H), 3.82 (s, 3 H), 2.29 (m, 6 H), 1.27 (t, J =8.3 Hz, $^2$J ($^{119}$Sn-H)=54.0 Hz, 6 H); $^{119}$Sn NMR (CDCl$_3$) 123.7 ppm; IR (thin film) 1500, 1375, 1240, 1205, 1145, 1065, 745, 700 cm$^{-1}$; MS (m/z) 1267 (M$^+$), 1161 (M$^+$–C$_6$H$_4$OMe), 921 (M$^+$–CH$_2$CH$_2$C$_6$F$_{13}$).

10. Preparation of tris (3,3,4,4,5,5,6,6,7,7,8,8,8-Tridecafluorooctyl)(2'-furyl)tin, (tris (2-Perfluorohexylethyl) (2'-furyl)tin) (1c)

To a solution of furan (667 mg, 9.80 mmol) in dry THF (25 mL) at 0° C. was added a 1.5 M solution of LDA in cyclohexane (6.53 mL, 9.80 mmol). After stirring 1 h at 0° C., the resulting mixture was treated with a solution of 2 (8.67 g, 7.00 mmol) in dry THF (15 mL). The reaction mixture was warmed to 25° C. over 1 h and then stirred for 16 h at 25° C. The reaction mixture was quenched with $NH_4Cl$ solution and diluted with ether. After separation, the organic phase was washed with deionized water and then dried over anhydrous $MgSO_4$. The solvent was evaporated to dryness. Column -chromatography on neutral alumina with hexane yielded pure compound 1c (2.44 g, 28%) as a colorless oil.

$^1$H NMR ($CDCl_3$) d 7.76 (s, 1 H), 6.63 (s, 1 H), 6.47 (s, 1 H), 2.35 (m, 6 H), 1.29 (t, J=9.7 Hz, $^2$J ($^{119}$Sn-H)=56.8 Hz, 6 H); $^{119}$Sn NMR ($CDCl_3$) 100.7 ppm; IR (thin film) 1445, 1355, 1240, 1205, 1145, 1065, 745, 700 cm$^-$; MS (m/z) 1228 ($M^+$), 1161 ($M^+$-furyl), 881 ($M^+CH_2CH_2C_6F_{13}$).

11. Preparation of tris (3,3,4,4,5,5,6,6,7,7,8,8,8-Tridecafluorooctyl)(2'-pyridyl)tin, (tris (2-Perfluorohexylethyl) (2'-pyridyl) tin) (1d)

To the Grignard reagent prepared from 2-bromopyridine (822 mg, 5.20 mmol) and magnesium (146 mg, 6.20 mmol) in dry ether (30 mL) was added a solution of 2 (2.48 g, 2.00 mmol) in dry ether (5 mL). After refluxing for 1 min., the reaction was stirred for 17 hours at 25° C. The reaction mixture was quenched with $NH_4Cl$ solution. After separation, diluted with ether, and the organic phase was washed with deionized water and then dried over anhydrous $MgSO_4$. The solvent was evaporated to dryness, and the resulting residue was partitioned between toluene and FC-72. The two phases were separated. The FC-72 phase was washed with toluene and concentrated to afford pure compound 1d (2.18 g, 88%) as a pale yellow oil.

$^1$H NMR ($CDCl_3$) d 8.71 (d, J=4.3 Hz, 1 H), 7.58 (t, J=7.7 Hz, 1 H), 7.36 (d, J=7.3 Hz, 1 H), 8.20 (m, 1 H), 2.29 (m, 6 H), 1.34 (t, J=8.2 Hz, $^2$J ($^{119}$Sn-H)=54.3 Hz, 6 H); $^{119}$Sn NMR ($CDCl_3$) 88.6 ppm; IR (thin film) 1570, 1450, 1360, 1240, 1205, 1145, 1060, 735, 700 cm$^{-1}$; MS (m/z) 1238 ($M^+$), 1161 ($M^+$-pyridyl), 892 ($M^+$–$CH_2CH_2C_6F_{13}$).

12. General Procedure for the Stille Couplings

A sealed tube under nitrogen was charged with tin reactant (0.24 mmol), substrate (0.20 mmol), lithium chloride (25.4 mg, 0.60 mmol), dichlorobis(triphenylphosphine)palladium (II) (2.8 mg, 0.004 mmol), dry DMF (0.5 mL), and dry THF (0.5 mL). The mixture was heated at 80° C. for 22 h. The solvent was evaporated and the residue was partitioned between water (10 mL), dichloromethane (15 mL), and FC-72 (10 mL). The three phases were separated and the dichloromethane phase was dried over anhydrous $MgSO_4$. Evaporation of the FC-72 phase provided chloro tris (3,3,4,4,5,5,6,6,7,7,8,8,8-tridecafluorooctyl)tin, (chloro tris (2-perfluorohexyl)ethyltin), which was routinely recycled. Evaporation of the dichloromethane phase provided crude organic product, which was further purified by silica gel preparative TLC to provide the major cross-coupled product 6 (see yields in FIG. 4C) and a small amount (5–10%) of the symmetrical biaryl 7 derived from the tin reactant.

13. Chloro tris (3,3,4,4,5,5,6,6,7,7,8,8,8-Tridecafluorooctyl) Tin 8, (Chloro tris (2-Perfluorohexyl) ethyltin 8)

$^1$H NMR ($CDCl_3$) d 2.46 (m, 6 H), 1.53 (t, J=7.9 Hz, $^2$J ($^{119}$Sn-H)=47.6 Hz, 6 H); $^{119}$Sn NMR ($CDCl_3$) 273 ppm; IR (thin film) 1450, 1360, 1240, 1205, 1145, 1065, 735, 700 cm$^{-1}$; MS (m/z): 1161 ($M^+$-Cl), 849 ($M^+$–$CH_2CH_2C_6F_{13}$).

14. Representative Example of a Preparative Stille Coupling

A sealed tube under nitrogen was charged with tin reactant 1a (2.97 g, 2.40 mmol), 1-bromo-4-nitrobenzene (404 mg, 2.00 mmol), lithium chloride (254 mg, 6.00 mmol), dichlorobis(triphenylphosphine)palladium(II) (28.1 mg, 0.04 mmol), dry DMF (5 mL), and dry THF (5 mL). The mixture was heated to 80° C. and a homogeneous solution resulted. The mixture was stirred at 80° C. for 22 h. After azeotropic evaporation with toluene at 75° C. (to remove THF and some of the DMF), the resulting residue was partitioned between water (40 mL), dichloromethane (60 mL), and FC-72 (40 mL). The three phases were separated. Evaporation of the FC-72 phase provided 2.31 g (80.6% from 1a) of tin chloride 8 as a colorless oil. The dichloromethane phase was washed three more times with water (40 mL) and FC-72 (40 mL). Evaporation of the combined FC-72 phases (including the first phase) provided 2.85 g (99.4% from 1a) of tin chloride 8. The final dichloromethane phase was dried over anhydrous $MgSO_4$ and evaporated to give yellow crystals free of fluorous reactant 1a and fluorous tin halides. The crude organic product was further purified by column chromatography on silica gel to provide the cross-coupled product, 4-nitrobiphenyl (337 mg, 85%) as yellow crystals, and the homo-coupled product, biphenyl (17 mg, 5%), as white crystals.

15. Representative Example of Recycling of Tin Reactants

The tin chloride 8 (2.85 g) isolated by evaporation of FC-72 phase after the above Stille coupling was treated with a 3M solution of phenyl magnesium bromide in ether (1.04 mL, 3.12 mmol ) in dry ether (25 mL) under stirring at 25° C. for 6 h. The reaction mixture was hydrolyzed with $NH_4Cl$ solution and diluted with ether, and the organic phase was washed with deionized water then dried over anhydrous $MgSO_4$. The solvent was evaporated to dryness. Column chromatography on neutral alumina with hexane yielded pure compound 1a (2.85 g, 96% overall from 1a in the preceding section) as a colorless oil.

16. Bis tris (3,3,4,4,5,5,6,6,7,7,8,8,8-Tridecafluorooctyl) tin Oxide, (Bis [tris (2-Perfluorohexyl)ethyltin]oxide [$(C_6F_{13}CH_2CH_2)_3Sn]_2O$; an Alternative Procedure for the Preparation of Tin Hydride 3

Sodium hydroxide (254 mg, 6.33 mmol) in 8.4 mL of water was added to a solution of tris (2-perfluorohexyl) ethyltin bromide (5.23 g, 4.22 mmol) in acetone (55 ml). The mixture was heated at reflux for 12 h. The solvents mixture was evaporated. To the residue was added 10 ml of anhydrous toluene, and the resulting solution heated in a reflux apparatus equipped with a Dean-Stark type water trap for 12 h. The toluene solution was evaporated and the residue was dried over $P_2O_5$ in a vacuum desiccator for 12 h. The residue was extracted with dried hexane. The organic fraction collected was concentrated yielding the bis [tris (2-perfluorohexyl)ethyltin] oxide (3 g, 61%) as a viscous yellow oil.

$^1$H NMR ($CDCl_3$) d 2.45 (m, 12H); 1.55 (t, J =8.3 Hz, $^2$J ($^{119}$Sn-H)=53.4 Hz, 12 H); $^{119}$Sn NMR ($CDCl_3$) 165.54 ppm A mixture of bis [tris (2-perfluorohexyl)ethyltin] oxide (3 g, 1.28 mmol) and polymethylhydrosiloxane (191 mL; 3.22 mmol) was stirred at 25° C. for 12 h. After addition of ether, the presence of the tin hydride was shown by TLC comparison with an authentic sample.

17. Preparation of tris (3,3,4,4,5,5,6,6,7,7,8,8,8-Tridecafluorooctyl)allyltin, (tris (2-perfluorohexylethyl) allyltin), [$(C_6F_{13}CH_2CH_2)_3SnCH_2CHCH_2$]

Allylmagnesium bromide (0.10 ml, 0.10 mmol) 1M in ether was added to a solution of 2 (100 mg, 0.08 mmol) in ether (4 mL). The mixture was heated at reflux for 2 h with stirring. To the reaction cooled to 0° C., and a saturated solution of aqueous ammonium chloride (3 ml) and ether (5 ml) were added. The two phases were separated and the aqueous phase was extracted twice with ether (2×10 ml). The ether phase was dried over $MgSO_4$ yielding, after evaporation, the allyl derivative (62 mg, 64%) as a white oil.

$^1$H NMR ($CDCl_3$) d 5.95 (m, 1H); 5.0–4.8 (m, 2H); 2.30 (m, 6H); 1.95 (d, 2H, J=9 Hz); 1.20 (t, J=8.3 Hz, 6H).

18. Bromo tris(3,3,4,4,5,5,6,6,7,7,8,8,8-tridecafluorooctyl)silane (Bromo tris[2-(perfluorohexyl) ethyl]silane)]

Tris(3,3,4,4,5,5,6,6,7,7,8,8,8-tridecafluorooctyl)silane (1.00 g, 0.94 mmol; prepared as described in *J. Fluorine Chem.* 1993, 60, 211) was dissolved in FC-72 (4 mL) at 25° C. under argon. Bromine (0.08 mL, 1.41 mmol) was slowly added and the resulting solution was stirred for 8 h at 25° C. The reaction mixture was washed twice with $CH_2Cl_2$. Evaporation of the fluorous layer yielded the bromosilane 9 as a colorless oil (1.08 g, 99%): IR (neat) 2952, 1443, 1362, 1317, 1240, 1209, 1145, 1122, 1073, 905, 812, 737, 707 cm$^{-1}$; $^1$H NMR (300 MHz, $CDCl_3$) d 1.24–1.30 (m, 6 H), 2.11–2.28 (m, 6 H); $^{19}$F NMR (470 MHz, $CDCl_3$) d (rel. to $FCCl_3$) −126.82, −123.88, −123.53, −122.55, −116.32, −81.43.

19. Allyloxy-tris[2-(perfluorohexyl)ethyl]silane (11)

Allyl alcohol 10 (0.06 mL, 0.91 mmol) and triethylamine (0.13 mL, 0.91 mmol) were dissolved in dry THF (2 mL) under argon. A mixture of bromo tris[2-(perfluorohexyl) ethyl]silane 9 (260 mg, 0.23 mmol) in THF (2 mL) was slowly added to the above mixture at 25° C. The resulting mixture was stirred at 25° C. for 3 h. After removal of the solvent, the residue was purified by 3-phase extraction with FC-72 (10 mL), $CH_2Cl_2$ (10 mL), and $H_2O$ (10 mL). The organic-aqueous biphase was additionally extracted twice with FC-72 (10 mL). After evaporation of the combined fluorous extracts, the residue was further purified by flash-chromatography (hexanes-$Et_2O$, 50:1), yielding allyloxy-tris[2-(perfluorohexyl)ethyl]silane 11 as a colorless oil (115 mg, 45%): IR (neat) 2949, 2910, 1362, 1317, 1234, 1211, 1196, 1144, 1121, 1075, 1040, 904, 845, 812, 736, 707 cm$^{-1}$; $^1$H NMR (300 MHz, $CDCl_3$) d 0.93–0.99 (m, 6 H), 2.03–2.20 (m, 6 H), 4.21 (d, J=5.0 Hz, 2 H), 5.18 (dd, $J_1$=10.4 Hz, $J_2$=1.5 Hz, 1 H), 5.26 (dd, $J_1$=17.1 Hz, $J_2$=1.5 Hz, 1 H) , 5.84–5.97 (m, 1 H); $^{13}$C NMR (75 MHz, $CD_3COCD_3$) d 3.44, 25.56 (t, J=23.3 Hz), 64.93, 108.21–123.06 (m, $CF_2$, $CF_3$), 115.93, 137.85; $^{19}$F NMR (470 MHz, $CDCl_3$) d (rel. to $CFCl_3$) −126.89 (t, J=4.7 Hz), −124.06, −123.60, −122.64, −116.96 (t, J=18.8 Hz), −81.57 (t, J=9.4 Hz) ; MS m/z 1126 (M$^+$) , 451, 349, 309, 239, 195.

20. tris [2-(Perfluorohexyl)ethyl] (2-methylallyloxy) silane

2-Methyl-2-propen-1-ol (0.47 mL, 5.59 mmol) and triethylamine (0.79 mL, 5.59 mmol) were dissolved in dry THF (10 mL) under argon. A mixture of bromo tris[2-(perfluorohexyl)ethyl]silane 9 (1.60 g, 1.39 mmol) in THF (5 mL) was slowly added to the above solution at 25° C. The resulting mixture was stirred at 25° C. for 2 h. After removal of the solvent, the residue was purified by 3-phase extraction with FC-72 (20 mL), $CH_2Cl_2$ (20 mL), and $H_2O$ (20 mL). The organic-aqueous biphase was additionally extracted twice with FC-72 (20 mL). After evaporation of the combined fluorous extracts, the residue was further purified by flash-chromatography (hexanes-$Et_2O$, 50:1), yielding tris[2-(perfluorohexyl)ethyl]-(2-methyl-allyloxy)silane as a colorless oil (602 mg, 46%): IR (neat) 2949, 2916, 1362, 1317, 1237, 1206, 1145, 1121, 1074, 905, 736, 707 cm$^{-1}$; $^1$H NMR (300 MHz, $CDCl_3$) d 0.94–0.99 (m, 6 H), 1.72 (s, 3 H), 2.03–2.21 (m, 6 H), 4.08 (s, 3 H), 4.89 (s, 1 H), 4.94 (s, 1 H); $^{13}$C NMR (75 MHz, $CD_3COCD_3$) d 3.48, 18.96, 25.68 (t, J=22.5 Hz), 67.65, 105.87–124.09 (m, $CF_2$, $CF_3$), 111.91; 145.11; $^{19}$F NMR (470 MHz, $CDCl_3$) d (rel. to $CFCl_3$) −126.95 (q, J=4.7 Hz) , −124.13, −123.64, −122.68, −117.01 (t, J=14.1 Hz), −81.64 (t, J=9.4 Hz); MS m/z 1140 (M$^+$), 239, 137.

21. tris [2-(Perfluorohexyl)ethyl] (prop-2-ynyloxy) silane

Propargyl alcohol (0.10 mL, 1.74 mmol) and triethylamine (0.26 mL, 1.74 mmol) were dissolved in dry THF (10 mL) under argon. A mixture of bromo tris[2-(perfluorohexyl)ethyl]silane 9 (1.00 g, 0.87 mmol) in THF (2 mL) was slowly added to the above solution at 25° C. The resulting suspension was stirred at 25° C. for 3 h. After removal of the solvent, the residue was purified by 3-phase extraction with FC-72 (15 mL), $CH_2Cl_2$ (15 mL), and $H_2O$ (15 mL). The organic-aqueous biphase was additionally extracted twice with FC-72 (15 mL). Evaporation of the combined fluorous extracts yielded a mixture of tris[2-(perfluorohexyl)ethyl](prop-2-ynyloxy)silane and silanol in a ratio of 87 to 13 as a colorless oil (960 mg, 98 %): IR (neat) 3317, 2950, 2911, 1443, 1362, 1317, 1244, 1234, 1221, 1198, 1144, 1120, 1076, 905, 812, 736, 708 cm$^{-1}$; $^1$H NMR (300 MHz, $CDCl_3$) d 0.98–1.04 (m, 6 H), 2.07–2.24 (m, 6 H), 2.50 (t, J=2.5 Hz, 1 H), 4.38 (d, J=2.6, 2 H); $^{13}$C NMR (75 MHz, $CD_3COCD_3$) d 3.72, 25.71 (t, J=23.3 Hz), 52.50, 75.85, 82.46, 105.94–124.18 (m, $CF_2$, $CF_3$); MS m/z 778 ((M$^+$+1)$CH_2CH_2(CF_2)_5CF_3$), 374, 293, 226, 184.

22. General Procedure for the Preparation of Isoxazol(in)es by Mukaiyama's Method (General Procedure 1)

To a solution of the silyl ether (0.10 mmol) in BTF (4 mL) were added the nitro alkane (0.99 mmol), phenyl isocyanate (0.22 mL, 1.98 mmol), and two drops of triethylamine. The reaction mixture was stirred at 25° C. for 3 days. After removal of the solvent, the residue was purified by 3-phase extraction with FC-72 (20 mL), $H_2O$ (20 mL), and benzene (20 mL). The organic-aqueous biphase was additionally extracted twice with FC-72 (20 mL). The combined fluorous extracts were evaporated to yield the desired isoxazol(in)e. (For small scale reactions the crude reaction mixture was diluted with benzene and extracted three times with FC-72. The combined fluorous extracts were filtered and evaporated.)

23. General Procedure for the Preparation of Isoxazol(in)es by Huisgen's Method (General Procedure 2)

The silyl ether (0.09 mmol) and the oxime (0.36 mmol) were placed at 25° C. in $CH_2Cl_2$ (6 mL), triethylamine (0.36 mmol) was added and the reaction mixture was stirred at 25° C. for 24 h. After removal of the solvent, the residue was purified by three-phase extraction with FC-72 (15 mL), $H_2O$ (15 mL), and benzene (15 mL). The organic-aqueous biphase was additionally extracted twice with FC-72 (15 mL). The combined fluorous extracts were evaporated to yield the desired isoxazol(in)e. (For small scale reactions the crude reaction mixture was suspended in benzene and extracted three times with FC-72.)

24. 3-Methyl-5-tris[2-(perfluorohexyl)ethyl] silanyloxymethyl-4,5-dihydroisoxazole Prepared according to general procedure 1 with allyl silyl ether 11 (0.050 g, 0.044 mmol), BTF (2 mL), nitroethane (0.03 mL, 0.44 mmol), and phenyl isocyanate (0.10 mL, 0.88 mmol) to afford the isoxazoline (53 mg, 99%): IR (neat) 2947, 2932, 1441, 1361, 1352, 1317, 1236, 1206, 1144, 1122, 1071, 1022, 905, 845, 811, 737, 707 cm$^{-1}$; $^1$H NMR (300 MHz, CDCl$_3$) d 0.91-1.00 (m, 6 H), 1.96 (s, 3 H), 2.00–2.22 (m, 6 H), 2.75 (dd, J$_1$=17.1 Hz, J$_2$=7.3 Hz, 1 H), 2.98 (dd, J$_1$=17.0 Hz, J$_2$=10.8 Hz, 1 H), 3.68 (dd, J$_1$=11.4 Hz, J$_2$=4.5 Hz, 1 H), 3.80 (dd, J$_1$=11.4 Hz, J$_2$=3.1 Hz, 1 H), 4.57–4.66 (m, 1 H); $^{13}$C NMR (750 MHz, CDCl$_3$) d 2.94, 12.74, 24.68 (t, J=23.3 Hz), 39.85, 64.73, 79.51, 104.61–121.39 (m, CF$_2$, CF$_3$), 155.11; $^{19}$F NMR (470 MHz, CDCl$_3$) d (rel. to CFCl$_3$) –126.74 (t, J=4.7 Hz), –123.86, –123.46, –122.51, –116.72 (t, J=14.1 Hz), –81.37 (t, J=9.4 Hz) ; MS m/z 1164 (M$^+$–F), 936, 836, 508, 309, 239, 195; HRMS calcd. for C$_{21}$H$_{16}$NO$_2$F$_{26}$Si (M$^+$–(CH$_2$)$_2$(CF$_2$)$_5$CF$_3$) m/z 836.0535, found 836.0514.

25. 3-Phenyl-5-tris[2-(perfluorohexyl)ethyl] silanyloxymethyl-4,5-dihydroisoxazole Prepared according to general procedure 2 with the allyl silyl ether 11 (0.069 g, 0.061 mmol), phenyl hydroximic acid chloride (38.0 mg, 0.25 mmol), and triethylamine (0.037 mL, 0.25 mmol) in CH$_2$Cl$_2$ (4 mL) to afford the isoxazoline (73 mg, 96%): IR (neat) 2945, 2912, 1442, 1359, 1316, 1240, 1205, 1144, 1122, 1072, 1018, 904, 745, 737, 707 cm$^{-1}$; $^1$H NMR (300 MHz, CDCl$_3$) d 0.91–1.00 (m, 6 H), 2.01–2.19 (m, 6 H), 3.20 (dd, J=16.6 Hz, J$_2$=8.1 Hz, 1 H), 3.40 (dd, J$_1$=16.6 Hz, J$_2$=10.9 Hz, 1 H), 3.78 (dd, J$_1$=11.5 Hz, J$_2$=4.4 Hz, 1 H), 3.91 (dd, J$_1$=11.5 Hz, J$_2$=2.9 Hz, 1 H), 4.79–4.87 (m, 1 H), 7.35–7.40 (m, 3 H), 7.63–7.66 (m, 2 H); $^{13}$C NMR (75 MHz, CDCl$_3$) d 2.95, 24.66 (t, J=23.3 Hz), 36.13, 64.85, 80.47, 104.61–119.13 (m, CF$_2$, CF$_3$), 126.55, 128.74, 129.06, 130.28, 156.51; $^{19}$F NMR (470 MHz, CDCl$_3$) d (rel. to CFCl$_3$) –126.72 (t, J=4.7 Hz), –123.86, –123.45, –122.52, –116.72 (t, J=14.1 Hz), –81.34 (t, J=9.4 Hz); MS m/z 1245 (M$^+$), 1226 (M$^+$–F), 898 (M$^+$–(CH$_2$)$_2$(CF$_2$)$_5$CF$_3$), 378, 309, 239, 195.

26. 3-tert-Butyl-5-tris[2- (perfluorohexyl)ethyl] silanyloxymethyl-4,5-dihydroisoxazole Prepared according to general procedure 2 with the allyl silyl ether 11 (0.054 g, 0.048 mmol), tert-butyl hydroximic acid chloride (46.0 mg, 0.34 mmol), and triethylamine (0.05 mL, 0.34 mmol) in CH$_2$Cl$_2$ (4 mL) to afford the isoxazoline (59 mg, 99%): IR (neat) 2363, 1442, 1363, 1317, 1240, 1199, 1144, 1121, 1072, 905, 811, 744, 737, 707 cm$^{-1}$; $^1$H NMR (300 MHz, CDCl$_3$) d 0.91–1.00 (m, 6 H), 1.10 (s, 9 H), 2.04–2.22 (m, 6 H), 2.78 (dd, J$_1$=16.9 Hz, J$_2$=7.2 Hz, 1 H), 3.00 (dd, J$_1$=16.9 Hz, J$_2$=10.6 Hz, 1 H), 3.66 (dd, J$_1$=11.4 Hz, J$_2$=4.9 Hz, 1 H), 3.76 (dd, J$_1$=11.2 Hz, J$_2$=3.3 Hz, 1 H), 4.57–4.65 (m, 1 H); $^{13}$C NMR (75 MHz, CDCl$_3$) d 2.78, 24.61 (t, J=23.3 Hz), 27.71, 32.86, 35.42, 64.59, 79.47, 104.54–122.85 (m, CF$_2$, CF$_3$), 165.81; $^{19}$F NMR (470 MHz, CDCl$_3$) d (rel. to CFCl$_3$) –126.78 (t, J=4.7 Hz), –123.87, –123.50, –122.54, –116.72 (t, J=14.1 Hz), –81.41 (t, J=14.1 Hz); MS m/z 1206 (M$^+$–F), 309, 239, 195, 126.

27. 3-Propyl-5-tris[2-(perfluorohexyl)ethyl] silanyloxymethyl-4,5-dihydroisoxazole Prepared according to general procedure 1 with the allyl silyl ether 11 (0.111 g, 0.099 mmol), BTF (4 mL), nitrobutane (0.10 mL, 0.99 mmol), and phenyl isocyanate (0.22 mL, 1.98 mmol) to afford the isoxazoline (125 mg, 99%): IR (neat) 2971, 2944, 2914, 2881, 1362, 1317, 1239, 1207, 1144, 1121, 1071, 906, 745, 736, 707 cm$^{-1}$; $^1$H NMR (300 MHz, CDCl$_3$) d 0.89–1.00 (m, 9 H), 1.51–1.63 (m, 2 H), 2.03–2.21 (m, 6 H), 2.29 (t, J=7.4 Hz, 2 H), 2.73 (dd, J$_1$=17.0 Hz, J$_2$=7.3 Hz, 1 H), 2.96 (dd, J$_1$=17.0 Hz, J$_2$=10.8 Hz, 1 H), 3.67 (dd, J$_1$=11.4 Hz, J$_2$=4.7 Hz, 1 H), 3.78 (dd, J$_1$=11.3 Hz, J$_2$=3.1 Hz, 1 H), 4.57–4.65 (m, 1 H); $^{13}$C NMR (75 MHz, CD$_3$COCD$_3$) d 3.48, 13.98, 20.44, 25.47 (t, J=23.3 Hz), 38.85, 65.81, 80.38, 109.32–123.54 (m, CF$_2$, CF$_3$), 159.19; MS m/z 1211 (M$^+$), 1192 (M$^+$–F), 848, 803, 293, 226, 157.

28. 3,5-Dimethyl-5-tris[2-(perfluorohexyl)ethyl] silanyloxymethyl-4,5-dihydroisoxazole Prepared according to general procedure 1 with the allyl silyl ether (0.107 g, 0.094 mmol), BTF (4 mL), nitroethane (0.07 mL, 0.94 mmol), and phenyl isocyanate (0.20 mL, 1.88 mmol) to afford the isoxazoline (112 mg, 99%): IR (neat) 2935, 1442, 1362, 1352, 1336, 1316, 1238, 1206, 1144, 1120, 1072, 906, 811, 745, 736, 707 cm$^{-1}$; $^1$H NMR (300 MHz, CDCl$_3$) d 0.93–0.99 (m, 6 H), 1.30 (s, 3 H), 1.91 (s, 3 H), 2.02–2.19 (m, 6 H), 2.58 (d, J=17.1 Hz, 1 H), 2.91 (d, J=17.1 Hz, 1 H), 3.57 (d, J=11.0 Hz, 1 H), 3.63 (d, J=10.9 Hz, 1 H); $^{13}$C NMR (75 MHz, CDCl$_3$) d 2.87, 12.92, 22.26, 24.68 (t, J=24.0 Hz), 45.68, 68.06, 85.35, 105.16–122.96 (m, CF$_2$, CF$_3$), 155.05; MS m/z 1178 (M$^+$–F), 928, 850 (M$^+$–(CH$_2$)$_2$(CF$_2$)$_5$CF$_3$), 795, 309, 239.

29. 3-tert-Butyl-5-methyl-5-tris[2-(perfluorohexyl)ethyl] silanyloxymethyl-4,5-dihydroisoxazole Prepared according to general procedure 2 with the allyl silyl ether (0.104 g, 0.091 mmol), tert-butyl hydroximic acid chloride (50.0 mg, 0.36 mmol), and triethylamine (0.054 mL, 0.364 mmol) in CH$_2$Cl$_2$ (4 mL) to afford the isoxazoline (115 mg, 99%): IR (neat) 2976, 2939, 2913, 2875, 2361, 2343, 2331, 1365, 1316, 1239, 1208, 1144, 1120, 1073, 899, 745, 736, 707 cm$^{-1}$; $^1$H NMR (300 MHz, CDCl$_3$) d 0.94–0.99 (m, 6 H), 1.16 (s, 9 H), 1.31 (s, 3 H), 2.10–2.21 (m, 6 H), 2.61 (d, J=16.7 Hz, 1 H), 2.94 (d, J=16.7 Hz, 1 H), 3.57 (d, J=10.9 Hz, 1 H), 3.62 (d, J=11.0 Hz, 1 H); $^{13}$C NMR (75 MHz, CDCl$_3$) d 2.89, 22.15, 24.73 (t, J=24.0 Hz), 27.73, 33.03, 41.32, 67.80, 85.22, 105.16–122.96 (m, CF$_2$, CF$_3$), 165.95; $^{19}$F NMR (470 MHz, CDCl$_3$) d (rel. to CFCl$_3$) –127.06 (t, J=4.7 Hz), –124.10, –123.72, –122.74, –116.96 (t, J=14.1 Hz), –81.79 (t, J=14.1 Hz); MS m/z 1220 (M$^+$–F), 1126, 795, 475, 309, 239, 195, 140.

30. 5-Methyl-3-propyl-5-tris[2-(perfluorohexyl)ethyl]-silanyloxymethyl-4,5-dihydroisoxazole Prepared according to general procedure 1 with the allyl silyl ether (0.100 g, 0.088 mmol), BTF (4 mL), nitrobutane (0.09 mL, 0.88 mmol), and phenyl isocyanate (0.19 mL, 1.76 mmol) to afford the isoxazoline and starting silane (ratio 94:6, 1.06 mg): IR (neat) 2974, 2943, 2914, 2881, 1442, 1362, 1317, 1236, 1207, 1144, 1121, 1072, 907, 811, 736, 707 cm$^{-1}$; $^1$H NMR (300 MHz, CDCl$_3$) d 0.89–0.99 (m, 9 H), 1.31 (s, 3 H), 1.49–1.62 (m, 2 H), 2.03–2.19 (m, 6 H), 2.26 (t, J=7.4 Hz, 2 H), 2.56 (d, J=16.7 Hz, 1 H), 2.90 (d, J=16.7 Hz, 1 H), 3.58 (d, J=10.9 Hz, 1 H), 3.63 (d, J=10.9 Hz, 1 H); $^{13}$C NMR (75 MHz, CD$_3$COCD$_3$) d 3.49, 13.96, 20.44, 22.65, 25.50 (t, J=23.2 Hz), 44.73, 68.86, 85.92, 105.76–124.42 (m, CF$_2$, CF$_3$), 159.13; MS m/z 1226 (M$^+$+1), 1206 (M$^+$–F), 878 (M$^+$–(CH$_2$)$_2$(CF$_2$)$_5$CF$_3$), 795, 309, 239, 195.

31. 5-Methyl-3-phenyl-5-tris[2-(perfluorohexyl)ethyl]-silanyloxymethyl-4,5-dihydroisoxazole Prepared according to general procedure 2 with the allyl silyl ether (0.098 g, 0.086 mmol), phenyl hydroximic acid chloride (53.0 mg, 0.34 mmol), and triethylamine (0.051 mL, 0.34 mmol) in CH$_2$Cl$_2$ (4 mL) to afford the isoxazoline and starting silane (ratio 97:3): IR (neat) 2934, 2915, 2363, 1443, 1361, 1316, 1238, 1206, 1144, 1121, 1074, 907, 736, 707 cm$^{-1}$; $^1$H NMR (300 MHz, CDCl$_3$) d 0.93–0.99 (m, 6 H), 1.43 (s, 3 H), 2.02–2.16 (m, 6 H), 3.03 (d, J=16.6 Hz, 1 H), 3.37 (d, J=16.6 Hz, 1 H), 3.69 (d, J=11.1 Hz, 1 H), 3.74 (d, J=11.0 Hz, 1 H), 7.37–7.42 (m, 3 H), 7.60–7.63 (m, 2 H); $^{13}$C NMR (75 MHz, CD$_3$COCD$_3$) d 3.47, 22.66, 25.45 (t, J=22.5 Hz), 42.57, 68.98, 87.86, 105.75–123.50 (m, CF$_2$, CF$_3$), 127.26, 129.50, 130.58, 131.39, 157.25; $^{19}$F NMR (470 MHz, CDCl$_3$) d (rel. to CFCl$_3$) –126.78 (t, J=4.7 Hz), −123.73, −123.51, −122.57, −116.78 (t, J=14.1 Hz), −81.43 (t, J=9.4 Hz); MS m/z 1240 (M$^+$−F), 990, 912 (M$^+$−(CH$_2$)$_2$(CF$_2$)$_5$CF$_3$), 795, 309, 239, 160.

32. 3-Methyl-5-tris[2-(perfluorohexyl)ethyl]silanyloxymethylisoxazole

Prepared according to general procedure 1 with propargyl silyl ether (0.100 g, 0.089 mmol), BTF (6 mL), nitroethane (0.064 mL, 0.89 mmol), and phenyl isocyanate (0.18 mL, 1.78 mmol) to afford the isoxazoline (105 mg, 99%): IR (neat) 2947, 2910, 1443, 1364, 1317, 1295, 1244, 1197, 1144, 1121, 1075, 904, 845, 812, 745, 736, 707 cm$^{-1}$; $^1$H NMR (300 MHz, CDCl$_3$) d 0.95–1.01 (m, 6 H), 1.99–2.17 (m, 6 H), 2.28 (s, 3 H), 4.77 (s, 2 H), 6.05 (s, 1 H); $^{13}$C NMR (75 MHz, CD$_3$COCD$_3$) d 3.37, 11.17, 25.41 (t, J=23.3 Hz), 57.61, 103.98, 105.27–124.41 (m, CF$_2$, CF$_3$), 160.53, 171.10; MS m/z 1162 (M$^+$−F), 910, 828, 506, 309, 239.

33. 3-tert-Butyl-5-tris[2-(perfluorohexyl)ethyl]silanyloxymethylisoxazole

Prepared according to general procedure 2 with propargyl silyl ether (0.100 g, 0.089 mmol), tertbutyl hydroximic acid chloride (97.0 mg, 0.72 mmol), and triethylamine (0.11 mL, 0.72 mmol) in CH$_2$Cl$_2$ (6 mL) to afford the isoxazoline (108 mg, 99%): IR (neat) 2973, 2950, 2912, 2360, 2342, 1367, 1317, 1237, 1206, 1144, 1121, 1076, 904, 812, 745, 736, 707 cm$^{-1}$; $^1$H NMR (300 MHz, CDCl$_3$) d 0.95–1.01 (m, 6 H), 1.31 (s, 9 H), 2.00–2.17 (m, 6 H), 4.77 (s, 2 H), 6.11 (s, 1 H); $^{13}$C NMR (75 MHz, CD$_3$COCD$_3$) d 3.42, 25.46 (t, J=23.3 Hz), 32.76, 57.81, 101.19, 105.78–124.00 (m, CF$_2$, CF$_3$), 170.96, 172.74; MS m/z 1209 (M$^+$−14), 1204 (M$^+$−F), 918, 871, 813, 462, 310.

34. 3-Propyl-5-tris[2-(perfluorohexyl)ethyl]silanyloxymethylisoxazole

Prepared according to general procedure 1 with propargyl silyl ether (0.100 g, 0.089 mmol), BTF (6 mL), nitrobutane (0.09 mL, 0.89 mmol), and phenyl isocyanate (0.18 mL, 1.78 mmol) to afford the isoxazoline (107 mg, 99%): IR (neat) 2972, 2945, 2912, 2883, 1443, 1362, 1317, 1294, 1237, 1209, 1144, 1121, 1075, 905, 812, 745, 736, 707 cm$^{-1}$; $^1$H NMR (300 MHz, CDCl$_3$) d 0.94–1.02 (m, 9 H), 1.64–1.71 (m, 2 H), 2.00–2.17 (m, 6 H), 2.62 (t, J=7.4 Hz, 2 H), 4.77 (s, 2 H), 6.06 (s, 1 H); $^{13}$C NMR (75 MHz, CD$_3$COCD$_3$) d 3.39, 13.91, 22.29, 25.43 (t, J=23.3 Hz), 28.54, 57.74, 102.90, 105.75–123.47 (m, CF$_2$, CF$_3$), 164.63, 171.06; MS m/z 1209 (M$^+$), 1190 (M$^+$−F), 857, 309, 239, 195.

35. 3-Phenyl-5-tris[2-(perfluorohexyl)ethyl]silanyloxymethylisoxazole

Prepared according to general procedure 2 with propargyl silyl ether (0.100 g, 0.089 mmol), phenyl hydroximic acid chloride (110 mg, 0.71 mmol), and triethylamine (0.11 mL, 0.71 mmol) in CH$_2$Cl$_2$ (6 mL) to afford the isoxazoline and silanol (40 % silanol as determined by $^1$H-NMR). $^1$H NMR (300 MHz, CDCl$_3$) d 1.00–1.06 (m, 6 H), 2.04–2.21 (m, 6 H), 4.87 (s, 2 H), 6.53 (s, 1 H), 7.45–7.47 (m, 3 H), 7.76–7.80 (m, 2 H); $^{13}$C NMR (75 MHz, CD$_3$COCD$_3$) d 3.35, 25.37 (t, J=23.3 Hz), 57.71, 101.37, 107.77–123.44 (m, CF$_2$, CF$_3$), 127.55, 129.87, 130.10, 131.01, 163.23, 172.26; MS m/z 1243 (M$^+$), 1224 (M$^+$−F), 893, 568, 309, 240, 158.

36. General Procedure for Cleavage of the Silyl Group (General Procedure 3)

The silylated isoxazol(in)e (0.079 mmol) was dissolved in Et$_2$O (THF) (3 mL) at 25° C.

HF.pyridine (0.1 mL) was added and the solution was stirred for 1 h at 25° C. After removal of the solvent the residue was dissolved in CH$_2$Cl$_2$ (20 mL). Sat. aq. HN$_4$Cl (10 mL) was added and the organic-aqueous biphase was washed twice with FC-72 (10 mL). After separation of the layers, the aqueous phase was extracted twice with CH$_2$Cl$_2$. The combined organic phases were dried (MgSO$_4$) and evaporated to yield the deprotected isoxazol(in)e. The purity was determined by GC-analysis.

37. (3-Phenyl-4,5-dihydroisoxazol-5-yl)methanol

Prepared according to general procedure 3 with isoxazoline (0.097 g, 0.078 mmol) and HF.pyridine (0.1 mL) in THF (3 mL) to afford after extraction the isoxazoline (13.6 mg, 99%) with 95% purity. The physical data are in agreement with those reported in literature.

38. (3-Methyl-4,5-dihydroisoxazol-5-yl)methanol

Prepared according to general procedure 3 with the silyl isoxazoline (0.300 g, 0.254 mmol) and HF.pyridine (0.2 mL) in Et$_2$O (6 mL) to afford after extraction the isoxazoline (8.5 mg, 29%) with 93% purity. The physical data are in agreement with those reported in literature.

39. (3-tert-Butyl-4,5-dihydroisoxazol-5-yl)methanol (13a)

Prepared according to general procedure 3 with the silyl isoxazoline (0.085 g, 0.069 mmol) and HF.pyridine (0.1 mL) in THF (3 mL) to afford after extraction the isoxazoline (10.6 mg, 99%) with 91% purity. The physical data are in agreement with those reported in literature.

40. (3-Propyl-4,5-dihydroisoxazol-5-yl)methanol (13b)

Prepared according to general procedure 3 with the silyl isoxazoline (0.096 g, 0.079 mmol) and HF.pyridine (0.1 mL) in THF (3 mL) to afford after extraction the isoxazoline (5.4 mg, 48%) with 94% purity: IR (neat) 3700–3100 br., 2962, 2935, 2875, 1462, 1435, 1383, 1361, 1334, 1313, 1096, 1074, 1049, 908, 874, 849 cm$^{-1}$; $^1$H NMR (300 MHz, CDCl$_3$) d 0.98 (t, J=7.9 Hz, 3 H), 1.54–1.66 (m, 2 H), 1.92 (s, br 1 H), 2.32 (t, J=7.4 Hz, 2 H), 2.82 (dd, J$_1$=17.0 Hz, J$_2$=7.6 Hz, 1 H), 2.96 (dd, J$_1$=17.0 Hz, J$_2$=10.7 Hz, 1 H), 3.56 (dd, J$_1$=12.1 Hz, J$_2$=4.6 Hz, 1 H), 3.77 (dd, J$_1$=12.1 Hz, J$_2$=3.1 Hz, 1 H), 4.62–4.70 (m, 1 H); $^{13}$C NMR (75 MHz, CDCl$_3$) d 13.79, 19.78, 29.61, 38.50, 63.68, 80.00, 159.66; MS m/z 143 (M$^+$), 115, 112, 84; HRMS calcd. for C$_7$H$_{13}$NO$_2$ m/z 143.0946, found 143.0943.

41. (3,5-Dimethyl-4,5-dihydroisoxazol-5-yl)methanol (13d)

Prepared according to general procedure 3 with the silyl isoxazoline (0.120 g, 0.100 mmol) and HF.pyridine (0.1 mL) in THF (3 mL) to afford after extraction the isoxazoline (4 mg, 31%) with 99% purity: IR (CHCl$_3$) 3588, 2976, 2954, 2925, 2874, 1431, 1388, 1353, 1334, 1241, 1222, 1178, 1055 cm$^{-1}$; $^1$H NMR (300 MHz, CDCl$_3$) d 1.31 (s, 3 H), 1.95 (s, 3 H), 2.55 (s, br 1 H), 2.58 (d, J=17.0 Hz, 1 H), 3.04 (dd, J$_1$=17.0 Hz, J$_2$=0.9 Hz, 1 H), 3.44 (d, J=12.0 Hz, 1 H), 3.61 (d, J=11.9 Hz, 1 H); $^{13}$C NMR (75 MHz, CDCl$_3$) d 13.59, 22.73, 45.92, 67.46, 86.36, 156.29; MS m/z 129 (M$^+$), 98, 74, 59; HRMS calcd. for C$_6$H$_{11}$NO$_2$ m/z 129.0790, found 129.0790.

42. (3-tert-Butyl-5-methyl-4,5-dihydroisoxazol-5-yl)methanol

Prepared according to general procedure 3 with the silyl isoxazoline (0.113 g, 0.091 mmol) and HF.pyridine (0.1 mL) in Et$_2$O (3 mL) to afford after extraction the isoxazoline (15.6 mg, 99%) with 99% purity: IR (neat) 3700–3100 br., 2968, 2931, 2871, 2361, 2342, 1479, 1462, 1434, 1395, 1367, 1340, 1260, 1244, 1205, 1126, 1056, 895, 797 cm$^{-1}$; $^1$H NMR (300 MHz, CDCl$_3$) d 1.19 (s, 9 H), 1.31 (s, 3 H), 1.98 (s, br 1 H), 2.62 (d, J=16.7 Hz, 1 H), 3.08 (d, J=16.7 Hz, 1 H), 3.46 (d, J=12.0 Hz, 1 H), 3.62 (d, J=11.8 Hz, 1 H); $^{13}$C NMR (75 MHz, CDCl$_3$) d 22.56, 28.21, 33.36, 41.59, 67.49, 86.20, 167.03; MS m/z 171 (M$^+$), 140, 98, 82; HRMS calcd. for C$_9$H$_{17}$NO$_2$ m/z 171.1259, found 171.1253.

43. (5-Methyl-3-propyl-4,5-dihydroisoxazol-5-yl) methanol

Prepared according to general procedure 3 with the silyl isoxazoline (0.062 g, 0.051 mmol) and HF.pyridine (0.1 mL) in Et$_2$O (3 mL) to afford after extraction the isoxazoline (8 mg, 99%) with 99% purity: IR (neat) 3700–3100 br., 2963, 2929, 2874, 2855, 1457, 1434, 1378, 1363, 1336, 1317, 1236, 1054, 909 cm$^{-1}$; $^1$H NMR (300 MHz, CDCl$_3$) d 0.95 (t, J=7.4 Hz, 3 H), 1.32 (s, 3 H), 1.58 (q, J=7.5 Hz, 2 H), 1.97 (s, br 1 H), 2.29 (t, J=7.6 Hz, 2 H), 2.58 (d, J=17.0 Hz, 1 H.), 3.04 (d, J=17.0 Hz, 1 H), 3.46 (d, J=11.9 Hz, 1 H), 3.63 (d, J=11.9 Hz, 1 H); $^{13}$C NMR (75 MHz, CDCl$_3$) d 13.92, 19.94, 22.79, 30.03, 44.27, 67.59, 85.93, 159.97; MS m/z 157 (M$^+$), 126, 97; HRMS calcd. for C$_8$H$_{15}$NO$_2$ m/z 157.1103, found 157.1099.

44. (5-Methyl-3-phenyl-4,5-dihydroisoxazol-5-yl) methanol

Prepared according to general procedure 3 with the silyl isoxazoline (0.080 g, 0.064 mmol) and HF.pyridine (0.1 mL) in THF (3 mL) to afford after extraction the isoxazoline (11.5 mg, 95%) with 98% purity. The physical data are in agreement with those reported in literature.

45. (3-tert-Butylisoxazol-5-yl)methanol

Prepared according to general procedure 3 with the silyl isoxazole (0.099 g, 0.073 mmol, around 10% of silanol) and HF.pyridine (0.1 mL) in Et$_2$O (3 mL) to afford after extraction the isoxazole (11.4 mg, 99%) with 99% purity: IR (neat) 3700–3100 br., 2966, 2935, 2910, 2872, 1607, 1488, 1465, 1409, 1367, 1211, 1193, 1068, 1042, 998 cm$^{-1}$; $^1$H NMR (300 MHz, CDCl$_3$) d 1.31 (s, 9 H), 2.57 (s, br 1 H), 4.71 (s, 2 H), 6.15 (s, 1 H); $^{13}$C NMR (75 MHz, CDCl$_3$) d 29.63, 32.22, 56.67, 100.03, 171.09, 172.36; MS m/z 155 (M$^+$), 140, 124, 94, 68, 57; HRMS calcd. for C$_8$H$_{13}$NO$_2$ m/z 155.0946, found 155.0939.

46. (3-Propylisoxazol-5-yl)methanol (13c)

Prepared according to general procedure 3 with the silyl isoxazole (0.102 g, 0.076 mmol, around 10% of silanol) and HF.pyridine (0.1 mL) in Et$_2$O (3 mL) to afford after extraction the isoxazole (10,7 mg, 99%) with 97% purity. The physical data are in agreement with those reported in literature.

47. (3-Methylisoxazol-5-yl)methanol

Prepared according to general procedure 3 with the silyl isoxazole (0.098 g, 0.075 mmol, around 10% of silanol) and HF.pyridine (0.1 mL) in Et$_2$O (3 mL) to afford after extraction the isoxazole (8.5 mg, 99%) with 99% purity. The physical data are in agreement with those reported in literature.

48. (3-Phenylisoxazol-5-yl)methanol

Prepared according to general procedure 3 with the silyl isoxazole (0.05 g, 0.04 mmol) and HF.pyridine (0.1 mL) in Et$_2$O (3 mL) to afford after extraction the isoxazole (6.8 mg, 99%) with 98% purity. The physical data are in agreement with those reported in literature.

49. Simulated Combinatorial Synthesis without Characterization of Intermediates 50. (3-tert-Butyl-4,5-dihydroisoxazol-5-yl)methanol (13a)

The allyl silyl ether 11 was prepared as described before with 0.65 mmol of bromo tris[2-(perfluorohexyl)ethyl]silane 9. Cycloaddition according to general procedure 2 with tert-butyl hydroxamic acid chloride (440 mg, 3.20 mmol), and triethylamine (0.48 mL, 3.20 mmol) in CH$_2$Cl$_2$ (20 mL) afforded the isoxazoline. Silyl cleavage according to general procedure 3 with HF.pyridine (0.5 mL) in Et$_2$O (20 mL) afforded after extraction the isoxazoline (68 mg, 66%) with 99% purity.

51. (3-Propyl-4,5-dihydroisoxazol-5-yl)methanol (13b)

The allyl silyl ether was prepared as described before with 0.38 mmol of bromo tris[2-(perfluorohexyl)ethyl]silane 9. Cycloaddition according to general procedure 1 with nitrobutane (0.38 mL, 3.80 mmol) and phenyl isocyanate (0.73 mL, 7.20 mmol) in BTF (15 mL) afforded the isoxazoline. Silyl cleavage according to general procedure 3 with HF.pyridine (0.4 mL) in Et$_2$O (12 mL) afforded after extraction the isoxazoline (39.5 mg, 73%) with 94% purity.

52. (3,5-Dimethyl-4,5-dihydroisoxazol-5-yl)methanol (13d)

The allyl silyl ether was prepared as described before with 0.38 mmol of bromo tris[2-(perfluorohexyl)ethyl]silane 9. Cycloaddition according to general procedure 1 with nitro ethane (0.27 mL, 3.80 mmol) and phenyl isocyanate (0.73 mL, 7.20 mmol) in BTF (15 mL) afforded the isoxazoline. Silyl cleavage according to general procedure 3 with HF.pyridine (0.4 mL) in Et$_2$O (12 mL) afforded after extraction the isoxazoline (15.5 mg, 32%) with 99% purity.

53. (3-Propylisoxazol-5-yl)methanol (13c)

Silyl propargyl ether was prepared as described before with 0.31 mmol of bromo tris[2-(perfluorohexyl)ethyl]silane 9. Cycloaddition according to general procedure 1 with nitrobutane (0.31 mL, 3.10 mmol) and phenyl isocyanate (0.63 mL, 6.20 mmol) in BTF (15 mL) afforded the isoxazole. Silyl cleavage according to general procedure 3 with HF.pyridine (0.5 mL) in Et$_2$O (10 mL) afforded after extraction the isoxazoline (37.3 mg, 83%) with 97% purity.

54. erythro/threo-a-Methyl-3-phenyl-2-isoxazoline-5-methanol (13e)

rac-3-Buten-2-ol (0.083 mL, 0.960 mmol) and triethylamine (0.14 mL, 0.96 mmol) were dissolved in dry THF (4 mL) under argon. A mixture of bromo tris [2-(perfluorohexyl)ethyl]silane 9 (275 mg, 0.24 mmol) in THF (2 mL) was slowly added to the above solution at 25° C. The resulting suspension was stirred at 25° C. for 3 h. Workup as described for the preparation of the allyl silyl ether afforded crude rac-tris[2-(perfluorohexyl)ethyl]-(1-methyl-allyloxy) silane. Cycloaddition according to general procedure 2 with rac-tris[2-(perfluorohexyl)ethyl]-(1-methylallyloxy)silane (100 mg) and phenyl hydroximic acid chloride (53 mg, 0.35 mmol), and triethylamine (0.055 ml, 0.37 mmol) in CH$_2$Cl$_2$ (6 mL) afforded the isoxazoline. Silyl cleavage according to general procedure 3 with HF.pyridine (0.5 mL) in Et$_2$O (20 mL) afforded after extraction erythro/threo-a-methyl-3-phenyl-2-isoxazoline-5-methanol (10.4 mg, 62%) as a 70:30 diastereoisomer mixture with 97% purity. The diastereoisomer ratio was determined by $^1$H NMR analysis.

55. Fluorous Phase Switch. Representative Experimental Procedure for Grignard Reaction/Silylation The Grignard reagent (3M in ether, 0.75 mmol, 0.25 mL) was added at 0° C. to a solution of the carbonyl derivative (0.5 mmol) in dry THF (5 mL). The mixture was stirred 15 min at 0° C. and then 30 min at 25° C. Bromo tris[2-(perfluorohexyl)ethyl]silane (9) (1 mmol, containing about 10–15% C$_6$F$_{13}$(CH$_2$)$_4$C$_6$F$_{13}$) in FC-72 (6 mL) was added at 25° C. to the mixture. After 14 h, the residue obtained by evaporation was extracted with water (20 mL), chloroform (20 mL) and FC-72 (1×15 mL and 2×10 mL) in a triphasic extraction. After separation of the chloroform extract, the remaining aqueous phase was washed with chloroform (1×10 mL). The combined organic phases (CHCl$_3$) were dried (MgSO$_4$) and evaporated. The resulting residue was taken up in acetonitrile (15 mL) and washed with FC-72 (1×10 mL then 2×5 mL) in a biphasic extraction. The fluorous phases were combined (from triphasic and biphasic extraction) and evaporated, and the residue was diluted with 1:1 THF:benzotrifluoride (10 mL). KHCO$_3$ (100 mg) and cesium fluoride (2 mmol, 2 mL in MeOH 1M) were added at 25° C., and the mixture was stirred for 2 h. The residue obtained after evaporation was extracted with water (20 mL), FC-72 (20 mL) and chloroform (3×15 mL). The fluorous phase was washed with acetonitrile (1×10 mL). The combined organic (chloroform and acetonitrile) phases were dried (MgSO$_4$) and evaporated. The residue was diluted with acetonitrile (15 mL) and this was washed with FC-72 (1×10 mL then 2×5 ml). The acetonitrile solution was evaporated and the corresponding alcohols 15 were obtained. All the alcohols are known compounds.

56. Fluorous Tagging of Biproducts General Procedure for Radical Addition and Hydrostannylation A suspension of 1-iodoadamantane (26.2 mg, 0.1 mmmol), benzyl acrylate (81.1 mg, 0.5 mmol), tris(2-perfluorohexylethyl)tin hydride (3) (11.6 mg, 0.01 mmol), sodium cyanoborohydride (9.6 mg, 0.13 mmol), and cat. AIBN in BTF (0.5 mL) and t-butanol (0.5 mL) was heated at reflux under nitrogen for 12 h. After cooling, a mixture of tris (2-perfluorohexylethyl)tin hydride (696 mg, 0.6 mmol) and cat. AIBN in BTF (0.2 mL) was added to the reaction mixture. Then, the mixture was heated at 90° C. under nitrogen for 24 h. After cooling, the reaction mixture was dissolved in chloroform (10 mL) and extracted with FC-72 (10 mL) three times. The organic layer was filtered through neutral alumina and evaporated under reduced pressure to give the product (246 mg, 82%) free of alkene.

57. General Procedure for 1,3-Dipolar Cycloaddition and Hydrostannylation

To a solution of styrene (31.3 mg, 0.3 mmol) and triethylamine (12.1 mg, 0.13 mmol) in dichloromethane (1 mL) was added dropwise tert-butyl hydroximic acid chloride (13.6 mg, 0.1 mmol) diluted with dichloromethane (1 mL) at 25° C. The mixture was stirred for 12 h. After evaporating the solvent, tris(2-perfluorohexylethyl)tin hydride 3 (348 mg, 0.3 mmol) and cat. AIBN dissolved in BTF (1 mL) were added to the crude residue and the mixture was heated at 90° C. under nitrogen for 24 h. After cooling, the reaction mixture was diluted with dichloromethane (10 mL) and this was extracted with FC-72 (10 mL) three times. The organic layer was evaporated under reduced pressure to give the product (20 mg, 99%) free of alkene.

58. Tris (2-(perfluorohexyl)ethyl)tin azide (16); Tris (3,3,4,4,5,5,6,6,7,7,8,8,8-tridecafluorooctyl)tin azide To a solution of tris(2-(perfluorohexyl)ethyl)tin bromide (2) (10 g, 8.06 mmol) in ether (14 mL) was added a solution of sodium azide (629 mg, 9.67 mmol) in water (2 mL) and the resulting biphasic mixture was stirred at 25° C. for 12 h. Ether (20 mL) and water (20 mL) were added to the reaction mixture. The two layers were separated and the ethereal phase was washed with water (3×20 mL), and dried over anhydrous MgSO$_4$. The solvent was evaporated to dryness to yield the tin azide (9.4 g, 97% yield) as a colorless oil: IR (thin film) 2080, 1360, 734 cm$^{-1}$; $^1$H NMR (CDCl$_3$) d 2.48 (m, 6 H), 1.51 (m. 6 H); $^{119}$Sn NMR (BTF-C$_6$D$_6$) d 11.53

59 Representative Experimental Procedure for the Preparation of 5-Substituted Tetrazoles 19

A solution of tris (2-(perfluorohexyl)ethyl)tin azide 16 (0.5 g, 0.416 mmol) and p-tolunitrile (97.5 mg, 0.832 mmol) in benzotrifluoride (BTF, 0.84 mL) was heated in a sealed tube at 80° C. for 12 h. The BTF was evaporated and the crude product was partitioned between benzene and FC-72 (10 mL each). After separation of the 2 layers, the benzene layer was washed twice with FC-72 (10 mL). Evaporation of the benzene phase yielded the unreacted p-tolunitrile. The fluorinated phase was evaporated and a saturated solution of HCl in ether (10 mL) was added to the residue. The mixture was stirred for 12 h at 25° C. After evaporation of the ether, the residue was dissolved in FC-72 and acetonitrile (10 mL of each). After separation of the two layers, the organic phase was washed with FC-72 (3×10 mL). Evaporation of the acetonitrile phase yielded the 5-p-tolyltetrazole (41 mg, 61% yield), which was identified by comparing physical and spectral data with those of the authentic sample. (The other tetrazoles prepared are also known compounds.) The FC-72 phase was evaporated as well yielding tris (2-(perfluorohexyl)ethyl)tin chloride 8 (449 mg, 90%) as a colorless oil.

60. tris[2- (Perfluorodecyl)ethyl]silane

Magnesium powder (0.45 g, 18.5 mmol) was suspended in dry Et$_2$O (20 mL) and 1-iodo-1H,1H,2H,2H-perfluorododecane (0.50 g, 0.77 mmol) was added. The resulting suspension was sonicated for 30 minutes. A solution of 1-iodo-1H,1H,2H,2H-perfluorododecane (9.50 g, 14.7 mmol) in Et$_2$O (70 mL) was slowly added. The mixture was heated at reflux for 2 h. Trichlorosilane (0.40 mL, 3.87 mmol) was slowly added and the reaction mixture was stirred under reflux for 16 h. After cooling to 25° C., sat. aq. NH$_4$Cl and CH$_2$Cl$_2$ were added. The cloudy biphase was extracted 5 times with FC-72. Evaporation of the combined fluorous extracts yielded the crude product as a white solid. Removal of the impurity (dimer, Wurtz coupling product) by bulb-to-bulb distillation (0.5 Torr, 210° C.) yielded tris[2-(perfluorodecyl)ethyl]silane as a white solid (4.7 g, 76%): mp 76–78° C.; IR (FC-72) 2977, 2950, 2914, 2873, 2136, 1444, 1426 cm$^{-1}$; $^1$H NMR (300 MHz, FC-72 with benzene as internal lock) d 1.15–1.22 (m, 6 H), 2.24–2.41 (m, 6 H), 4.14 (s, 1 H).

61. Bromo tris[2-(perfluorodecyl)ethyl]silane tris[2-(Perfluorodecyl)ethyl]silane (0.56 g, 0.34 mmol) was dissolved under argon in FC-72 (10 mL). Bromine (0.03 mL, 0.50 mmol) was added and the mixture was stirred at 25° C. for 12 h. FC-72 (40 mL) was added and the fluorous phase was washed with CH$_2$Cl$_2$. Evaporation of the fluorous layer yielded bromo tris[2-(perfluorodecyl)ethyl]silane as a white solid (586 mg, 99%): mp 80–81° C.; IR (FC-72) 2980, 2953, 2907, 2847, 1444, 1423 cm$^{-1}$; $^1$H NMR (300 MHz, FC-72 with benzene as internal lock) d 1.41–1.55 (m, 6 H), 2.33–2.44 (m, 6 H).

62. Tripropyl 4-Bromoorthothiobenzoate:

4-Bromobenzoic acid (2.00 g, 9.95 mmol) was suspended in thionyl chloride (3 mL, 41.2 mmol) and heated at reflux for 60 min. Removal of the excess thionyl chloride and vacuum drying provided 4-bromobenzoyl chloride as a colorless solid. Propanethiol (10 mL, 109 mmol) was slowly added to a mixture of 4-bromobenzoyl chloride and anhydrous AlCl$_3$ (5.30 g, 39.7 mmol). The mixture was heated at 60° C. for 48 h, cooled, and poured slowly with stirring into ice-cooled 4N aqueous NaOH (75 ml). Extraction with ether and washing of the organic phase with brine afforded after drying (MgSO$_4$) the crude product as a red oil. Purification by flash-column chromatography (SiO$_2$, hexanes containing 1% of NEt$_3$) provided the orthothiobenzoate as a colorless oil (1.78 g, 45%): IR (neat) 2962, 2929, 2871, 1582, 1483, 1456, 1391, 1378, 1337, 1291, 1237, 1076, 1008 cm$^{-1}$; $^1$H NMR (300 MHz, CDCl$_3$) d 0.93 (t, J=7.3 Hz, 9 H), 1.48–1.55 (m, 6 H), 2.54 (t J=7.3 Hz, 6 H), 7.43 (d, J=8.7 Hz, 2 H), 7.73 (d, J=8.7 Hz, 2 H); $^{13}$C NMR (75 MHz, CDCl$_3$) d 13.80, 21.80, 33.82, 72.87, 121.53, 129.68, 130.94, 141.33. MS m/z 351 (M$^+$–propyl), 349, 319 (M$^+$–S(CH$_2$)$_2$CH$_3$), 317, 201, 109; HRMS calcd. for C$_{13}$H$_{18}$S$_2$$^{81}$Br (M$^+$–S(CH$_2$)$_2$CH$_3$) m/z 319.0013, found 319.0000.

63. 4-tris[2-(Perfluorodecyl)ethyl]silyl-thiobenzoic S-Propyl Ester 22

Tripropyl 4-bromoorthothiobenzoate (250 mg, 0.66 mmol) was dissolved in Et$_2$O (7.5 mL) and cooled to −78° C. under argon. t-BuLi (1.7 molar in pentane, 0.82 mL, 1.39 mmol) was slowly added and the resulting yellow solution was stirred at that temperature for 45 min. The yellow aryllithium solution was then transferred via canula to a 25° C. mixture of bromo tris[2-(perfluorodecyl)ethyl]silane (500 mg, 0.29 mmol) in BTF (15 mL) and FC-72 (2.5 mL). The reaction mixture was stirred at 25° C. for 30 min. After addition of H$_2$O, the reaction mixture was extracted three times with CH$_2$Cl$_2$. The combined organic layers were dried (MgSO$_4$) and evaporated to afford an oil which was taken up into FC-72 and washed with benzene. The benzene layer was additionally extracted twice with FC-72. The combined fluorous layers were evaporated to yield the crude orthothioester which was dissolved in BTF (7.5 mL), THF (7.5 mL), acetone (5 mL), and H$_2$O (0.5 mL) at 25° C. AgNO$_3$ (135 mg, 0.80 mmol) was added and the resulting suspension was stirred at 25° C. for 12 h. After filtration and evaporation of the filtrate, the crude product was purified by flash-column chromatography (SiO$_2$, Et$_2$O/hexanes; 1/40) to afford 4-tris[2-(perfluorodecyl)ethyl]silylthiobenzoic S-propyl ester as a colorless solid (319 mg, 60%): mp 69–71° C.; IR (CHCl$_3$) 2970, 2935, 1668, 1246, 1193, 1157; $^1$H NMR (300 MHz, CDCl$_3$) d 1.04 (t, J=7.3 Hz, 3 H), 1.15–1.21 (m, 6 H), 1.68–1.75 (m, 2 H), 1.94–2.06 (m, 6 H), 3.08 (t, J=7.1 Hz, 2 H), 7.54 (d, J=8.0 Hz, 2 H), 8.03 (d, J=8.0 Hz, 2 H); $^{13}$C NMR (125 MHz, CDCl$_3$, 30° C.) d 1.60, 13.43, 23.00, 25.60 (t, J=23.0 Hz), 31.19, 108.45–118.40 (m, CF$_2$, CF$_3$), 127.23, 133.99, 137.79, 139.27, 191.85.

64. 4-tris[2-(Perfluorodecyl)ethyl]silyl-benzoic acid 20

4-tris[2-(Perfluorodecyl)ethyl]-silyl-thiobenzoic S-propyl ester (210 mg, 0.11 mmol) was dissolved in FC-72 (15 mL). Bromine (0.05 mL, 0.83 mmol) was added at 25° C. and the mixture was stirred for 3 h. After addition of FC-72 (15 mL) and washing with CH$_2$Cl$_2$, the fluorous layer was evaporated to afford 4-tris[2-(perfluorodecyl)ethyl]silylbenzoic acid bromide as a colorless solid. The acid bromide was dissolved in THF (12 mL) and BTF (3 mL). H$_2$O (1.5 mL) was added and the solution was stirred at 25° C. for 12 h. Evaporation of the solvents afforded 4-tris[2-(perfluorodecyl)ethyl]silylbenzoic acid as a colorless solid (196 mg, 97%). mp 134–136° C.; $^1$H NMR (300 MHz, TFA-d) d 1.35–1.39 (m, 6 H), 2.10–2.35 (m, 6 H), 7.78 (d, J=8.1 Hz, 2 H), 8.27 (d, J=7.9 Hz, 2 H); $^{13}$C NMR (75 MHz, TFA-d) d 2.95, 27.42, 105–120 (m, CF$_2$, CF$_3$), 131.78, 132.05, 136.15, 142.95, 175.38. MS (EI) m/z 1243 (M$^+$–CH$_2$CH$_2$(CF$_2$)$_9$CF$_3$), 706, 601, 474, 423, 378, 175.

65. General Procedure for the Ugi-Four-Component-Condensation 4-tris[2-(Perfluorodecyl)ethyl]silylbenzoic acid (20) (26.2 mg, 0.015 mmol), the amine (0.25 mmol), the aldehyde (0.25 mmol), and the isocyanide (0.25 mmol) were added to a sealed tube with CF$_3$CH$_2$OH (0.3 mL). (For some examples, the preformed imine was used.) The suspension was heated under argon to 90° C. for 48 h. After removal of the solvent, the residue was dissolved in FC-72 (15 mL) and washed with benzene (15 mL). The benzene layer was additionally washed twice with FC-72 (15 mL). The combined fluorous phases were evaporated to yield the perfluorosilylated amino acid amide. For desilylation the amino acid amide was dissolved at 25° C. in THF (2 mL), TBAF (1 molar in THF, 0.022 mL, 0.022 mmol) was added and the resulting solution was stirred at 25° C. for 30 min. After removal of the solvent, the residue was taken up into benzene (30 mL) and washed twice with FC-72 (15 mL). Et$_2$O (30 mL) was added to the organic layer which was washed with 0.1N HCl, sat. aq. Na$_2$CO$_3$, and brine (15 mL each). The organic phase was dried (MgSO$_4$) and evaporated to yield the benzoylated amino acid amide. The purity was checked by GC-analysis.

66. N-Benzoyl-N-benzyl-phenylglycine-tert-butylamide

Prepared according to the general procedure with the acid (20) (26.2 mg, 0.015 mmol), benzyl benzylidene amine (51 mg, 0.25 mmol), and tert-butyl isocyanide (30 mL, 0.25 mmol) to afford the silylated amino acid: IR (CHCl$_3$) 1684, 1631, 1518, 1240, 1218, 1157 cm$^{-1}$; $^1$H NMR (300 MHz, CDCl$_3$) d 1,14 (s, br. 6 H), 1.34 (s, 9 H), 1.90–2.20 (br. 6 H), 4.35–4.50 (br. 1 H), 4.71 (d, J=17.6, 1 H), 5.52 (s, 1 H), 5.63 (s, 1 H), 6.91 (s, br. 2 H), 7.26 (s, br. 4 H), 7.30–7.49 (m, 8 H); $^{13}$C NMR (75 MHz, CDCl$_3$) d 1.50, 25.54, 28.75, 51.93, 105–125 (m, CF$_2$, CF$_3$), 127.08, 127.15, 127.24, 128.45, 128.95, 129.15, 129.25, 129.98, 137.63, 138.89, 168.42, 172.70. Desilylation as described in the general procedure in THF (2 mL) with TBAF (0.022 mL, 0.022 mmol) afforded N-benzoyl-N-benzyl-phenylglycine-tert-butylamide (5.0 mg, 83%) with 85% purity: IR (CHCl$_3$) 3424, 3066, 3032, 2969, 2934, 2907, 2246, 1681, 1635, 1514, 1496, 1453, 1430,1409 cm$^{-1}$; $^1$H NMR (300 MHz, CDCl$_3$) d 1.30 (s, 9 H), 4.47 (s, br. 1 H), 4.73 (d, J=16.4 Hz, 1 H), 5.46 (s, 1 H), 5.40–5.75 (s, br. 1 H), 7.03 (s, br. 2 H), 7.13–7.16 (m, 4 H), 7.26–7.49 (m, 9 H); $^{13}$C NMR (75 MHz, CDCl$_3$) d 28.67, 51.74, 126.79, 127.02, 128.41, 128.66, 128.92, 129.73, 129.90, 135.33, 136.46, 168.53, 173.38; MS m/z 328 (M$^+$–NHC(CH$_3$)$_3$), 300 (M$^+$–CONHC(CH$_3$)$_3$), 210, 191, 105, 91, 77; HRMS calcd. for C$_{21}$H$_{18}$NO (M$^+$–CONHC(CH$_3$)$_3$) m/z 300.1388, found 300.1389.

67. N-Benzoyl-N-benzyl-4-methoxyphenylglycine-tert-butylamide

Prepared according to the general procedure with the acid 20 (26.1 mg, 0.015 mmol), benzyl amine (27 mL, 0.25 mmol), anisaldehyde (30 mL, 0.25 mmol), and tert-butyl isocyanide (30 mL, 0.25 mmol) to afford after desilylation N-benzoyl-N-benzyl-4-methoxyphenylglycine-tert-butylamide (5.1 mg, 81%) with 87% purity: IR (CHCl$_3$) 3423, 3066, 3031, 2968, 2937, 2911, 2246, 1681, 1633, 1581, 1512, 1455, 1412, 1395, 1366, 1339, 1306, 1252, 1224, 1179, 1033 cm$^{-1}$; $^1$H NMR (300 MHz, CDCl$_3$) d 1.30 (s, 9 H), 3.77 (s, 3 H), 4.43 (s, br. 1 H), 4.72 (d, J=16.4 Hz, 1 H), 5.43 (s, 1 H), 5.40–5.70 (s, br. 1 H), 6.79 (d, J=8.3 Hz, 2 H), 7.02–7.47 (m, 12 H); $^{13}$C NMR (75 MHz, CDCl$_3$) d 28.70, 51.67, 55.42, 114.24, 126.77, 126.92, 127.25, 128.35, 128.58, 129.79, 131.18, 136.60, 159.76, 168.84, 173.28; MS m/z 430 (M+), 358 (M$^+$–NHC(CH$_3$)$_3$), 330 (M$^+$–CONHC (CH$_3$)$_3$), 240, 224, 105, 91, 77; HRMS calcd. for C$_{22}$H$_{20}$NO$_2$ (M$^+$–CONHC(CH$_3$)$_3$) m/z 330.1494, found 330.1498.

68. N-Benzoyl-N-benzylcyclohexylglycine-tert-butylamide

Prepared according to the general procedure with the acid (20) (24.0 mg, 0.013 mmol), benzyl amine (27 mL, 0.25 mmol), cyclohexane carboxaldehyde (30 mL, 0.25 mmol), and tert-butyl isocyanide (30 mL, 0.25 mmol) to afford after desilylation N-benzoyl-N-benzyl-cyclohexylglycine-tert-butylamide (1.7 mg, 32%) with 89% purity: mp 140–141° C.; IR (CHCl$_3$) 2964, 2935, 2858, 2249, 1674, 1618, 1510, 1452, 1363 cm$^{-1}$; $^1$H NMR (300 MHz, CDCl$_3$) d 0.90–2.00 (m, 10 H), 1.31 (s, 9 H), 2.38 (m, 1 H), 4.14 (d, J=10.5 Hz, 1 H), 4.44 (d, J=16.1 Hz, 1 H), 4.70 (d, J=16.1 Hz, 1 H), 5.30 (s, br. 1 H), 6.90–7.50 (m, 10 H); $^{13}$C NMR (75 MHz, CDCl$_3$) d 25.06, 25.88, 26.49, 28.80, 29.77, 30.32, 36.50, 51.19, 52.65, 126.72, 127.25, 127.64, 128.31, 128.53, 129.74, 136.99, 137.41, 169.42, 173.99; MS m/z 406 (M+), 306 (M$^+$−CONHC(CH$_3$)$_3$), 216, 197, 105, 91, 77; HRMS calcd. for C$_{26}$H$_{34}$N$_2$O$_2$ m/z 406.2620, found 406.2635.

69. N-Benzoyl-N-propyl-cyclohexylglycine-cyclohexylamide

Prepared according to the general procedure with the acid (20) (26.4 mg, 0.015 mmol), propyl amine (21 mL, 0.25 mmol), cyclohexane carboxaldehyde (30 mL, 0.25 mmol), and cyclohexyl isocyanide (31 mL, 0.25 mmol) to afford after desilylation N-benzoyl-N-propyl-cyclohexylglycine-cyclohexylamide (5.7 mg, 99%) with >95% purity: mp 110–112° C.; IR (CHCl$_3$) 2934, 2856, 2244, 1660, 1613, 1578, 1529, 1450, 1419, 1352 cm$^{-1}$; $^1$H NMR (300 MHz, CDCl$_3$) d 0.61 (t, J=7.3 Hz, 3 H), 0.85–1.84 (m, 22 H), 2.39 (m, 1 H), 3.20 (m, 2 H), 3.75–3.78 (m, 1 H), 4.00 (s, br. 1 H), 7.34–7.43 (m, 5 H); $^{13}$C NMR (75 MHz, CDCl$_3$) d 11.21, 22.59, 24.71, 25.79, 26.50, 29.69, 30.47, 32.79, 32.97, 35.53, 47.75, 126.64, 128.61, 129.76, 136.96, 170.27, 173.70; MS m/z 384 (M$^+$), 258 (M$^+$−CONHC$_6$H$_{11}$), 223, 105, 77; HRMS calcd. for C$_{24}$H$_{36}$N$_2$O$_2$ m/z 384.2777, found 384.2781.

70. N-Benzoyl-N-benzylphenylglycine-cyclohexylamide

Prepared according to the general procedure with the acid (20) (27.1 mg, 0.015 mmol), benzyl benzylidene amine (51 mg, 0.25 mmol), and cyclohexyl isocyanide (31 mL, 0.25 mmol) to afford after desilylation N-benzoyl-N-benzyl-phenylglycine-cyclohexylamide (5.2 mg, 92%) with 80% purity: IR (CHCl$_3$) 3422, 3066, 3031, 2935, 2857, 2246, 1673, 1634, 1603, 1515, 1497, 1452, 1431, 1411, 1349, 1313, 1253 cm$^{-1}$; $^1$H NMR (300 MHz, CDCl$_3$) d 1.07–2.20 (m, 10 H), 3.83 (m, br. 1 H), 4.47 (s, br. 1 H), 4.70 (s, br. 1 H), 5.47 (s, 1 H), 5.67 (s, br. 1 H), 7.12–7.49 (m, 15 H); $^{13}$C NMR (75 MHz, CDC13) d 24.91, 25.60, 32.84, 48.71, 126.83, 127.15, 128.51, 128.73, 128.99, 129.73, 129.96, 135.24, 136.34, 168.39, 173.36; MS m/z 321 (M$^+$−PhCO), 300 (M$^+$−CONHC$_6$H$_{11}$), 217, 210, 105, 91, 77; HRMS calcd. for C$_{21}$H$_{18}$NO (M$^+$−CONHC$_6$H$_{11}$) 300.1388, found 300.1398.

71. N-Benzoyl-N-propylvaline-cyclohexylamide

Prepared according to the general procedure with the acid 20 (25.8 mg, 0.014 mmol), propyl amine (21 mL, 0.25 mmol), isobutyraldehyde (23 mL, 0.25 mmol), and cyclohexyl isocyanide (31 mL, 0.25 mmol) to afford after desilylation N-benzoyl-N-propylvaline-cyclohexylamide (3.5 mg, 71%) with >95% purity. The physical data are in agreement with those reported in literature.

72. N-Benzoyl-N-benzylvaline-cyclohexylamide

Prepared according to the general procedure with the acid (20) (26.1 mg, 0.015 mmol), benzyl amine (27 mL, 0.25 mmol), isobutyraldehyde (23 mL, 0.25 mmol), and cyclohexyl isocyanide (31 mL, 0.25 mmol) to afford after desilylation N-benzoyl-N-benzylvaline-cyclohexylamide (3.5 mg, 61%) with >95% purity: mp 131–133° C.; IR (CHCl$_3$) 3423, 3303, 3064, 3029, 2970, 2931, 2860, 2242, 1665, 1617, 1518, 1450, 1340, 1309 cm$^{-1}$; $^1$H NMR (300 MHz, CDCl$_3$) d 0.78–1.37 (m, 11 H), 1.51–1.79 (m, 5 H), 2.69 (m, br. 1 H), 3.63 (m, br. 1 H), 4.16 (d, J=10.6 Hz, 1 H), 4.44 (d, J=15.8 Hz, 1 H), 4.67 (d, J=15.9 Hz, 1 H), 6.93 (s, br. 2 H), 7.11–7.26 (m, 7 H); $^{13}$C NMR (75 MHz, CDCl$_3$) d 19.39, 19.91, 24.63, 25.53, 27.24, 32.58, 32.87, 47.76, 52.54, 68.17, 126.57, 127.20, 127.49, 128.17, 128.42, 129.64, 136.79, 137.08, 169.27, 173.92; MS m/z 287 (M$^+$−PhCO), 266 (M$^+$−CONHC$_6$H$_{11}$), 211, 183, 105, 91, 77; HRMS calcd. for C$_{18}$H$_{27}$N$_2$O (M$^+$−PhCO) m/z 287.2123, found 287.2128.

73. N-Benzoyl-N-benzyl-cyclohexylglycine-cyclohexylamide

Prepared according to the general procedure with the acid (20) (26.2 mg, 0.015 mmol), benzyl amine (27 mL, 0.25 mmol), cyclohexane carboxaldehyde (30 mL, 0.25 mmol), and cyclohexyl isocyanide (31 mL, 0.25 mmol) to afford after desilylation N-benzoyl-N-benzylcyclohexylglycine-cyclohexylamide (5.3 mg, 84%) with >95% purity: mp 181–182° C. IR (CHCl$_3$) 2933, 2856, 2246, 1671, 1620, 1515, 1451, 1415, 1351, 1329 cm$^{-1}$; $^1$H NMR (300 MHz, CDCl$_3$) d 0.85–1.84 (m, 20 H), 2.41 (m, 1 H), 3.65–3.71 (m, 1 H), 4.15 (d, J=11.0 Hz, 1 H), 4.45 (d, J=15.8 Hz, 1 H), 4.67 (d, J=15.9 Hz, 1 H), 4.92 (s, br. 1H), 6.96 (s, br. 2 H), 7.15–7.43 (m, 8 H); $^{13}$C NMR (75 MHz, CDCl$_3$) d 24.72, 25.62, 25.77, 26.41, 29.73, 30.32, 32.69, 32.99, 36.31, 47.85, 126.67, 127.25, 127.50, 128.25, 128.47, 129.70, 136.89, 137.24, 169.26, 174.01; MS m/z 432 (M+), 327 (M$^+$−PhCO), 306 (M$^+$−CONHC$_6$H$_{11}$), 223, 105, 91, 77; HRMS calcd. for C$_{28}$H$_{36}$N$_2$O$_2$ (M$^+$) m/z 432.2793, found 432.2778.

74. General Procedure for Conventional Biginelli reactions

A solution of 174 mg (0.84 mmol) benzoyloxyethylurea in THF (5 mL) was treated with 3 equiv of β-keto ester, 3 equiv of aldehyde and of concentrated HCl (25 µL). The solution was stirred until completion (TLC), concentrated in vacuo and purified by chromatography on SiO$_2$ (ethyl acetate/hexanes 1:1).

75. 1-(Benzoyloxyethyl)-6-methyl-2-oxo-4-phenyl-1,2,3,4-tetrahydropyrimidine-5-carboxylic acid ethyl ester mp 129° C.

IR (CHCl$_3$) 3425, 3016, 1711, 1684, 1623, 1450, 1392, 1270, 1178; $^1$H NMR (CDCl$_3$) d 7.96 (d, 2 H, J=7.8 Hz), 7.60–7.10 (m, 8 H), 5.39 (bs, 2 H), 4.50–4.40 (m, 3 H), 4.15–3.90 (m, 3 H), 2.60 (s, 3 H), 1.18 (t, 3H, J=7.1 Hz); $^{13}$C NMR (CDCl$_3$) d 166.3, 165.9, 153.4, 148.0, 143.0, 133.1, 129.6, 128.6, 128.4, 127.7, 126.0, 105.3, 63.4, 60.2, 54.0, 40.9, 16.4, 14.1; MS (El) m/z (relative intensity) 408 (M$^+$, 4), 393 (16), 331 (16), 303 (8), 286 (6), 259 (20), 209 (10), 149 (100), 105 (99), 77 (54); HRMS (El) calculated for C$_{23}$H$_{24}$N$_2$O$_5$ 408.1672, found 408.1685.

76. 1-(Benzoyloxyethyl)-6-methyl-2-oxo-4-(2-naphthyl)-1,2,3,4-tetrahydropyrimidine-5-carboxylic acid ethyl ester IR (neat) 3342, 2977, 1714, 1679, 1621, 1450, 1390, 1269, 1219, 1182, 1108, 1070; $^1$H NMR (CDCl$_3$) d 7.95–7.25 (m, 12 H), 5.58 (d, 1 H, J=2.8 Hz), 5.49 (d, 1 H, J=2.8 Hz), 4.60–4.35 (m, 3 H), 4.15–4.00 (m, 3 H), 2.63 (s, 3 H), 1.18 (t, 3H, J=7.1 Hz); $^{13}$C NMR (CDCl$_3$) d 166.4, 166.2, 153.7, 148.4, 140.5, 133.2, 132.9, 129.7, 128.8, 128.5, 128.0, 127.6, 126.3, 126.0, 125.0, 124.4, 105.3, 63.6, 60.4, 54.3, 41.2, 16.6, 14.3; MS (El) m/z (relative intensity) 458 (M$^+$, 26), 443 (22), 412 (9), 385 (11), 353 (11), 331 (24), 309 (30), 263 (6), 209 (12), 149 (100), 105 (87), 77 (36); HRMS (El) calculated for C$_{27}$H$_{26}$N$_2$O$_5$ 458.1842, found 458.1842.

77. 1-(Benzoyloxyethyl)-6-methyl-2-oxo-4-(4-methoxyphenyl)-1,2,3,4-tetrahydropyrimidine-5-carboxylic acid ethyl ester mp 75° C.; IR (CHCl$_3$) 3425, 3025, 1704, 1677, 1621, 1514, 1454, 1392, 1270, 1174, 1114, 1069; $^1$H NMR (CDCl$_3$) d 7.96 (d, 2 H, J=7.1 Hz), 7.56 (t, 1 H, J=7.6 Hz), 7.41 (t, 2 H, J=7.6 Hz), 7.14 (d, 2 H, J=8.7 Hz), 6.62 (d, 2 H, J=8.7 Hz), 5.34 (bs, 2 H), 4.50–4.40 (m, 3 H), 4.15–3.95 (m, 3 H), 3.66 (s, 3H), 2.60 (s, 3 H), 1.19 (t, 3H, J=7.1 Hz); $^{13}$C NMR (CDCl$_3$) d 166.4, 166.2, 159.0, 153.9, 147.9, 135.5, 133.2, 129.7, 128.5, 127.4, 113.9, 105.8, 63.6, 60.3, 55.1, 53.3, 40.9, 16.5, 14.3; MS (EI) m/z (relative intensity) 438 (M$^+$, 5), 423 (27), 365 (13), 331 (7), 316 (6), 289 (30), 243 (6), 209 (5), 149 (92), 105 (100), 77 (50); HRMS (EI) calculated for C$_{24}$H$_{26}$N$_2$O$_6$ 438.1787, found 438.1791.

78. 1-(Benzoyloxyethyl)-6-methyl-2-oxo-4-(2-naphthyl)-1,2,3,4-tetrahydropyrimidine-5-carboxylic acid methyl ester mp 116° C.; IR (CHCl$_3$) 3425, 3012, 1708, 1683, 1623, 1454, 1392, 1275, 1188, 1115, 1076; $^1$H NMR (CDCl$_3$) d 7.88 (d, 2 H, J=8.0 Hz), 7.70–7.30 (m, 10 H), 5.57 (d, 1 H, J=2.6 Hz), 5.52 (bs, 1 H), 4.55–4.45 (m, 3 H), 4.10–3.95 (m, 1 H), 3.66 (s, 3 H), 2.63 (s, 3 H); $^{13}$C NMR (CDCl$_3$) d 166.5, 166.3, 153.9, 148.7, 140.3, 133.1, 132.8, 129.5, 128.7, 128.3, 128.0, 127.5, 126.1, 125.9, 124.7, 124.2, 104.9, 63.5, 53.8, 51.5, 41.0, 16.5; MS (EI) m/z (relative intensity) 444 (M$^+$, 10), 429 (10), 339 (6), 317 (12), 295 (15), 149 (81), 105 (100), 77 (35); HRMS (EI) calculated for C$_{26}$H$_{24}$N$_2$O$_5$ 444.1686, found 444.1685.

79. 1-(Benzoyloxyethyl)-6-ethyl-2-oxo-4-(2-naphthyl)-1,2,3,4-tetrahydropyrimidine-5-carboxylic acid ethyl ester IR (neat) 3340, 2981, 1704, 1681, 1614, 1454, 1382, 1269, 1182, 1108, 1067; $^1$H NMR (CDCl$_3$) d 7.85 (d, 2 H, J=7.1 Hz), 7.70–7.25 (m, 10 H), 5.55 (d, 1 H, J=3.3 Hz), 5.52 (bs, 1 H), 4.55–4.45 (m, 3 H), 4.20–4.05 (m, 2 H), 4.05–3.85 (m, 1 H), 3.55–3.35 (m, 1 H), 2.90–2.75 (m, 1 H), 1.25 (t, 3H, J=7.2 Hz), 1.20 (t, 3H, J=7.1 Hz); $^{13}$C NMR (CDCl$_3$) d 166.4, 165.7, 154.4, 154.1, 140.4, 133.2, 133.0, 129.7, 129.5, 128.9, 128.4, 128.1, 127.7, 126.3, 126.1, 125.0, 124.3, 104.5, 63.7, 60.5, 53.9, 40.8, 22.1, 14.3, 13.1; MS (EI) m/z (relative intensity) 472 (M$^+$, 14), 443 (25), 350 (11), 323 (14), 277 (7), 223 (13), 149 (100), 105 (95), 77 (41); HRMS (EI) calculated for C$_{28}$H$_{28}$N$_2$O$_5$ 472.1980, found 472.1998.

80. 1-(Benzoyloxyethyl)-6-ethyl-2-oxo-4-phenyl-1,2,3,4-tetrahydropyrimidine-5-carboxylic acid ethyl ester mp 111° C.; IR (neat) 3340, 2981, 1714, 1687, 1616, -1450, 1383, 1269, 1209, 1172, 1108, 1074; $^1$H NMR (CDCl$_3$) d 7.94 (d, 2 H, J=7.2 Hz), 7.55–7.05 (m, 8 H), 5.41 (bs, 1 H), 5.36 (d, 1 H, J=3.2 Hz), 4.55–4.40 (m, 3 H), 4.20–4.00 (m, 2 H), 4.00–3.85 (m, 1 H), 3.50–3.30 (m, 1 H), 2.90–2.70 (m, 1 H), 1.23 (t, 3 H, J=7.3 Hz), 1.19 (t, 3 H, J=7.1 Hz); $^{13}$C NMR (CDCl$_3$) d 166.4, 165.7, 154.2, 154.1, 143.2, 133.2, 129.7, 128.7, 128.5, 127.8, 126.2, 104.6, 63.7, 60.4, 53.7, 40.7, 22.0, 14.2, 13.0; MS (EI) mlz (relative intensity) 422 (M$^+$, 5), 393 (95), 377 (10), 345 (31), 317 (14), 273 (35), 243 (8), 223 (36), 195 (11), 149 (100), 105 (92), 77 (52); HRMS (EI) calculated for C$_{24}$H$_{26}$N$_2$O$_5$ 422.1827, found 422.1842.

81. 4-(tris(Perfluorodecylethyl)silyl)benzoyloxyethylurea 23

A solution of 4-(tris(perfluorodecylethyl)silyl)benzoic acid propyl thioester 22, 88 mg, 47.6 μmol) in FC-72 (6 mL) was treated at 25° C. with bromine (30 μL, 0.58 mmol). After 5 h, the mixture was extracted with dichloromethane (10 mL). The dichloromethane phase was extracted with FC-72 (3×10 mL). The combined fluorous phases were evaporated. The resulting acid bromide (88 mg) was diluted with BTF (1 mL) and added to a suspension of hydroxyethylurea (27 mg, 0.26 mmol), triethylamine (36 μL, 0.26 mmol) and 4-dimethylaminopyridine (3 mg, 25 μmol) in dry dioxane (0.50 mL) at 35° C. After stirring for 22 h at 35° C., the volatiles were removed in vacuo and FC-72 (20 mL ), water (10 mL) and toluene (5 mL) were added. The combined water/toluene phases were washed with FC-72/(5×10 mL). The combined fluorous phases were filtered and concentrated to give 23 as a white solid (79 mg , 89%): $^1$H NMR (acetone-d$_6$) d 8.10 (d, 2 H, J=8.1 Hz), 7.86 (d, 2 H, J=8.1 Hz), 5.96 (bs, 1 H), 5.13 (bs, 2 H), 4.35 (t, 2 H, J=5.5 Hz), 3.53 (q, 2 H, J=5.5 Hz), 2.45–2.20 (m, 6 H), 1.50–1.40 (m, 6 H).

82. General Procedure for Biginelli reactions

A solution of 23 (18 mg, 9.6 μmol) in THF/BTF (2/1, 0.75 mL) was treated at 25° C. with 10 equiv of B-keto ester, 10 equiv of aldehyde and concentrated HCl (1 μL). After 3 days at 50° C., volatiles were removed in vacuo and FC-84 and toluene (10 mL each) were added. The toluene phase was extracted with FC-84 (5×5 mL). The combined fluorous phases were filtered and concentrated. The resulting white solid 24 was diluted with THF/BTF (1:1, 0.50 mL) and treated dropwise with a 1 M tributylammonium fluoride (TBAF) solution in THF (10 μL, 10 μmol). After stirring for 0.5 h at 25° C., volatiles were removed in vacuo and FC-84 and toluene were added (10 mL each). The fluorous phase was extracted with toluene (3×5 mL). The combined toluene phases were extracted with sat. aqueous NaHCO$_3$ solution (3×10 mL) and brine (3×10 mL), dried (Na$_2$SO$_4$), filtered and concentrated. The resulting products 25 (FIG. 14) were spectroscopically ($^1$H NMR) identical to those prepared by the conventional procedure.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method for carrying out a chemical reaction, comprising the steps of:

forming an organic/fluorous solubilizing liquid phase comprising a solvent system, the solvent system adapted to substantially solubilize a fluorous reaction component, the solvent system also being selected to substantially solubilize at least one organic reaction component convertible in a reaction scheme to an organic product, the fluorous reaction component comprising sufficient fluorine to render the organic product separable via an organic/fluorous separation technique from any excess fluorous reaction component and any fluorous byproduct of the fluorous reaction component produced in the reaction scheme;

contacting the fluorous reaction component and the organic reaction component in the organic/fluorous solubilizing liquid phase under conditions suitable to effect a desired reaction of the fluorous reaction component and the organic reaction component; and after production of the organic product, separating the organic product from any excess fluorous reaction component and any fluorous byproduct.

2. The method of claim 1 wherein the step of separating the organic product from any excess fluorous reaction component and any fluorous byproduct includes the step of causing a phase separation into a fluorous liquid phase and an organic phase, the fluorous reaction component comprising a sufficient fluorine to render any excess fluorous reaction component and any fluorous byproduct preferentially partitionable into the fluorous phase.

3. The method of claim 1 wherein the fluorous reaction component has the formula $$XM[(R)(Rf)]_3,$$

wherein X is H, F, Cl, Br, I, $N_3$, $OR^1$, OH, OOH, $OOR^1$ $SR^1$, $SeR^1$, CN, NC, $NR^1R^2$, a cyclic group, a substituted cyclic group, a heterocyclic group, a substituted heterocyclic group, a linear or branched alkyl group of 1 to 20 carbons, a substituted linear or branched alkyl group, an alkenyl group, a substituted alkenyl group, an alkynyl group, a substituted alkynyl group, an acyl group, a substituted acyl group, $M'((R')(Rf'))_3$, $OM'((R')(Rf'))_3$ or $OOM'((R')Rf'))_3$, wherein M' is Si, Ge, or Sn, and wherein $R^1$ and $R^2$ are each independently the same or different H, a linear or branched alkyl group, a substituted linear or branched alkyl group, a cyclic alkyl group, a substituted cyclic alkyl group, an alkylsulfonyloxy group, a perfluoroalkylsulfonyloxy group, an acyl group, a substituted acyl group, or a perfluoroacyloxy group, and wherein M is Si, Ge or Sn, and wherein R and R' are each independently the same or different an alkylene group of 1 to 6 carbons or a substituted alkylene group of 1 to 6 carbons, and wherein Rf and Rf' are each independently a linear perfluoroalkyl group of 3 to 20 carbons, a branched perfluoroalkyl group of 3 to 20 carbons, or a hydrofluoroalkyl group of 3 to 20 carbons, the hydrofluoroalkyl group comprising up to one hydrogen atom for each two fluorine atoms.

* * * * *